United States Patent
Schoenhofer et al.

(10) Patent No.: US 10,532,032 B2
(45) Date of Patent: Jan. 14, 2020

(54) ROLLED COLLAGEN CARRIER

(71) Applicant: TAKEDA AS, Asker (NO)

(72) Inventors: Wolfgang Schoenhofer, St. Poelten (AT); Pernille Dybendal Pedersen, Frederiksberg (DK); Poul Bertelsen, Roskilde (DK); Henrik Braender, Kalundborg (DK); Ingrid Blanka, Hellmonsoedt (AT); Henrik Neuschaefer Larsen, Soborg (DK)

(73) Assignee: TAKEDA AS, Asker (NO)

( * ) Notice: Subject to any disclaimer, the term of this patent is extended or adjusted under 35 U.S.C. 154(b) by 259 days.

(21) Appl. No.: 15/728,799

(22) Filed: Oct. 10, 2017

(65) Prior Publication Data
US 2018/0085322 A1 Mar. 29, 2018

Related U.S. Application Data

(62) Division of application No. 14/117,882, filed as application No. PCT/DK2012/050178 on May 24, 2012, now Pat. No. 9,814,686.

(30) Foreign Application Priority Data

May 24, 2011 (EP) .................................... 11167379

(51) Int. Cl.
*A61K 9/70* (2006.01)
*A61F 13/02* (2006.01)
(Continued)

(52) U.S. Cl.
CPC ........ *A61K 9/7007* (2013.01); *A61F 13/0276* (2013.01); *A61K 38/363* (2013.01);
(Continued)

(58) Field of Classification Search
CPC ...... A61B 17/0057; A61B 2017/00004; A61B 2017/00637; A61B 17/00234;
(Continued)

(56) References Cited

U.S. PATENT DOCUMENTS

| 4,453,939 A | 6/1984 | Zimmerman |
| 5,147,387 A | 9/1992 | Jansen et al. |

(Continued)

FOREIGN PATENT DOCUMENTS

| DE | 19546435 A1 | 6/1997 |
| EA | 006686 B1 | 2/2006 |

(Continued)

OTHER PUBLICATIONS

Russian office action dated Feb. 2, 2017 for corresponding Russian Patent Application No. 2014907745 with English translation attached.
(Continued)

*Primary Examiner* — Katherine M Shi
(74) *Attorney, Agent, or Firm* — Nath, Goldberg & Mayer; Joshua B. Goldberg

(57) ABSTRACT

The invention relates to a process for the preparation of a rolled compressed collagen carrier and a process for unrolling said rolled compressed collagen carrier. Said rolled compressed collagen carrier is ready for use in minimally invasive surgery. The invention also relates to a rolled compressed collagen carrier for use in the prevention or treatment of injury associated with performing minimally invasive surgery.

14 Claims, 11 Drawing Sheets

(51) Int. Cl.

| | | |
|---|---|---|
| *A61K 38/36* | (2006.01) | |
| *A61K 38/48* | (2006.01) | |
| *A61K 47/42* | (2017.01) | |
| *A61L 24/04* | (2006.01) | |
| *A61L 31/04* | (2006.01) | |
| *A61B 17/00* | (2006.01) | |

(52) U.S. Cl.
CPC .......... *A61K 38/4833* (2013.01); *A61K 47/42* (2013.01); *A61L 24/043* (2013.01); *A61L 31/041* (2013.01); *A61B 17/0057* (2013.01)

(58) Field of Classification Search
CPC .. A61K 38/363; A61K 38/4833; A61K 38/39; A61K 9/7007; A61K 9/0024; A61F 2/0063; A61F 2210/0004; A61F 13/00029; A61F 13/00063; A61F 2002/30062

See application file for complete search history.

(56) References Cited

U.S. PATENT DOCUMENTS

| | | | |
|---|---|---|---|
| 5,290,310 | A | 3/1994 | Makower et al. |
| 5,334,216 | A | 8/1994 | Vidal et al. |
| 5,810,711 | A | 9/1998 | Scheyer |
| 5,942,278 | A | 8/1999 | Hagedorn et al. |
| 6,177,126 | B1 | 1/2001 | Hagedorn et al. |
| 7,052,713 | B2 | 5/2006 | Stimmeder |
| 2002/0153632 | A1 | 10/2002 | Schaufler |
| 2002/0164322 | A1 | 11/2002 | Schaufler |
| 2003/0176828 | A1 | 9/2003 | Buckman et al. |
| 2005/0155608 | A1 | 7/2005 | Pavcnik et al. |
| 2005/0178396 | A1 | 8/2005 | Hunter et al. |
| 2005/0183731 | A1 | 8/2005 | Hunter et al. |
| 2005/0186244 | A1 | 8/2005 | Hunter et al. |
| 2005/0187140 | A1 | 8/2005 | Hunter et al. |
| 2005/0196421 | A1 | 9/2005 | Hunter et al. |
| 2005/0208095 | A1 | 9/2005 | Hunter et al. |
| 2005/0214277 | A1 | 9/2005 | Schaufler |
| 2005/0234397 | A1 | 10/2005 | Poff et al. |
| 2005/0277978 | A1 | 12/2005 | Greenhalgh |
| 2008/0031934 | A1 | 2/2008 | MacPhee et al. |
| 2008/0131473 | A1 | 6/2008 | Brown et al. |
| 2009/0156711 | A1 | 6/2009 | Van Holten et al. |
| 2009/0275129 | A1 | 11/2009 | Cooper et al. |
| 2010/0055149 | A1 | 3/2010 | Li et al. |
| 2010/0106068 | A1 | 4/2010 | Karpiel et al. |
| 2011/0040279 | A1 | 2/2011 | Walsh |
| 2012/0052040 | A1 | 3/2012 | Hunter et al. |
| 2012/0207808 | A1 | 8/2012 | Evans et al. |
| 2014/0072612 | A1 | 3/2014 | Schoenhofer et al. |

FOREIGN PATENT DOCUMENTS

| | | | |
|---|---|---|---|
| EP | 1053757 | B1 | 11/2000 |
| EP | 2052746 | A2 | 4/2009 |
| GB | 422990 | B1 | 1/1935 |
| GB | 423017 | B1 | 1/1935 |
| GB | 487258 | B1 | 6/1938 |
| JP | 200473221 | A | 3/2004 |
| JP | 2004188037 | A | 7/2004 |
| JP | 2004520124 | A | 7/2004 |
| JP | 2005506110 | A | 3/2005 |
| JP | 2007159866 | A | 6/2007 |
| JP | 2014519897 | A | 8/2014 |
| RU | 2018540 | C1 | 8/1994 |
| RU | 2118176 | C1 | 8/1998 |
| RU | 2188206 | C2 | 8/2002 |
| RU | 2235539 | C1 | 9/2004 |
| WO | 9413210 | A1 | 6/1994 |
| WO | 1997021383 | A1 | 6/1997 |
| WO | 02058749 | A2 | 8/2002 |
| WO | 02058750 | A2 | 8/2002 |
| WO | D2058749 | A2 | 8/2002 |
| WO | 02070594 | A2 | 9/2002 |
| WO | 03009764 | A1 | 2/2003 |
| WO | 2006044879 | A2 | 4/2006 |
| WO | 2006044882 | A2 | 4/2006 |
| WO | 2006119256 | A2 | 11/2006 |
| WO | 2007117855 | A1 | 10/2007 |
| WO | 2009109963 | A1 | 9/2009 |
| WO | 2009126870 | A2 | 10/2009 |
| WO | 2009134447 | A1 | 11/2009 |
| WO | 2012159635 | A1 | 11/2012 |

OTHER PUBLICATIONS

Carbon, RT et al., "Tissue Sealing Concept in Minimally Invasive Surgery in Children", Pediatric Endosurgery & Innovative Techniques, vol. 5, Issue 1, pp. 5-12, (Jul. 8, 2004).
Carbon, RT et al. "AMISA: Innovative tissue management in MIS", Minimally Invasive Therapy & Allied Technologies, vol. 8, Issue 5, pp. 347-353, (Jul. 10, 2009).
Saif, R et al., "Use of Fibrin-Based Sealants and Gelatin-Matrix Hemostats in Laparoscopic Liver Surgery", Surgical Laparoscopy, Endoscopy & Percutaneous Techniques, vol. 21, Issue 3, pp. 131-141 (Jun. 2011).
Lee, MGM et al. "Application of Fibrin Sealant in Surgery", Surgical Innovation, vol. 12, No. 3, pp. 203-213 (2005).
Somil R et al. "Newer Haemostats in Cannine Practice", International Journal of Agricultural Sciences and Veterinary Medicine, vol. 1, No. 3, pp. 88-94 (Aug. 2013).
Wheat, JC et al. "Advances in Bioadhesives, Tissue Sealants, and Heostatic Agents", Urologic Clinics of North America, Elsevier (2009).
De Cogain, MR et al. "Advances in Tubeless Percutaneous Nephrolithotomy and Patient Selection: An Update", Current Urology Reports, Springer Link, vol. 14, Issue 2, pp. 130-137 (Apr. 2013).
Lewis, KM et al. "Control of bleeding in surgical procedures: critical appraisal of HEMOPATCH (Sealing Hemostat)", Medical Devices: Evidence and Research, Dove Press, issue 9, pp. 1-10, (2016).
Liu T et al. "Comparison of the Nuss and sternal turnover procedures for primary repair of pectus excavatum" Asian Journal of Surgery, vol. 37, pp. 30-34 (2014).
Singh I "Robot-assisted laparoscopic partial nephrectomy: Current review of the technique and literature", Journal of Minimal Access Surgery, vol. 5(4), pp. 87-92 (Oct.-Dec. 2009).
2016 Iran Search Results from counter-part Iran No. 13915014000301810.
Endodock ® Instruction Leaflet by Nycomed.
2016 Photograph of Endodock ® apparatus in retracted configuration.
2016 Photograph of Endodock ® apparatus in extended configuration.
Fukui, et al., "A case of laparoscopically detected severe adhesion and diastasis caused by the fibrinogen sheet placed at adenomyomectomy", Journal of the Aomori Society of Obstetricians and Gynecologists, 2007, vol. 22, No. 1, pp. 20-25.
English translation of Japanese Patent Application No. 2008-176559.
Bisertes, Jacques. "TachoSil: the value of its use in urologic surgerys" Journal De Chirurgie, Paris 2007 vol. 144(1), pp. 82-83.
Lattouf et al. "Practical hints for hemostasis in laparoscopic surgery", Minimally Invasive Therapy, 2007, 16(1), pp. 45-51.
Ahmed et al. BJUI Letters. Journal Compilation, 2009, 104, 269-272.
Rickenbacher et al. "Efficacy of TachoSil a fibrin-based haemostat in different fields of surgery—a systemic review". Expert Opinion on Biological Therapy. 2009, 9(7), pp. 897-907.
Van Dijk et al. "Haemostasis in laparoscopic partial nephrectomy: Current status". Minimally Invasive Therapy & Allied Technologies. 2007, 16(1), pp. 31-44.
Rane et al. "Evaluation of a Hemostatic Sponge (TachoSil) for Sealing of the Renal Collecting System in a Porcine Laparoscopic Partial Nephrectomy Survival Model". Journal of Endourology, 24(4), 2010.

(56) References Cited

OTHER PUBLICATIONS

Carbon et al. "Fast-track Surgery of Recurrent Pneumothorax in Patients with Cystic Fibrosis—Superiority of Minimally Invasive Tissue Management (ATSS)". Medimond, 2007, pp. 15-28.
Sanseverino et al. "Laparoscopic Partial Nephrectomy with Parenchimal Haemostasis with TachoSil Application". Journal of Endourology. 2009, 23, p. A362.
Erdogru et al. "Laparoscopic transvesical repair of recurrent vesicovaginal fistula using with fleece-bound sealing system". Archives of Gynecology and Obstetrics. 2008, 277, pp. 461-464.
Slupski et al. Suture-Free Laparoscopic Partial Nephrectomy—Improvement of Hemostasis with Human Fibrinogen and Thrombin-Coated Collagen Patch (TachoSil). European Urology Supplements. 2010, 9(6), p. 636.
Liatsikos et al. "Cautery Free Nerve Sparing Extraperitoneal Endoscopic Radical Prostatecomy: The Use of TachoSil for Hemostasis". Journal of Endourology. 2006, 20(1), A294.
Murphy et al. "TachoSil is an Effective Haemostatic Aid During Laparoscopic Partial Nephrectomy in a Porcine Model". European Urology Supplements. 2006, 5(2), p. 329.
Brochuere, Wissenwertes ueber Tachosil für Operateure, Nycomed 2009.
Nakajima et al. "A Simple Application Technique of Fibrin-Coated Collagen Fleece (TachoComb) in Laparoscopic Surgery". Surgery Today. 2007, 37, pp. 176-179.
Carbon et al. "AMISA: innovative tissue management in MIS". Minimally Invasive Therapy & Allied Technologies. 1999, 8(5) 347-353.
Carbon et al. "Minimalinvasive Kinderchirurgie: Entwicklung und Fortschritt durch innovative Technologie". Kiln Padiatr. 2001. 213, pp. 99-103.
TachoSil. A guided tour. Brochure, 2007.
Carbon et al. "Innovatives Gewebemanagement in der minimal invasiven Chirurgie". Medizin & Wissen, 2000. English Translation attached.
Machine Translation of JP 2004-520124A, published Jul. 8, 2004.
Nohuz, Erdogan, et al., "Efficiency of TachoSil to Prevent Postsurgical Adhesion Development on Laparoscopic Rat Model", Gynecol Surg, vol. 6, 2009, pp. 323-329.
Gordon, LE., "The New Science of Strong Materials or Why You Don't Fall Through the Floor", 1976, pp. 40-43.

ROLLED COLLAGEN CARRIER

This is a Divisional Application of U.S. patent application Ser. No. 14/117,882, filed Nov. 15, 2013, an application filed as a national stage under 371 of Application No. PCT/DK2012/050178 filed May 24, 2012 and claiming benefit from European Application No. 11167379.4, filed May 24, 2011, the content of each of which is hereby incorporated by reference in its entirety.

TECHNICAL FIELD OF THE INVENTION

One aspect of the present invention relates to a process for coiling a collagen carrier. Another aspect of the present invention relates to a form-stable coiled collagen carrier. The present invention further relates to a method for delivering the coiled collagen carrier to a target location, and to methods of treatment or surgery using the coiled collagen carrier, such as a method for performing minimally invasive surgery. The present invention also relates to a coiled collagen carrier for use in therapy and/or a method of surgery, such as a method for performing minimally invasive surgery. A further aspect of the present invention relates to an apparatus for providing a coiled collagen carrier.

The present invention also relates to a process for the preparation of a rolled collagen carrier, or a compressed collagen carrier or a rolled compressed collagen carrier.

In addition, the present invention relates to a rolled compressed collagen carrier, said rolled compressed collagen carrier being obtainable by said process.

Further, the present invention relates to a process of un-rolling a rolled collagen carrier, or a rolled compressed collagen carrier. Further, the present invention relates to an unrolled rolled compressed collagen carrier, said rolled/unrolled compressed collagen carrier being obtainable by said process.

In another embodiment the present invention relates to a rolled collagen carrier or a compressed collagen carrier or a rolled compressed collagen carrier. In yet another embodiment the present invention relates to an unrolled rolled collagen carrier or an unrolled rolled compressed collagen carrier. Further, the present invention relates to an unrolled rolled compressed collagen carrier, said unrolled rolled compressed collagen carrier being obtainable by said process.

In another embodiment the invention relates to a rolled compressed collagen carrier for use in minimally invasive surgery.

In particular, the present invention relates to a rolled compressed collagen carrier for use in the prevention and/or treatment of injury to tissues and organs during open and especially minimally invasive surgery.

BACKGROUND OF THE INVENTION

Medicated sponges are used during open surgery to stop local bleeding (hemostasis/haemostasis). They react upon contact with blood, other body fluids or saline to form a clot that glues the sponge to the tissue surface and hemostasis is reached in a few minutes. Medicated sponges are sponges, such as a collagen carrier as defined below, such as a cellulose sponge as disclosed in EP2052746.

Collagen has been used as a haemostatic agent for decades. A product that combines the haemostatic features of fibrin glue with the asset of collagen as a carrier has been developed and manufactured under the trademark TachoSil®. TachoSil® is a ready-to-use collagen carrier with a coating of the active components of fibrin glue: human fibrinogen and human thrombin. The product is described in WO 02/058 749, WO 02/070 594 and WO 02/058 750. TachoSil® contains fibrinogen and thrombin as a dried coating on the surface of a collagen sponge. In contact with body fluids, e.g. blood, lymph or physiological saline solution the components of the coating dissolve and partly diffuse into the wound surface. This is followed by the fibrinogen-thrombin reaction which initiates the last phase of physiological blood coagulation. Fibrinogen is converted into fibrin monomers which spontaneously polymerise to a fibrin clot, which holds the collagen sponge tightly to the wound surface.

TachoSil® has been sold since 2004 by Nycomed and is used in open surgery for hemostasis and sealing. Traditional open surgery usually requires a long incision of the skin.

Contrary to open surgery, a minimally invasive procedure is any procedure (surgical or otherwise) that is less invasive than open surgery used for the same purpose. Minimally invasive surgery (MIS) procedures are performed through one or more access orifices e.g. short incisions ('keyhole surgery') or through natural body openings. Hence, MIS procedures require specially designed surgical instruments which are placed through these access orifices. In abdominal surgery, the access of the instruments is usually done through so-called trocars, which are mostly rigid tubes with a typical inner diameter of 5 to 12 mm. The small size of the access orifices used in MIS restricts what can be inserted into the orifices. Therefore, all surgical tools and materials used in MIS procedures must be of a size and condition that allow for their insertion through the access orifices and they need, of course, as all medical tools to be sterile. Hence, tools and materials are most often specially designed for use in MIS.

WO 97/21383 (Nycomed Arzneimittel GmbH) discloses a surgical instrument comprising an applicating member, wherein the applicating member comprises a rodshaped portion so as to allow a sheet of surgical material such as, e.g. TachoComb® (coated equine collagen sponge/Nycomed) to be rolled up to form a carpetlike roll of surgical material on the rod-shaped portion of the applicating member. However, this manual instrument for hand-rolling surgical materials, such as collagen carriers, has several disadvantages as described below. WO 02/058749 discloses the non-sterile insertion of TachoComb® into an endoscopic equipment, wherein the sample is flattened manually to be able to wrap it manually around a guiding "pin". WO 02/058749 teaches that the collagen product "has to stay flexible enough in dry condition to be bent and rolled up" (p 29, lines 19-20). Thus WO 02/058749 only relates to manual (i.e. hand-rolled), non-sterile rolling of TachoComb® and further teaches that the rolling process must be "dry". One significant problem with the above methods which use an applicating member or guiding pin for hand-coiling the collagen carrier arises in case application of multiple rolled/coiled collagen carriers is necessary in quick succession (e.g. either because one collagen carrier is insufficient to completely stop the bleeding, or due to an error in application of the first collagen carrier(s)). In this instance the same applicating member cannot be used to apply the second collagen carrier: instead, multiple applicating members must be prepared. This is because in order to apply collagen-based products such as the TachoComb® product correctly, the applicating member must be completely dry in order to avoid activating the adhesive properties of the collagen carrier. If the collagen carrier becomes prematurely wet by contacting a wet application member or guiding pin, the carrier will stick to the applicating member/guiding pin and/or become an unusable sticky lump of material. Another way of rolling up collagen-based surgical sheets is for the surgeon to use his/her hands in the same way as for rolling up a cigarette, however for this and all the manually-rolled cases above the rolled surgical product is not form-stable and is therefore more difficult to manipulate in a controlled manner after insertion into the body: the non-form-stable product may "spring open" in an uncontrolled way during the unrolling process and adhere incorrectly. This is a particular issue for MIS surgery, where it is harder to manipulate the product once it is in the body as one only has indirect access to the surgical sheet via endoscopic surgical instruments. One way of lessening the effect of the rolled collagen-based surgical product being non-form-stable is to tie the rolled product together with a suture, however this solution is only relevant where the coiled carrier in not unrolled in vivo but rather maintained in the patient in a coiled state (e.g. in a partial nephrectomy procedure).

For applications such as MIS there is thus a need to produce an improved coiled collagen-based surgical product, which has dimensions useful for MIS applications and useful properties for promoting coagulation and wound sealing, but which allows easy application of more than one collagen carrier in quick succession and furthermore gives the surgeon improved control of the complex process of moving the carrier to the desired tissue site and applying it.

A further problem with all the above types of manual coiling processes for collagen carriers is that the results are of course highly dependent on the skills of the individual medical practitioner carrying out the coiling process, and therefore highly variable in reproducibility, and may lead to a non-sterile product, un-even and thus un-reproducible coiling/rolling of the collagen carrier, and un-predictable loss of coating.

Thus, there exists a need in the art for a collagen carrier coated with human fibrinogen and human thrombin especially designed for use in minimally invasive surgery that is ready-to-use, maintains sterility, and which has an acceptable hemostatic and tissue sealing effectiveness and adhesive strength to living tissue, and also which allows easy application of more than one collagen carrier in quick succession for MIS techniques, and also allows the surgeon more control on application to the desired tissue during an MIS procedure in order to avoid adhesion of the collagen carrier to an incorrect site, would be advantageous.

Hence, a ready-to-use collagen carrier coated with human fibrinogen and human thrombin designed particularly for use in MIS, such as designed to fit an access tube and/or orifice in MIS, preferably such as to be inserted into endoscopic devices would be advantageous, and in particular a ready-to-use collagen carrier coated with human fibrinogen and human thrombin having an acceptable hemostatic effectiveness, adhesive strength to living tissue and sterility that is ready-to-use in MIS, allows easy application of more than one collagen carrier in quick succession for MIS techniques, and also allows the surgeon more control on application to the desired tissue during an MIS procedure in order to avoid adhesion of the collagen carrier at the incorrect site, would be advantageous.

SUMMARY OF THE INVENTION

It is an object of the present invention to provide a ready-to-use collagen carrier coated with human fibrinogen and human thrombin designed e.g. for use in minimally invasive surgery, such as designed preferably to be inserted into endoscopic devices, that solves the above mentioned problems.

One aspect of the present invention relates to a process for coiling a collagen carrier, the collagen carrier comprising (i) a collagen layer and (ii) a coating layer comprising fibrinogen and thrombin, said process comprising the sequential steps of:
humidifying at least part of said collagen carrier,
coiling said collagen carrier by gripping the collagen carrier between a pair of elongate members, and rotating the pair of elongate members about an axis being parallel to a longitudinal extension of the elongated members in order to coil the collagen carrier on the members, while the collagen carrier is supported by a support device,
drying the coiled collagen carrier,
thereby providing a form-stable coiled collagen carrier.

One embodiment of the present invention relates to a process for coiling a collagen carrier, the collagen carrier comprising (i) a collagen layer and (ii) a coating layer comprising mostly solid fibrinogen and mostly solid thrombin, said process comprising the sequential steps of:
humidifying at least part of said collagen carrier,
coiling said collagen carrier by gripping the collagen carrier between a pair of elongate members, and rotating the pair of elongate members about an axis being parallel to a longitudinal extension of the elongated members in order to coil the collagen carrier on the members, while the collagen carrier is supported by a support device,
drying the coiled collagen carrier,
thereby providing a form-stable coiled collagen carrier.

The present invention further relates to a coiled collagen carrier obtainable by—or alternatively obtained by—the process of the present invention.

A further aspect of the present invention relates to a coiled collagen carrier
comprising a collagen layer and a coating layer on top of the collagen layer, the coating layer comprising thrombin and fibrinogen, and
having the shape of an elongate element with a number of windings of the collagen carrier about the longitudinal axis of the elongate element and at least the outer winding(s) being orientated so that the coating layer constitutes the outer surface of each of said outer winding(s),
wherein
the coiled collagen carrier is form-stable and defines a collagen carrier in a coiled configuration where said outer winding(s) proceed along a spiral in a cross section of the collagen carrier.

The present invention further relates to a method for delivering the coiled collagen carrier of the present invention to a target location, comprising the step of passing said coiled collagen carrier through an orifice or access tube to the target location. The present invention further relates to the use of the coiled collagen carrier according to the present invention in therapy and/or a method of surgery.

A further aspect of the present invention is an apparatus for providing a coiled collagen carrier, the apparatus comprising
a device for applying moisture to a collagen carrier prior to coiling of the collagen carrier,
a coiling device comprising rotatable gripping means for gripping the collagen carrier along an edge and coiling the collagen carrier, and a support device supporting the collagen carrier while being coiled.

Another aspect of the invention relates to a process for the preparation of a rolled compressed collagen carrier comprising the steps of a) providing a collagen carrier having a coating comprising solid fibrinogen and solid thrombin evenly distributed and fixed upon said collagen carrier b) optionally humidifying at least part of said collagen carrier providing an optionally humidified collagen carrier, c) compressing said optionally humidified collagen carrier providing a compressed collagen carrier, d) rolling said compressed collagen carrier, e) obtaining a rolled compressed collagen carrier, f) optionally drying the rolled compressed collagen carrier of step e), g) optionally sterilizing the rolled compressed collagen carrier of step e) or f), h) optionally packing the rolled compressed collagen carrier of step e), f) or g) into a suitable container, and thereby obtaining a rolled compressed collagen carrier having at least one of the following physical properties:

I. a diameter of at the most 10 mm

II. an adhesive strength of at least 30 mm Hg, such as at least 35 mmHg, such as preferably 40 mmHg as measured by a pressure test (PCT) after un-rolling of said rolled compressed collagen carrier, and III. a sterility assurance level (SAL) of $10^{-6}$.

Another aspect of the present invention relates to a process for the preparation of a compressed collagen carrier, comprising the steps of a. providing a collagen carrier having a coating comprising solid fibrinogen and solid thrombin evenly distributed and fixed upon said collagen carrier b. optionally humidifying at least part of said collagen carrier providing an optionally humidified collagen carrier, c. compressing said optionally humidified collagen carrier providing a compressed collagen carrier d. optionally drying said compressed collagen carrier of step c), e. optionally sterilizing said compressed collagen carrier of step c) or d), f. packing said compressed collagen carrier of step c), d) or e) into a suitable container, and thereby obtaining a compressed collagen carrier having at least one of the following physical properties:

I. a thickness of at the most 4 mm

II. an adhesive strength of at least at least 30 mm Hg, such as at least 35 mmHg, such as preferably 40 mmHg as measured by a pressure test (PCT)

III. a sterility assurance level (SAL) of $10^{-6}$.

Yet another aspect of the present invention is to provide a process for the preparation of a rolled collagen carrier comprising the steps of a. providing a collagen carrier having a coating comprising solid fibrinogen and solid thrombin evenly distributed and fixed upon said collagen carrier b. optionally humidifying at least part of said collagen carrier providing an optionally humidified collagen carrier, c. rolling said collagen carrier providing a rolled collagen carrier, d. optionally drying the rolled collagen carrier of step c), e. optionally sterilizing the rolled collagen carrier of step c) or d), f. optionally packing the rolled collagen carrier of step c), d) or e) into a suitable container, and thereby obtaining a rolled collagen carrier having at least one of the following physical properties:

I. a diameter of at the most 10 mm

II. an adhesive strength of at least at least 30 mm Hg, such as at least 35 mmHg, such as preferably 40 mmHg as measured by a pressure test (PCT) after un-rolling of said rolled collagen carrier, and III. a sterility assurance level (SAL) of $10^{-6}$.

Still another aspect of the present invention is to provide a process of un-rolling a rolled compressed collagen carrier, comprising the steps of a) providing a rolled compressed collagen carrier prepared according to the invention, b) un-packing said rolled compressed collagen carrier from said suitable container, c) passing said rolled compressed collagen carrier through an access orifice, such as a trocar, d) un-rolling said rolled compressed collagen carrier upon exit from said access orifice, e) obtaining an unrolled rolled compressed collagen carrier having an adhesive strength of at least 40 mmHg as measured by a pressure test (PCT), and a sterility assurance level (SAL) of $10^{-6}$.

Another aspect of the present invention is to provide a process of un-rolling a rolled collagen carrier, comprising the steps of:

a) providing a rolled collagen carrier prepared according to the invention, b) un-packing said rolled collagen carrier from said suitable container, c) passing said rolled collagen carrier through an access orifice, such as a trocar d) un-rolling said rolled collagen carrier upon exit from said access orifice, e) obtaining an unrolled rolled collagen carrier having an adhesive strength of at least 40 mmHg as measured by a pressure test (PCT), and a sterility assurance level (SAL) of $10^{-6}$.

A further aspect of the present invention is to provide a rolled compressed collagen carrier prepared according to the process of the invention, said rolled compressed collagen carrier having a coating comprising solid fibrinogen and solid thrombin that is evenly distributed and fixed upon said collagen carrier, and having at least one of the following physical properties:

I. a diameter of at the most 10 mm

II. an adhesive strength of at least 40 mmHg as measured upon un-rolling by a pressure test (PCT)

III. a sterility assurance level (SAL) of $10^{-6}$.

Another aspect of the present invention is to provide a rolled compressed collagen carrier obtainable by a process comprising the steps of a. providing a collagen carrier having a coating comprising solid fibrinogen and solid thrombin that is evenly distributed and fixed upon said collagen carrier, b. optionally humidifying at least part of said collagen carrier providing an optionally humidified collagen carrier, c. compressing said optionally humidified collagen carrier providing a compressed collagen carrier, d. rolling said compressed collagen carrier,
e. obtaining a rolled compressed collagen carrier
f. optionally drying the rolled compressed collagen carrier of step e),
g. optionally sterilizing said rolled compressed collagen carrier of step e) or f),
h. optionally packing said rolled compressed collagen carrier of step e), f) or g) into a suitable container
and thereby obtaining a rolled compressed collagen having at least one of the following physical properties:
I. a diameter of at the most 10 mm
II. an adhesive strength of at least 40 mmHg as measured by a pressure test (PCT) after un-rolling of said collagen carrier
III. a sterility assurance level (SAL) of $10^{-6}$.

Still another aspect of the invention relates to an unrolled rolled compressed collagen carrier according the invention having at least one of the following physical properties:
I. a thickness of at the most 4 mm
II. an adhesive strength of at least 40 mmHg as measured by a pressure test (PCT)
III. a sterility assurance level (SAL) of $10^{-6}$
IV. said rolled compressed collagen carrier is capable of adhering to the tissue while being unrolled without recoiling.

Yet another aspect of the invention relates to an unrolled rolled compressed collagen carrier according to the invention having a coating comprising solid fibrinogen and solid thrombin evenly distributed and fixed upon said collagen carrier, and having at least one of the following physical properties:
I. a thickness of at the most 4 mm
II. an adhesive strength of at least 40 mmHg as measured by PCT chamber
III. a sterility assurance level (SAL) of $10^{-6}$
IV. said rolled compressed collagen carrier is capable of adhering to the tissue while being unrolled without recoiling Another aspect of the invention relates to a compressed collagen carrier according to the invention having a coating comprising solid fibrinogen and solid thrombin that is evenly distributed and fixed upon said collagen carrier, and having at least one of the following physical properties:
I. a thickness of at the most 4 mm
II. an adhesive strength of at least 40 mmHg as measured by a pressure test (PCT)
III. a sterility assurance level (SAL) of $10^{-6}$.

Another aspect of the invention relates to a rolled collagen carrier according to the invention having a coating comprising solid fibrinogen and solid thrombin that is evenly distributed and fixed upon said collagen carrier, and having at least one of the following physical properties:
I. a diameter of at the most 10 mm
II. an adhesive strength of at least 40 mmHg as measured by a pressure test (PCT) after un-rolling of said collagen carrier
III. a sterility assurance level (SAL) of $10^{-6}$.

Still another aspect of the invention relates to a rolled compressed collagen carrier according to the invention for use in tissue sealing, tissue gluing and haemostasis.

Yet another aspect of the invention relates to a rolled compressed collagen carrier according the invention for use in minimally invasive surgery.

Another aspect of the invention relates to a rolled compressed collagen carrier according to the invention for use in endoscopic surgery.

A further another aspect of the invention relates to an unrolled rolled compressed collagen carrier according to the invention for use in tissue sealing, tissue gluing and haemostasis.

Another aspect of the invention relates to an unrolled rolled compressed collagen carrier according to the invention for use in minimally invasive surgery.

An aspect of the invention relates to an unrolled rolled compressed collagen carrier according the invention for use in endoscopic surgery.

Still another aspect of the invention relates to an unrolled at least partly mechanically rolled compressed collagen carrier according to the invention for use in tissue sealing, tissue gluing and haemostasis.

Yet another aspect of the invention relates to an unrolled at least partly mechanically rolled compressed collagen carrier according to the invention for use in minimally invasive surgery.

An aspect of the invention relates to an unrolled at least partly mechanically rolled compressed collagen carrier according to the invention for use in endoscopic surgery.

Another aspect of the invention relates to a rolled compressed collagen carrier according to the invention for use in the prevention or treatment of tissue in need of sealing and/or gluing.

An aspect of the invention relates to a rolled compressed collagen carrier according to the invention for use in the prevention or treatment of bleeding in tissue in need of haemostasis.

A further aspect of the invention relates to a rolled compressed collagen carrier according to the invention for use in the prevention or treatment of injury associated with performing minimally invasive surgery.

Still another aspect of the invention relates to a rolled compressed collagen carrier according to the invention for use in the prevention or treatment of injury associated with performing endoscopic treatment, laparoscopy treatment, or thoracoscopy treatment.

Still further aspects of the present invention relates to a process for coiling a collagen carrier, the collagen carrier comprising (i) a collagen layer and (ii) a coating layer preferably comprising fibrinogen and thrombin, said process comprising the sequential steps of:
humidifying at least part of said collagen carrier,
coiling said collagen carrier
drying the coiled collagen carrier,
thereby providing a form-stable coiled collagen carrier.

BRIEF DESCRIPTION OF THE FIGURES

FIG. 9 shows a wipe moistened with saline held by forceps, used for moulding the TachoSil® product onto the application site, and a swab moistened with saline is used in cases where a wipe is insufficient and additional wetting and compression is required.

In the figures, same features are labeled with identical numerals—refer e.g. to the detailed description of FIG. 11 for the numerals.

Figure 1:
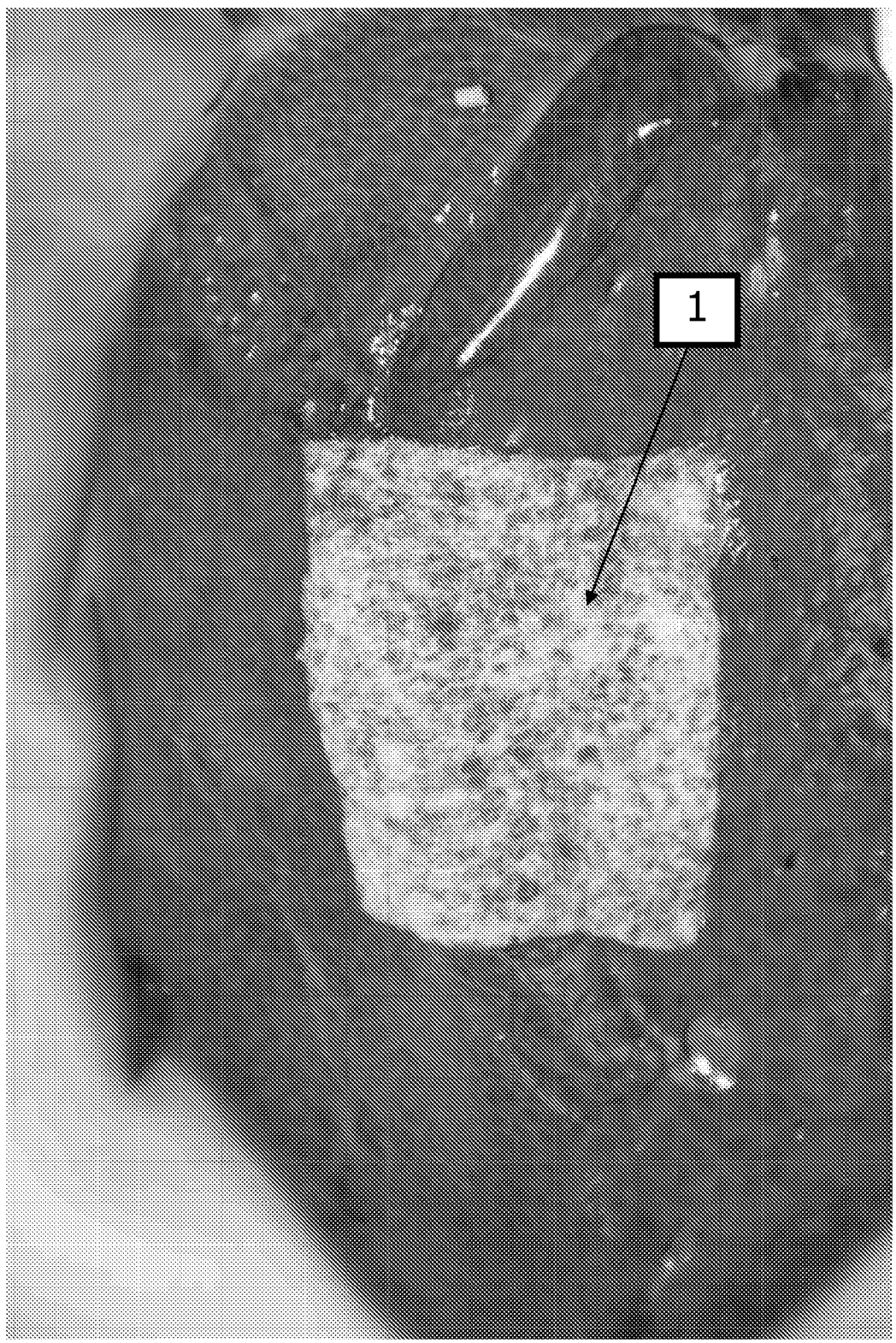
FIG. 1 shows adherence of a collagen carrier (in uncoiled state) of the present invention on a piece of liver tissue (see description in Example 2).

The present invention will now be described in more detail in the following.

DETAILED DESCRIPTION OF THE INVENTION

Definitions

Prior to discussing the present invention in further details, the following terms and conventions will first be defined:

The term "collagen carrier" is in the present context any suitable carrier comprising collagen that can have a coating layer that comprises/consist of a collagen layer and/or a coating layer. The collagen carrier can in one embodiment be rolled or coiled (the words "rolled" and "coiled" are used interchangeably herein). The collagen carrier can in another embodiment be in an unrolled or uncoiled state after coiling, i.e. as an unrolled or uncoiled collagen carrier (the terms "unroll" or "uncoil" are used interchangeably herein). The coiled collagen carrier of the present invention can in one embodiment be a compressed, coiled collagen carrier, or in another embodiment an unrolled version of a compressed, coiled collagen carrier. Preferably, the collagen carrier is a collagen sponge comprising or consisting essentially of collagen type I fibres and a coating. Although the carrier material is preferably a collagen sponge which comprises collagen type I material from mammalian, transgenic or recombinant sources, it can also comprise another type of collagen, for example one or more of collagen type I, II, III, IV, VII and/or X. Preferably the collagen carrier, such as a collagen sponge, is coated with the human coagulation factors fibrinogen and thrombin and optionally also riboflavin (a yellow colouring agent used to aid in identifying the active side of the collagen carrier). Thus in one embodiment of the present invention, the collagen carrier is a collagen sponge consisting essentially of collagen type I fibres and a coating of fibrinogen, thrombin and riboflavin. Fibrinogen and thrombin can for example be human fibrinogen and thrombin, and can be purified from a natural source, or can alternatively be e.g. transgenic or recombinant human fibrinogen and thrombin, or can be manufactured by other methods such as e.g. chemical synthesis. Fibrinogen and thrombin are preferably solid or mostly solid and in one embodiment can be human of origin. In another embodiment, at least one and more preferably both of the components fibrinogen and thrombin have the human amino acid sequence and can be produced by recombinant technology, inclusion bodies or chemical synthesis. The thrombin and fibrinogen are in one embodiment dry, such as containing less than 5% water, such as less than 4% water, such as less than 3% water, such as less than 2% water, such as less than 1% water, such as less than 0.8% water, such as less than 0.6% water, such as less than 0.4% water, such as less than 0.2% water, such as less than 0.1% water.

In one embodiment of the present invention, the collagen carrier comprises or consists of (i) a collagen layer and (ii) a coating layer comprising fibrinogen and optionally a colouring agent such as e.g. riboflavin. The collagen carrier may in an embodiment further comprise other peptides, such as other peptides capable of causing haemostasis.

In one embodiment of the present invention, the expressions collagen sponge, collagen fleece, collagen patch or simply fleece or patch are terms that are used synonymously to mean a collagen carrier. A carrier may alternatively to collagen comprise a biodegradable co-polymer or a polymer such as a polyhyaluronic acid, polyhydroxy acid, e. g. lactic acid, glucolic acid, hydroxybutanoic acid, a cellulose, or gelatine. Another alternative carrier may be polyglactin 910, i.e. a synthetic, adsorbable copolymer of 90% glycolide ($C_2H_2O_2$) and 10% lactide ($C_6H_8O_4$); such as e.g. with molecular formula $(C_2H_2O_2)_m$ and $(C_3H_4O_2)_n$. A further alternative carrier may be equine collagen, such as e.g. native equine collagen extracted from sinews.

Thus, the collagen part of the collagen carrier can in one embodiment of the present invention be substituted with a non-collagen matrix that is coated in the same way as for the collagen carrier as described herein, i.e. in one embodiment of the present invention is provided a carrier comprising or consisting of a non-collagen matrix coated with a coating comprising or consisting of fibrinogen and thrombin. One example of a suitable non-collagen matrix is a cellulose fabric. In one embodiment of the present invention, the non-collagen matrix is an oxidized regenerated cellulose fabric sheet attached to a non-woven polyglactin 910 felt.

However, it is preferably a collagen carrier preferably having a shape suitable for a medicated sponge. In an embodiment of the invention, the collagen carrier which is to undergo the coiling process of the present invention is identical to Tachosil® or TachoComb® available from Nycomed, such as described in WO 02/058 749, WO 02/070 594 and WO 02/058 750.

A preferred collagen layer is preferably used to mean a collagen sponge produced by the method according to the invention as disclosed in WO 02/070594. The collagen layer used in the present invention preferably fulfills at least one, such as at least two or at least three, of the following criteria:
pH-value between 5.0 and 6.0,
lactic acid content at the most 5%,
ammonium content at the most 0.5%,
soluble protein content, calculated as albumin content, at the most 0.5%,
sulphate ashes content at the most 1.0%,
heavy metal content at the most 20 ppm,
microbiological purity, at the most 103 CFU/g,
collagen content of 75% to 100%,
density of 1-10 mg/cm$^3$, such as 2-7 mg/cm$^3$,
elasticity module of 5-100 N/cm$^2$, such as 10-50 N/cm$^2$, and wherein when isolating parts of the sponge, the sponge will have the following properties:
elasticity module in the range of 5 to 100 N/cm$^2$,
density in the range of 1 to 10 mg/cm$^3$,
chamber diameter of more than 0.75 mm and less than 4 mm, or a chamber diameter average of at most 3 mm.

Please note that the density of a collagen carrier is the density of the collagen carrier excluding the coating layer.

Preferably the collagen layer fulfills at least the following:
pH-value between 5.0 and 6.0,
lactic acid content at the most 5%,
ammonium content at the most 0.5%,
soluble protein content, calculated as albumin content, at the most 0.5%,
sulphate ashes content at the most 1.0%,
heavy metal content at the most 20 ppm,
microbiological purity, at the most 103 CFU/g,
collagen content of 75% to 100%,
density of 1-10 mg/cm$^3$, such as 2-7 mg/cm$^3$.

Further, the collagen layer is air and liquid tight in the sense that, once the collagen sponge is applied to a wound, it will not allow air or liquid to pass through the collagen layer. Liquids are absorbed in the layer. This effect is primarily achieved due to the fact the collagen layer has a three-dimensional structure with stacked chambers separated and substantially totally enclosed by walls of collagen material, in contradiction to known collagen sponges which have a fibre structure.

In the present context, the term "chamber diameter" should be understood as the largest straight-line wall-to-wall distance in a chamber, i. e. as the largest diagonal straight-line distance of a chamber. The chambers may be of a polygonal shape, such as of an octagonal shape. Thus, when the carrier is cut, the chambers are divided and cut to caverns.

It has been found that a chamber diameter of more than 0.75 mm and less than 4 mm, or a chamber diameter average of at most 3 mm, renders the collagen sponge particularly useful for being coated with a fibrin glue preparation. When the carrier is cut, the chambers are divided and cut to caverns. The preferably solid fibrinogen and the preferably solid thrombin is fixed to the collagen layer and most of it is present in the caverns thus providing a substantially even distribution of the preferably solid thrombin and preferably solid fibrinogen. Due to this and the fixation, it is possible to introduce substantial amounts of fibrinogen and thrombin on the carrier in contrast to the situation where liquid compositions of thrombin and fibrinogen are e. g. dropped or sprayed onto the material.

Each coated collagen carrier as well as the uncoated collagen layer is inspected visually for the "pore size distribution"—no pores wider than 4 mm and deeper than 2 mm are allowed. These sizes are measured with a ruler if necessary.

By fixation of the coating layer to the collagen layer is preferably meant that the coating layer adheres through mechanical interactions i.e. by inclusion onto the collagen carrier pore surface and within the coating layer.

In a preferred embodiment of the present invention, the amount of fibrinogen and thrombin/cm$^2$ in the coating layer can be:
Thrombin 1.3-2.7 IU/cm$^2$ and/or
Fibrinogen 3.6-7.4 mg/cm$^2$ In an embodiment, the above mentioned amounts of fibrinogen and thrombin/cm$^2$ are identical to Tachosil® or TachoComb® available from Nycomed, such as described in WO 02/058 749, WO 02/070 594 and WO 02/058 750.

By substantially even distribution of the solid thrombin and solid fibrinogen is meant that the coating layer is substantially evenly distributed across the collagen layer meaning that local changes in thickness of the coating layer is observed visually by SEM cross sections i.e. the coating layer may be located on the surface and sometimes at a lower level in an open cell. There should not be any through-going cracks (fissures) on the coating layer.

In an embodiment a collagen carrier according to the present invention may have a size of 92-98 mm*46-50 mm*4-7 mm and this carrier is called a large size collagen carrier and has the shape of a box of rectangular cross-section with all sides flat. Hence, the area of the largest rectangular cross-section is about 42.3-49.0 cm$^2$. In another embodiment a midi size collagen carrier according to the present invention is 46-49 mm*46-50 mm*4-7 mm, and has the shape of a square box of quadrant cross-section. Hence, the area of the quadrant cross-section is about 21.2-24.5 cm$^2$. A midi size collagen carrier according to the invention is preferred. In yet another embodiment a mini size collagen carrier according to the invention is 28-33 mm*23-27 mm*4-7 mm, and has the shape of a box of rectangular cross-section with all sides flat. Hence, the area of the largest rectangular cross-section is about 6.4-8.9 cm$^2$.

In an embodiment of the invention, a collagen carrier has at least one of the following physical properties, such as at least two of the following physical properties, such as at least three of the following physical properties, such as at least four of the following physical properties: elasticity module in the range of 5-100 N/cm$^2$, density of 1-10 mg/cm$^3$, chamber diameter of more than 0.75 mm and less than 4 mm and/or having a chamber diameter average below 3 mm and evenly distributed and fixed upon said collagen carrier solid fibrinogen and solid thrombin. Please note that the density of a collagen carrier is the density of the collagen carrier excluding the coating layer.

According to the invention, a collagen carrier may become manipulated e.g. such as by manual and/or mechanical manipulation (i.e. humidification, compression, rolling, unrolling, and passage through an access orifice, such as a trocar) resulting in various different manipulated collagen carriers such as:
1. A humidified collagen carrier
2. A compressed collagen carrier, optionally a humidified compressed collagen carrier
3. A rolled collagen carrier, optionally a humidified rolled collagen carrier
4. A rolled compressed collagen carrier, optionally a humidified rolled compressed collagen carrier
5. An at least partly mechanically humidified collagen carrier
6. An at least partly mechanically compressed collagen carrier, optionally an at least partly mechanically humidified compressed collagen carrier 7. An at least partly mechanically rolled collagen carrier, optionally an at least partly mechanically humidified rolled collagen carrier
8. An at least partly mechanically rolled compressed collagen carrier, optionally an at least partly mechanically humidified rolled compressed collagen carrier It should be noted that all aspects relating to collagen carriers as mentioned above also apply to an at least partly mechanically prepared collagen carriers.

The term "mechanically" is meant to refer to any non-manual way of producing, obtaining or providing a medicated sponge, such as a rolled and/or compressed collagen carrier of the present invention by way of an at least semiautomatic process, such as a fully automatic process.

"Mechanically stable" is meant to refer to "form-stable".

Form-stable as used in form-stable coiled collagen carrier is preferably used to mean a coiled collagen carrier which maintains its geometrical shape without being fixated by constraining or constriction elements not forming part of the collagen carrier. For example, a form-stable coiled collagen carrier may maintain its geometrical shape because the coating layer and/or the collagen layer has no tension acting to distort—such as uncoil—the coiled collagen carrier. A further characteristic of form-stable is that the coiled collagen carrier may be elastic deformed and revert to the shape it had before being elastic deformed by the releasing the tension provided by the elastic deformation. A furthermore characteristic of a form-stable coiled collagen carrier is that it is preferably hardened in the coiled shape.

Solid as used e.g. solid fibrinogen and solid thrombin is used in a manner being ordinary to the skilled person to mean a material in solid state. Mostly solid is preferably used to that a minor fraction of the material in question may be in a state being different from solid state (such as less than 5%, such as less than 3%, preferably less than 1%, such as less than 0.5%). Alternatively, mostly solid is preferably used to mean that the material in question may contain liquid, such as less than 5% liquid, or less than 1% liquid.

The term "manual" is meant to refer to any manual way of producing, obtaining or providing a carrier, such as medicated sponge or such as a rolled and/or compressed collagen carrier of the present invention. Thus, by "manual" is meant any way in which at least one step of the production method (for example, the rolling step and/or the compression step) is carried out using at least one human hand(s), for example rolling the collagen fleece round a "pin" by hand or compressing the collagen fleece using hand power, for example compressing the fleece directly by application of one or more human hands. In a preferred embodiment of the present invention, at least the rolling step and/or the compression step are not carried out manually, i.e. are not carried out by using human hand(s). Thus in a preferred embodiment of the present invention, the collagen fleece is not rolled around an object (such as a pin) by hand and/or the collagen fleece is not compressed by the application of at least one human hand.

The term "at least partly mechanically prepared/manipulated is meant to mean a process wherein at least a part of a process step is performed mechanically e.g. when a collagen carrier is compressed mechanically but the collagen carrier is placed by hand into the compressing device such as through a set of rollers for roller compaction.

By the term "rolling" is meant any well known process for rolling an object i.e. by hand, mechanically or by a combination thereof.

Coiling as used e.g. in coiling said collagen carrier is preferably used to mean the process of winding the collagen carrier into an element preferably having spiral shaped cross sections. The coiled collagen carrier may have an S-shaped core.

In one embodiment according to the invention, when a collagen carrier is mechanically rolled, the process for rolling comprises the steps of gripping at least one outer edge of a collagen carrier by using at least one gripping device, such as tweezers, such as mechanical fingers, and coiling said at least one gripping device around its centre axis and thereby also coiling said collagen carrier, and releasing said mechanically rolled collagen carrier from said at least one gripping device. The process for rolling a collagen carrier according to the invention also comprises rolling preferably a compressed collagen carrier, such as an at least partly mechanically compressed collagen carrier, such as a humidified collagen carrier, such as a humidified compressed collagen carrier. Hence, the rolling can be applied to any collagen carrier, such as a medicated sponge, which is used directly without being previously exposed to one or more physical manipulations such as e.g. humidification, compression, elevated room temperature and humidity or gamma radiation. Preferably, the rolling process can be applied to any collagen carrier which has been previously exposed to one or more of said physical manipulations. In the present context the words to roll, spool, rotate or spin are used interchangeably.

By the term "compressed collagen carrier" is preferably meant a compressed collagen carrier, which has been subjected to an evenly distributed pressure (i.e. compression) to achieve the following physical properties: a coating comprising solid fibrinogen and solid thrombin that is evenly distributed and fixed upon said collagen carrier, and having at least one of the following physical properties in the unrolled state:

I. a thickness of at the most 4 mm
II. an adhesive strength of at least 40 mmHg as measured upon un-rolling by a pressure test (PCT)
III. a sterility assurance level (SAL) of $10^{-6}$.

In one embodiment of the present invention, said compressed collagen carrier has optionally been humidified either before or optionally after the compression step to at least one side of said collagen carrier. Said compressed collagen carrier has optionally been at least partly mechanically processed.

By the term "compressing" is meant the process for compressing an object such as a collagen carrier and it refers in the present context to the process when the collagen carrier when being compressed is subjected to an evenly distributed pressure. The words compression or compaction are used interchangeably. Likewise, the expressions explaining that an object can be compressed, pressed or compacted are used interchangeably herein. The collagen carrier can e.g. become compressed when it passes through a set of rollers using a certain gap size. The collagen carrier being pressed is preferably a humidified collagen carrier or a non-humidified collagen carrier. The use of a roller compactor is preferred (mechanical compression). Hence, a compression can be made by any conventional manual or mechanical way of compressing an object by subjecting it to an evenly distributed pressure i.e. preferably by passing it through a set of rollers by roller compaction, by placing the carrier between two sets of even/flat plates where the top plate is a plunger, or rolling a cylindrical object over said carrier which is placed on a flat, even bottom plate.

The expression "gap size" refers in the present context to the shortest distance measured in mm between the rollers in a roller compactor. Preferably, the compression is performed by roller compaction using a gap size between the rollers of no more than 0.30 mm, such as no more than 0.35 mm, such as no more than 0.40 mm, such as no more than 0.45 mm, such as no more than 0.50 mm, such as no more than 0.55, such as no more than 0.60 mm, such as no more than 0.65 mm, such as no more than 0.70 mm, such as preferably no more than 0.75 mm, such as no more than 0.80 mm, such as no more than 0.85 mm, such as no more than 0.90 mm, such as no more than 0.95 mm and such as no more than 1.00 mm. Using a gap size between the rollers of about 0.45-0.75 mm is preferred, such as about 0.45-0.70 mm, such as about 0.45-0.65 mm, such as about 0.45-0.60 mm, such as about 0.45-0.55 mm, such as about 0.45-0.50 mm, such as about 0.50-0.75 mm, such as about 0.55-0.75 mm, such as about 0.60-0.75 mm, such as about 0.65-0.75 mm, such as about 0.70-0.75 mm, such as about 0.50-0.70 mm, such as about 0.50-0.65 mm, such as about 0.50-0.60 mm, such as about 0.60-0.70 mm, such as about 0.60-0.65 mm. A gap size of about 0.40 mm results in a harsh/strong compression, whereas a gap size of about 0.75 mm results in a gentle compression.

Preferably, the rollers performing said roller compaction have a diameter of about 100 mm, such as about 80 mm, such as about 70 mm, such as about 38-62 mm, such as about 43-57 mm, such as preferably about 48-52 mm. Said rollers are preferably made out of an inflexible and inert material which does not transfer roller material to said compressed collagen carriers upon compaction, i.e. the surface of the rollers are important. In an embodiment, the rollers are polished.

In one embodiment, the term "rolled collagen carrier" preferably is a rolled collagen carrier characterized by the following physical properties: a coating comprising solid fibrinogen and solid thrombin that is evenly distributed and fixed upon said collagen carrier, and having at least one of the following physical properties:
  I. a diameter of at the most 10 mm
  II. an adhesive strength of at least 40 mmHg as measured upon un-rolling by a pressure test (PCT)
  III. a sterility assurance level (SAL) of $10^{-6}$.

For example, the rolled collagen carrier can have a diameter of at the most 12 mm, such as at the most 11 mm, such as at the most 10 mm, for example at the most 8 mm, such as at the most 6 mm, for example at the most 4 mm, together with an adhesive strength of at least 30 mm Hg, such as at least 35 mmHg, such as preferably 40 mmHg as measured upon un-rolling by a pressure test (PCT), and optionally a sterility assurance level (SAL) of $10^{-6}$.

It should be noted that the rolled collagen carrier may optionally have been humidified prior to becoming rolled to at least one side of said collagen carrier (i.e. the carrier has been rolled after being humidified on at least one side), preferably to the front side comprising said coating resulting in a rolled collagen carrier having the coating externally oriented. Said rolled collagen carrier has optionally been at least partly mechanically processed, optionally also at least partly mechanically humidified.

By the term "rolled compressed collagen carrier" is meant a rolled compressed collagen carrier characterized by the following physical properties: a coating comprising solid fibrinogen and solid thrombin that is evenly distributed and fixed upon said collagen carrier, and having at least one of the following physical properties:
  I. a diameter of at the most 10 mm
  II. an adhesive strength of at least 40 mmHg as measured upon un-rolling by a pressure test (PCT)
  III. a sterility assurance level (SAL) of $10^{-6}$.

It should be noted that said rolled compressed collagen carrier may optionally have been humidified prior to becoming compressed and/or optionally at least partly mechanically rolled.

Thus, an advantage of the invention is that said rolled compressed collagen carrier is ready to use in minimally invasive surgery, such as ready to be inserted into endoscopic devices.

By the term "mechanically rolled compressed collagen carrier" is meant a collagen carrier that has been mechanically compressed and thereafter mechanically rolled and which is characterized by the following physical properties: a coating comprising solid fibrinogen and solid thrombin that is evenly distributed and fixed upon said mechanically rolled compressed collagen carrier, and having at least one of the following physical properties:
  I. a diameter of at the most 10 mm
  II. an adhesive strength of at least 40 mmHg as measured upon un-rolling by a pressure test (PCT)
  III. a sterility assurance level (SAL) of $10^{-6}$.

Optionally, said mechanically rolled compressed collagen carrier has been mechanically humidified during processing.

By the term "humidifying or humidification" is meant the process of humidifying/moisturizing at least part of a collagen carrier with at least one liquid solvent to preferably at least one side of said carrier which has at least one side coated with a coating comprising biologically active substances. If more than one side of the carrier is coated with a coating comprising biologically active substances, then the term may comprise humidifying such as at least two sides, such as at least three sides, such as at least four sides, such as at least five sides, such as all sides of said collagen carrier. The humidified side is preferably the side comprising a coating, but it may also be a side that does not comprise a coating.

Humidifying as used in e.g. humidifying at least a part of said collagen carrier is preferably also used to mean the step of applying a liquid substance to a collagen carrier.

Thus, the term "humidified collagen carrier" is meant to mean a collagen carrier that has been exposed to at least one liquid solvent to preferably at least one side of said carrier, such as at least two sides, such as at least three sides, such as at least four sides, such as at least five sides, such as all sides, to achieve a humidified collagen carrier.

In one embodiment of the present invention the collagen carrier is preferably humidified on at least one side of said carrier (i.e. the front) which has at least one side coated with a coating comprising biologically active substances before being compressed and/or before being rolled. The words humidified and moisturized are used interchangeably. In another embodiment it is preferred to humidify both the front and back of a collagen carrier of the present invention, wherein the front comprises said coating. Said humidified collagen carrier has optionally been at least partly mechanically processed.

In an embodiment of the present invention said humidified collagen carrier has a coating comprising solid fibrinogen and solid thrombin that is evenly distributed and fixed upon said collagen carrier, and having at least one of the following physical properties:
  I. a diameter of at the most 10 mm
  II. an adhesive strength of at least 40 mmHg as measured upon un-rolling by a pressure test (PCT)
  III. a sterility assurance level (SAL) of $10^{-6}$.

By the term "solvent" is meant any suitable solvent such as physiological saline, purified water, aqueous vapour or any suitable organic solvent such as ethanol, dehydrated ethanol with a maximum content of 0.1% water, isopropanol or methanol. An alcohol is selected from the group consisting of ethanol, dehydrated ethanol with a maximum content of 0.1% water, 1-propanol, 2-propanol, 2-methyl-2-propanol, ethylene glycol, 1-butanol, 2-butanol or any combination thereof. In an embodiment a solvent is selected from ethanol, dehydrated ethanol with a maximum content of 0.1% water, isopropanol, 1-propanol, 2-methyl-2-propanol, water or any combination thereof. In a further embodiment, a solvent is selected from ethanol, dehydrated ethanol with a maximum content of 0.1% water, isopropanol, water or combinations thereof. In a embodiment the ethanol is dehydrated ethanol with a maximum content of 0.1% water. In one embodiment of the applied solvent, the amount of applied solvent is about 0.8-10.75 mg/cm$^2$ collagen carrier, such as about 1.2-10.75 mg/cm$^2$ collagen carrier, such as about 0.8-10.4 mg/cm$^2$ collagen carrier, such as about 0.8-6.1 mg/cm$^2$ collagen carrier, such as about 1.2-4.7 mg/cm$^2$ collagen carrier, such as about 2.85-4.24 mg/cm$^2$. An alcohol—preferably ethanol—is a preferred solvent. In an embodiment, the solvent essentially consist of a mixture of ethanol or dehydrated ethanol with a maximum content of 0.1% water and water or isopropanol and water, wherein the amount of water is up to 20%, such as up to 18%, such as up to 16%, such as up to 14%, such as up to 12%, such as up to 10%, such as up to 8%, such as up to 6%, such as up to 5%, such as up to 4%, such as up to 3%, such as 2.4%, such as up to 2%, such as up to 1.5%, such as up to 1%, such as up to 0.5%. The solvent may also contain fibrinogen and/or thrombin and/or albumin and/or some salt. In a further embodiment, ethanol or dehydrated ethanol with a maximum content of 0.1% water is the preferred solvent and is used in an amount of about 9 mg ethanol/cm$^2$ collagen carrier, such as about 8 mg ethanol/cm$^2$ collagen carrier, such as about 7 mg ethanol/cm$^2$ collagen carrier, such as about 6 mg ethanol/cm$^2$ collagen carrier, such as about 5 mg ethanol/cm$^2$ collagen carrier, such as about 4 mg ethanol/cm$^2$ collagen carrier, such as about 3 mg ethanol/cm$^2$ collagen carrier, such as about 2 mg ethanol/cm$^2$ collagen carrier, such as about 1.2 mg ethanol/cm$^2$ collagen carrier, such as about 1 mg ethanol/cm$^2$ collagen carrier, such as about 0.5 mg ethanol/cm$^2$ collagen carrier.

Without being bound by theory, it is speculated that using more than about 10.75 mg ethanol or dehydrated ethanol with a maximum content of 0.1% water/cm$^2$ collagen carrier, such as about 10.4, mg ethanol/cm$^2$ collagen carrier could make said collagen carriers become sticky when being compressed. Hence, using an ethanol level of no more than 10.75 mg ethanol/cm$^2$ collagen fleece is preferred.

By the term "relative humidity (RH)" is meant the amount of water vapor in a mixture of air and water vapor.

In an embodiment, the process according to the present invention is performed at 10-75% RH, such as 30-50% RH, such as 30-60%, such as 30-64% RH, such as 30-65% RH, such as 30-70% RH, such as 40-60% RH, such as 40-64% RH, such as 40-70% RH and optionally at a temperature of 5-30° C., such as 18-22° C., such as 18-25° C. In a preferred embodiment, RH is 30-50% and the temperature is 18-22° C. which is the preferred relative humidity range and temperature range of the room (e.g. manufacturing facility) where the rolled and/or compressed collagen carriers are processed. See further below when the term "drying" is defined. In another embodiment the relative humidity range and temperature of the room (e.g. manufacturing facility) where the rolled and/or compressed collagen carriers are processed is about 25° C. and 64-70% RH.

By the term "elasticity module" is meant the tendency of an object to be deformed elastically i.e., non-permanently when a force is applied to it. In the present context the elasticity module is used to describe the elasticity of a collagen carrier of the present invention. The elasticity module is in the present invention measured in N/cm$^2$. The elasticity module is preferably 5-100 N/cm$^2$, such as 15-90 N/cm$^2$, such as 25-80 N/cm$^2$, such as 35-70 N/cm$^2$, such as 45-60 N/cm$^2$, such as 50-55 N/cm$^2$. The elasticity module is a well known parameter in the art to measure elasticity, as disclosed in e.g. the book by J. E. Gordon, The New Science of Strong Materials or Why You Don't Fall Through the Floor page 38-43 and EP 1 053 757 B1. Elasticity module thus represents the elastic flexibility of a material, the flexibility of any given object.

By "elasticity module" is meant Youngs module, E, the physical constant, characterized by the stiffness of an elastic material. E is force (N) divided with area (mm$^2$), written as N/mm$^2$ or MPa.

By the term "density" or the mass density of a material is meant the material's mass per unit volume. The symbol most often used for density is p but in the present context, density is defined as weight per unit volume mg/cm$^3$, which is also called specific weight. The method and the equipment used for determining the density are disclosed in further detail in the example section below. The density of a collagen carrier according to the present invention is the density of the collagen carrier excluding the coating layer. In an embodiment of the present invention, the density of the collagen carrier before humidification and/or rolling and/or compression, such as for the collagen carrier provided in step (a) of the present invention, is in the range of 1-10 mg/cm$^3$, such as in the range of 1-9 mg/cm$^3$, such as in the range of 1-8 mg/cm$^3$, such as in the range of 1-7 mg/cm$^3$, such as in the range of 1-6 mg/cm$^3$, such as in the range of 1-5 mg/cm$^3$, such as in the range of 1-4 mg/cm$^3$, such as in the range of 1-3 mg/cm$^3$, such as in the range of 1-2 mg/cm$^3$, such as in the range of 2-9 mg/cm$^3$, such as in the range of 2-8 mg/cm$^3$, such as in the range of 2-7 mg/cm$^3$, such as in the range of 2-6 mg/cm$^3$, such as in the range of 2-5 mg/cm$^3$, such as in the range of 2-4 mg/cm$^3$, such as in the range of 3-9 mg/cm$^3$, such as in the range of 3-8 mg/cm$^3$, such as in the range of 3-7 mg/cm$^3$, such as in the range of 3-6 mg/cm$^3$, such as in the range of 3-5 mg/cm$^3$, preferably such as in the range of 3.0-4.5 mg/cm$^3$, such as in the range of 3.0-4.4 mg/cm$^3$, such as in the range of 3.0-4.3 mg/cm$^3$, such as in the range of 3.0-4.2 mg/cm$^3$, such as in the range of 3.0-4.1 mg/cm$^3$, such as in the range of 3.0-4.0 mg/cm$^3$, such as in the range of 3.0-3.9 mg/cm$^3$, such as in the range of 3.0-3.8 mg/cm$^3$, such as in the range of 3.0-3.7 mg/cm$^3$, such as in the range of 3.0-3.6 mg/cm$^3$, such as in the range of 3.0-3.5 mg/cm$^3$, such as in the range of 3.0-3.4 mg/cm$^3$, such as in the range of 3.0-3.3 mg/cm$^3$, such as in the range of 3.0-3.2 mg/cm$^3$, such as in the range of 3.0-3.1 mg/cm$^3$, such as in the range of 3.1-4.5 mg/cm$^3$, such as in the range of 3.2-4.5 mg/cm$^3$, such as in the range of 3.3-4.5 mg/cm$^3$, such as in the range of 3.4-4.5 mg/cm$^3$, such as in the range of 3.5-4.5 mg/cm$^3$, such as in the range of 3.6-4.5 mg/cm$^3$, such as in the range of 3.7-4.5 mg/cm$^3$, such as in the range of 3.8-4.5 mg/cm$^3$, such as in the range of 3.9-4.5 mg/cm$^3$, such as in the range of 4.0-4.5 mg/cm$^3$, such as in the range of 4.1-4.5 mg/cm$^3$, such as in the range of 4.2-4.5 mg/cm$^3$, such as in the range of 4.3-4.5 mg/cm$^3$, such as in the range of 4.4-4.5 mg/cm$^3$.

The density of a humidified and/or compressed and/or rolled collagen carrier of the present invention is preferably in the range of 1-15 mg/cm$^3$, such as in the range of 2-15 mg/cm$^3$, such as in the range of 3-15 mg/cm$^3$, such as in the range of 4-15 mg/cm$^3$, such as in the range of 5-15 mg/cm$^3$, such as in the range of 6-15 mg/cm$^3$, such as in the range of 7-15 mg/cm$^3$, such as in the range of 8-15 mg/cm$^3$, such as in the range of 9-15 mg/cm$^3$, such as in the range of 10-15 mg/cm$^3$, such as in the range of 11-15 mg/cm$^3$, such as in the range of 12-15 mg/cm$^3$, such as in the range of 13-15 mg/cm$^3$, such as in the range of 14-15 mg/cm$^3$, such as in the range of 3-14 mg/cm$^3$, such as in the range of 3-12 mg/cm$^3$, such as in the range of 3-10 mg/cm$^3$, such as in the range of 3-9 mg/cm$^3$, such as in the range of 3-8 mg/cm$^3$, such as in the range of 3-7 mg/cm$^3$, such as in the range of 3-6 mg/cm$^3$, such as in the range of 3-5 mg/cm$^3$, such as in the range of 3.0-4.5 mg/cm$^3$, such as in the range of 3.0-4.4 mg/cm$^3$, such as in the range of 3.0-4.3 mg/cm$^3$, such as in the range of 3.0-4.2 mg/cm$^3$, such as in the range of 3.0-4.1 mg/cm$^3$, such as in the range of 3.0-4.0 mg/cm$^3$, such as in the range of 3.0-3.9 mg/cm$^3$, such as in the range of 3.0-3.8 mg/cm$^3$, such as in the range of 3.0-3.7 mg/cm$^3$, such as in the range of 3.0-3.6 mg/cm$^3$, such as in the range of 3.0-3.5 mg/cm$^3$, such as in the range of 3.0-3.4 mg/cm$^3$, such as in the range of 3.0-3.3 mg/cm$^3$, such as in the range of 3.0-3.2 mg/cm$^3$, such as in the range of 3.0-3.1 mg/cm$^3$, such as in the range of 3.1-4.5 mg/cm$^3$, such as in the range of 3.2-4.5 mg/cm$^3$, such as in the range of 3.3-4.5 mg/cm$^3$, such as in the range of 3.4-4.5 mg/cm$^3$, such as in the range of 3.5-4.5 mg/cm$^3$, such as in the range of 3.6-4.5 mg/cm$^3$, such as in the range of 3.7-4.5 mg/cm$^3$, such as in the range of 3.8-4.5 mg/cm$^3$, such as in the range of 3.9-4.5 mg/cm$^3$, such as in the range of 4.0-4.5 mg/cm$^3$, such as in the range of 4.1-4.5 mg/cm$^3$, such as in the range of 4.2-4.5 mg/cm$^3$, such as in the range of 4.3-4.5 mg/cm$^3$, such as in the range of 4.4-4.5 mg/cm$^3$.

The density of a humidified and/or compressed and rolled collagen carrier of the present invention is measured upon unrolling said rolled collagen carrier of the present invention. Please note that the density of a collagen carrier of the present invention is the density of the collagen carrier excluding the coating layer.

It is presently preferred to determine the density by weighing a collagen carrier of known volume, such as a rolled and/or compressed collagen carrier of a certain size (see the examples section), such as a large size collagen carrier (also called a strip or a fleece). The density is calculated by dividing the mass of the collagen carrier by the volume of the collagen carrier. The method and the equipment used for determining the density are disclosed in further detail in the example section below.

By the term "coating" is preferably meant a coating either comprising or essentially consisting of the biologically active substances fibrinogen and thrombin that are evenly distributed and fixed upon at least one side of a collagen carrier of the present invention, such as a rolled and/or compressed collagen carrier, such as an unrolled rolled and/or compressed collagen carrier. The coating may also include e.g. riboflavin (yellow color as marker of coated area). In one embodiment of the present invention, the active substances are preferably solid human fibrinogen, solid human thrombin and optionally solid riboflavin. Thus in one embodiment of the invention, the coating essentially consists of solid human fibrinogen, solid human thrombin and solid riboflavin. The coating is present on at least one side of the collagen carrier, such as a rolled and/or compressed collagen carrier, such as an unrolled rolled and/or compressed collagen carrier. Hence, in one embodiment the collagen carrier, such as a rolled and/or compressed collagen carrier, such as an unrolled rolled and/or compressed collagen carrier comprises one or more active sides wherein fibrinogen is present in an amount of 1.3-10 mg/cm$^2$, such as 2-10 mg/cm$^2$, such as 4.3-6.7 mg/cm$^2$, preferably about 3.6-7.4 mg/cm$^2$, such as about 5.5 mg/cm$^2$, and thrombin is present in an amount of 0.9-20 IU/cm$^2$, such as 0.9-15 IU/cm$^2$, such as 0.9-10 IU/cm$^2$, such as 1.0-5.5 IU/cm$^2$, preferably such as about 1.3-2.7 IU/cm$^2$, such as about 2.0 IU/cm$^2$. Said coating is preferably applied to at least one side of said collagen carrier, such as a rolled and/or compressed collagen carrier, such as an unrolled rolled and/or compressed collagen carrier.

When the collagen carrier, such as a rolled and/or compressed collagen carrier, such as an unrolled rolled and/or compressed collagen carrier, has a coating on one side of said carrier and when it is rolled the side coated with the biologically active substances can be externally oriented on said rolled collagen carrier, or the side coated with the biologically active substances can be internally oriented on the rolled collagen carrier. Presently, the first alternative is preferred for a rolled compressed collagen carrier of the present invention, i.e. external orientation of said coating.

Figure 3:
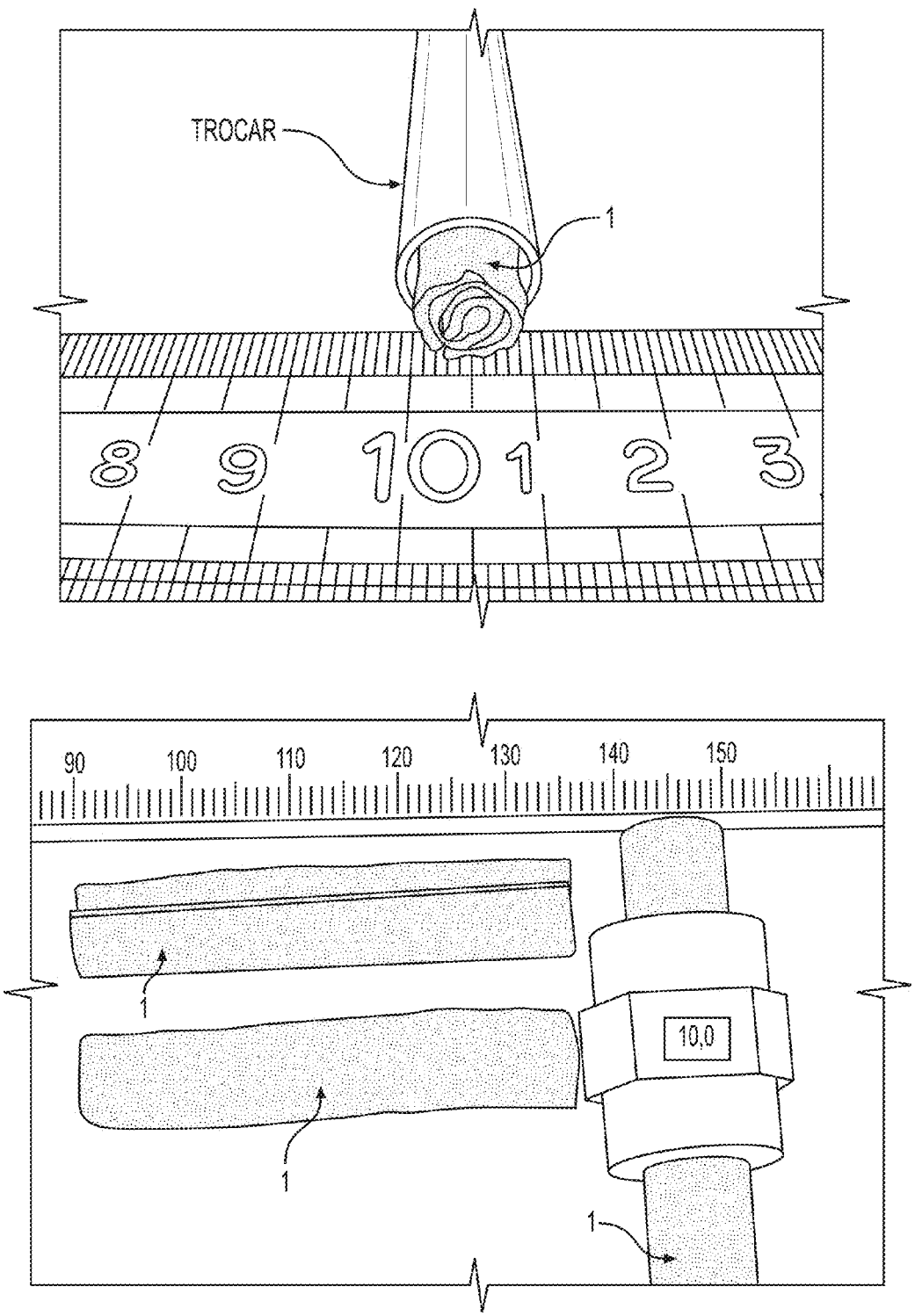
FIG. 3 shows pre-rolled collagen carriers according to the invention in a trocar besides a tape measure (upper picture). The lower picture shows the length and width of pre-rolled collagen carriers according to the invention. The fleeces are midi sized (batch 10419312 and 10431721).

By the term "diameter" of e.g. the rolled collagen carrier is meant the diameter of the cross section of any type of collagen carrier that has been rolled or coiled according to the present invention. Thus, the diameter of the resulting rolled collagen carrier as measured on the cross section (e.g. the shortest side) is about 5-12 mm, such as about 6-11, such as about 7-10 mm, such as about 8-9 mm, such as at the most 11 mm, preferably such as at the most 10 mm, preferably such as at the most 9 mm, such as at the most 8 mm, such as at the most 7 mm, such as at the most 6 mm, such as at the most 5 mm, such as at the most 4.5 mm, such as at the most 4 mm, such as at the most 3.5 mm, such as at the most 3 mm, such as at the most 2.5 mm, such as at the most 2.0 mm, such as at the most 1.5 mm, such as at the most 1.0 mm. The preferred diameter is less than 10 mm for midi sized fleeces, i.e. midi sized fleeces have the dimensions 46-49 mm*46-50 mm*4-7 mm. In FIG. 3 the length and width of a pre-rolled collagen carriers according to the invention is shown.

By the term "thickness" is meant the shortest measurable distance across any collagen carrier of the invention that is unrolled or nonrolled, which means that the thickness depends on whether the collagen carrier has been previously rolled or not and/or whether it has been previously compressed, humidified or not. When the term thickness is used to describe any type of unrolled or nonrolled collagen carrier according to the present invention the thickness is meant to mean the thickness which is about 1-10 mm, such as about 2-8, such as about 4-6, such as at the most 10 mm, such as at the most 9 mm, such as at the most 8 mm, such as at the most 7 mm, such as at the most 6 mm, such as at the most 5 mm, such as at the most 4 mm, such as at the most 3 mm, such as at the most 2 mm, such as at the most 1 mm. In an embodiment the preferred thickness of a collagen carrier is 4-7 mm. In another embodiment, the preferred thickness of an unrolled collagen carrier is at the most 4 mm.

By the term "adhesive strength" is meant the capability of a collagen carrier, such as a rolled and/or compressed collagen carrier, to adhere to living tissue and thus adhesive strength reflects the pharmaceutical activity of a collagen carrier according to the invention i.e. the capability of a collagen carrier, such as a rolled and/or compressed collagen carrier to provide tissue sealing, tissue gluing and haemostasis. Adhesive strength can be measured by an in vitro measurement such as the PCT test, and has the unit mmHg. The PCT test is described in example 4. The adhesive strength of a collagen carrier, such as a rolled and/or compressed collagen carrier can be measured using various pressure test methods that overall investigate how much pressure a sample/medical device can withstand before rupture/burst. Thus, these methods are used for determining adhesive strength/sealing of a patch, such as a medicated sponge, preferably such as a collagen carrier, such as a rolled and/or compressed collagen carrier according to the present invention. Hence, these methods simulate the adhesive strength/sealing capability of a medicated sponge in a living organism such as a mammal, e.g. rat, dog or human undergoing a surgery such as minimally invasive surgery. These methods comprise methods known to a person skilled in the art, such as e.g. Hydraulic Burst Leak Test (HBLT) (Crescent Design), such as ATC's Pressure Burst Tester (ATC Inc.), such as Evolution Hydraulic Burst Tester (AE Solutions, Inc.). In the present context, a pressure test called "PCT" is used to simulate in vitro adhesive strength of a collagen carrier, such as a rolled and/or compressed collagen carrier of the present invention to a tissue sample or a simulated tissue sample. Hence, the PCT is preferred in the present invention.

By "PCT" is meant a pressure test that is used for measuring adhesive strength/sealing of a collagen carrier, such as a rolled and/or compressed collagen carrier to a synthetic membrane mimicking the adhesion to mammal tissue. The test is performed e.g. with a rolled collagen carrier sample that after unrolling iscut into a square of 3×3 cm. The active side of the cut samples are wetted with saline and placed onto the synthetic membrane that has been provided with a hole in the centre (Ø 1 cm). The membrane with the adhered sample of collagen carrier, such as a rolled and/or compressed collagen carrier is placed and fixed over an airtight chamber into which air is pumped. The pressure required to disrupt/burst the seal formed by the collagen carrier, such as a rolled and/or compressed collagen carrier is measured in mmHg and is called "adhesive strength" as defined above. The test is described in further details in example 4.

An embodiment of the present invention relates to a process according to the invention, wherein each individual collagen carrier, such as a rolled and/or compressed collagen carrier out of a sample of 10 collagen carriers have an adhesive strength of more than about 40 mmHg and wherein the average of 10 collagen carriers, such as a rolled and/or compressed collagen carrier in said sample has an adhesive strength of more than about 50 mmHg as measured by pressure test (PCT).

By the term "adherence" is meant the in vitro capability of a collagen carrier, such as a rolled and/or compressed collagen carrier to adhere to living tissue according to the present invention. Adherence is investigated qualitatively by visual inspection of adherence of a collagen carrier to a tissue and thus adherence approximates a part of the pharmaceutical activity of a collagen carrier, such as a rolled and/or compressed collagen carrier according to the invention i.e. the capability of a collagen carrier, such as a rolled and/or compressed collagen carrier to adhere to an isolated organ or piece of tissue. An example of an adherence test is shown in example 2 and FIG. 1 illustrates adherence.

By the term "loss of coating" is meant the strength of adhesion/fixation of the coating layer to the collagen layer, such as of the coating layer to a coiled/rolled and/or compressed collagen carrier. Loss of coating is described in further detail in example 1. This term should not be confused with "adherence" as discussed above.

Loss of coating layer is measured indirectly by weighing e.g. a rolled collagen carrier of a predetermined size prior to un-rolling it and weighing it immediately again after it has been unrolled, whereby an amount of coating that may have been lost is expressed in mg/cm$^2$ or in percentage, see below.

Figure 5:
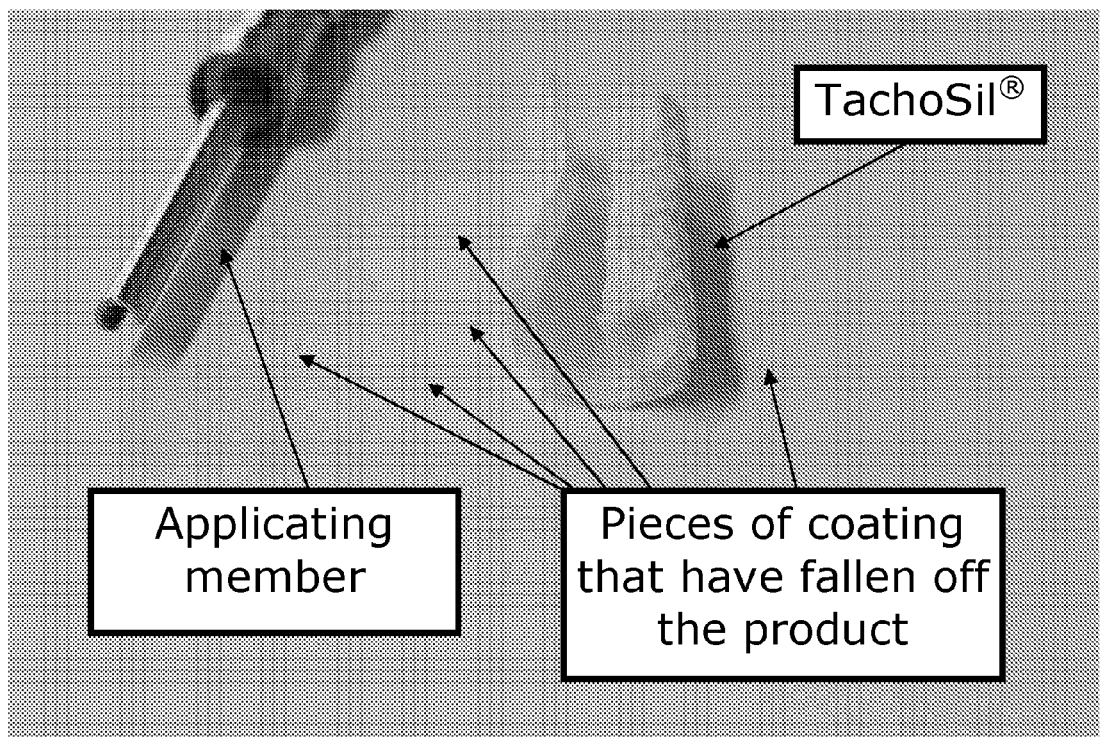
FIG. 5 shows a TachoSil® that has "sprung open" from the coiled configuration after having been rolled using an applicating member (shown in the left side of the figure) as disclosed in WO 97/21383. The coiled TachoSil® that has "sprung open" from the coiled configuration is shown in the right side of the figure. Pieces of coating that have fallen of the coiled TachoSil® are visible in the figure.

Harsh handling of a collagen carrier of the invention such as by mechanical manipulation (i.e. humidification, compression, rolling, unrolling, and passage through an access orifice, such as a trocar) may lead to coating falling off the collagen carrier, such as a rolled and/or compressed collagen carrier. Such a harsh handling is shown in FIG. 5. A method that can be used for determining the loss of coating is disclosed in example 1. The rolled compressed collagen carrier is substantially unchanged upon exit from said trocar or simply upon un-rolling not passing it through a trocar and has lost less coating material than 20%, such as less than 18%, such as less than 16%, such as less than 14%, such as less than 12%, such as less than 10%, such as less than 8%, such as less than 6%, such as less than 4%, such as less than 2%, such as less than 1.5%, such as less than 1%, such as less than 0.5%, such as less than 0.2%, such as 0% as an indication of the flexibility of the collagen carrier and the coating. In one embodiment of the present invention the percentages are calculated as follows: a rolled collagen carrier of the invention is weighed before it is passed through a trocar. After exit from said trocar said rolled collagen carrier is unrolled and weighed again immediately thereafter, whereby an amount of coating that may have been lost is expressed in percentage. It should be noted that an unrolled collagen carrier of the present invention has an acceptable PCT-value even if it loses less than 20% coating material.

The loss of coating is preferably less than 1.0 mg/cm$^2$, such as less than 0.9 mg/cm$^2$, such as less than 0.8 mg/cm$^2$, such as less than 0.7 mg/cm$^2$, preferably such as less than 0.6 mg/cm$^2$, such as less than 0.5 mg/cm$^2$, such as less than 0.4 mg/cm$^2$, such as less than 0.3 mg/cm$^2$, such as less than 0.2 mg/cm$^2$, such as less than 0.1 mg/cm$^2$, such as 0.01 mg/cm$^2$.

Obviously, it is not possible to measure the in vivo loss of coating upon exit of a rolled or rolled compressed collagen carrier of the invention from an access orifice, such as a trocar within a living organism.

By the term "sterility assurance level (SAL)" is meant a term used in microbiology to describe the probability of a single unit being non-sterile after it has been subjected to a sterilization process. For example, medical device manufacturers design their sterilization processes for an extremely low SAL leading to a 10$^{-6}$ microbial survivor probability, i.e. assurance of less than or equal to 1 chance in 1 million that viable microorganisms are present in the sterilized device, as defined in USP 34 <1211> (United States Pharmacopeia version 32, chapter 1211. SAL is also used to describe the killing efficacy of a sterilization process, where a very effective sterilization process has a very low SAL.

Sterilisation can occur before and/or after any packaging steps.

Gamma radiation can be used as a sterilization method to kill living organisms in a process called irradiation. Applications of irradiation include sterilizing medical equipment as an alternative to autoclaves or chemical means. In one embodiment of the present invention, a collagen carrier, such as a rolled and/or compressed collagen carrier, is subjected to gamma radiation. The gamma radiation may reduce the obtained PCT-value of the collagen carrier, such as no more than 0.5%, such as no more than 1%, such as no more than 2%, such as no more than 3%, such as no more than 4%, such as no more than 5%, such as no more than 6%, such as no more than 7%, such as no more than 8%, such as no more than 9%, such as preferably no more than 10%, such as no more than 11%, such as no more than 12%, such as no more than 13%, such as no more than 14%, such as no more than 15%, such as no more than 16%, such as no more than 17%, such as no more than 18%, such as no more than 19%, such as no more than 20%, such as no more than 25%. This was evaluated in vitro by visual inspection of adherence of a rolled collagen carrier according to the invention on liver tissue. Fibrinogen is preferably present in an amount of 2-10 mg/cm$^2$ and thrombin is preferably present in an amount of 1.0-5.5 IU/cm$^2$ after the irradiation process and it is preferred that the levels may exceed their respective levels such as no more than 0.5%, such as no more than 1%, such as no more than 2%, such as no more than 3%, such as no more than 4%, such as no more than 5%, such as no more than 6%, such as no more than 7%, such as no more than 8%, such as no more than 9%, such as preferably no more than 10%, such as no more than 11%, such as no more than 12%, such as no more than 13%, such as no more than 14%, such as no more than 15%, such as no more than 16%, such as no more than 17%, such as no more than 18%, such as no more than 19%, such as no more than 20%, such as no more than 25%. It is noted that "exceeding their respective levels" means that the values may either increase or decrease.

It is preferred that the rolled and/or compressed collagen carrier can be stored for an acceptable duration of time whilst maintaining their biological and physiochemical properties, i.e. preferably, storage neither affects the physical and chemical properties of said rolled and/or compressed collagen carrier nor the in vitro adherence (to liver tissue) and adhesive strength (PCT-value) of the rolled and/or compressed collagen carriers.

An acceptable shelf-life is preferably up to 60 months, such as up to 54 months, such as up to 48 months, such as up to 42 months, such as up to 36 months, such as up to 30 months, such as up to 24 months, such as up to 18 months, such as up to 12 months, such as up to 6 months, such as up to 5 months, such as up to 4 months, such as up to 3 months, such as up to 2 months, such as up to 1 month. Hence, it is preferred that rolled and/or compressed collagen carriers of the present invention are stable.

By the word "stable" is meant that said rolled and/or compressed collagen carriers are physiochemical and biologically stable meaning that they retain the same properties as they had when they were prepared. Hence, said rolled and/or compressed collagen carriers retain their stability under transport, warehousing (storage), logistics, sales, and up to and including the end use of said rolled and/or compressed collagen carriers i.e. the collagen carriers maintain regulations and all end-use requirements.

By the term "drying" is meant any well known method of drying an object such as by passive evaporation, desiccation, blowing air with a humidity lower than the object that needs drying over said object, applying heat etc. In one embodiment drying is performed in a drying tunnel i.e. tunnel comprises a conveyor belt transporting the trays that contains the rolled collagen carriers through the tunnel with an airflow securing the drying. In one embodiment the passage through the tunnel, i.e. the length of the drying takes around 30 min. In another embodiment the drying tunnel dries off the solvent such as dries off ethanol, e.g. dries off isopropanol, e.g. dries off isopropanol and ethanol. Water is dried off using a dessicant, such as e.g. silica gel. The drying off of water may take up to about 48 hours, such as up to about 36 hours, such as up to about 24 hrs, such as up to about 18 hours, such as up to about 12 hours, such as up to about 6 hours, such as up to about 2 hours. The drying off of water preferably takes up to about 24 hours.

Silica gel is preferably used to mean a granular, vitreous, porous form of silicon dioxide made synthetically from sodium silicate. Silica gel is a commonly used desiccant as beads packed in a permeable bag.

Endoscopic instrument: by "endoscopic instrument" is meant herein any endoscopic instrument known to one skilled in the art, for example endoscopic grab tongs, endoscopic pincet, endoscopic dissector, endoscopic forceps, Johansons clamp or other endoscopic clamp, endoscopic scissors, an endoscopic grasper, two or more graspers, laparoscopic swabs (preferably fastened to long pins or fixed to graspers), or another suitable endoscopic instrument.

In one embodiment of the present invention, the drying of an optionally humidified rolled and/or compressed collagen carrier according to the invention neither affects the physical and chemical properties of said collagen carrier nor the in vitro adherence (to liver tissue) and adhesive strength (PCT-value) of said collagen carrier. In one embodiment of the present invention, an optionally humidified rolled and/or compressed collagen carrier is dried by passive evaporation of a solvent, preferably ethanol, by controlling the room temperature and room humidity to within the ranges of which is 3-35° C., 5-80% RH, such as 13-35° C., 36-65% RH, such as 23-35° C., 36-65% RH, such as 33-35° C., 36-65% RH, such as 3-25° C., 36-65% RH, such as 3-15° C., 36-65% RH, such as 3-5° C., 36-65% RH, preferably 18-22° C., 40-60% RH, such as 18-22° C., 36-65% RH, such as at 20-25° C., 40-60% RH, such as at 22-25° C., 40-60% RH, such as at 24-25° C., 40-60% RH, such as at 18-23° C., 40-60% RH, such as at 18-21° C., 40-60% RH, such as at 18-19° C., 40-60% RH, such as at 18-25° C., 35-60% RH, such as at 18-25° C., 30-60% RH, such as at 18-25° C., 40-65% RH, such as at 18-25° C., 40-70% RH, such as at 18-25° C., 40-75% RH, such as at 18-25° C., 40-80% RH, such as at 18-25° C., 45-80% RH, such as at 18-25° C., 50-80% RH, such as at 18-25° C., 55-80% RH, such as at 18-25° C., 60-80% RH, such as at 18-25° C., 65-80% RH, such as at 18-25° C., 70-80% RH, such as at 18-25° C., 75-80% RH. Said optionally humidified rolled and/or compressed collagen carrier is preferably dried 30 minutes by blowing air with a humidity lower than said collagen carrier (such as a rolled and/or compressed collagen carrier that needs drying) over said collagen carrier followed by passive evaporation of the solvent by placing said collagen carrier in a dessicator.

An evaporation and/or a drying time of up to 24 hours is preferred, such as up to 20 hours, such as up to 15 hours, such as up to 10 hours, such as up to 5 hours, such as up to 1 hour, such as up to 50 minutes, such as up to 40 minutes, preferably such as up to 30 minutes, such as up to 20 minutes, such as up to 10 minutes, such as up to 5 minutes, such as up to 1 minute, such as up to 50 seconds, such as up to 40 seconds, such as up to 30 seconds, such as up to 20 seconds, such as up to 10 seconds, such as up to 5 seconds.

A residual amount of the applied at least one liquid solvent to the collagen carrier, such as a rolled and/or compressed collagen carrier is acceptable such as no more than 0.1% w/w, or such as no more than 0.2% w/w, or such as no more than 0.5% w/w, or such as no more than 0.8% w/w or such as no more than 1.0% w/w, or such as no more than 1.2% w/w, or such as no more than 1.4% w/w, or preferably such as no more than 1.6% w/w, or such as no more than 1.8% w/w, or such as no more than 2.0% w/w, or such as no more than 2.5% w/w, or such as no more than 3.0% w/w, or such as no more than 3.5% w/w, or such as no more than 4.0% w/w, or such as no more than 5.0% w/w, or such as no more than 8.0% w/w, or such as no more than 10.0% w/w, or such as no more than 12.5% w/w, or such as no more than 15.0% w/w, or such as no more than 17.5% w/w, or such as no more than 20.0% w/w, or such as no more than 22.5% w/w, or such as no more than 25.0% w/w, or such as no more than 27.5% w/w, or such as no more than 30.0% w/w, or such as no more than 32.5% w/w, or such as no more than 35.0% w/w. When the applied liquid solvent is ethanol, no more than 1.6% w/w residual ethanol is preferred and/or when the applied liquid solvent is water no more than 8.0% w/w residual water is preferred, preferably such as no more than 5.0% w/w. A residual amount of the applied at least one liquid solvent, such as at least two liquid solvents, such as at least three liquid solvents to the collagen carrier, such as a rolled and/or compressed collagen carrier is acceptable.

It may happen that one or more solvents or moisture from the room (aqueous vapour) is absorbed passively by a collagen carrier, such as a rolled and/or compressed collagen carrier during processing. In one embodiments, if such passive absorption of moisture, such as water, has taken place a residual amount of said moisture is acceptable such as no more than 0.1% w/w, such as no more than 0.2% w/w, such as no more than 0.5% w/w, such as no more than 0.8% w/w such as no more than 1.0% w/w, such as no more than 1.2% w/w, such as no more than 1.4% w/w, such as no more than 1.6% w/w, such as no more than 1.8% w/w, such as no more than 2.0% w/w, such as no more than 2.5% w/w, such as no more than 3.0% w/w, such as no more than 3.5% w/w, such as no more than 4.0% w/w, preferably such as no more than 5.0% w/w, such as no more than 8.0% w/w, such as no more than 10.0% w/w, such as no more than 12.5% w/w, such as no more than 15.0% w/w, such as no more than 17.5% w/w, such as no more than 20.0% w/w, such as no more than 22.5% w/w, such as no more than 25.0% w/w, such as no more than 27.5% w/w, such as no more than 30.0% w/w, such as no more than 32.5% w/w, such as no more than 35.0% w/w. When the passively absorbed solvent is water no more than 8.0% w/w residual water is preferred, preferably such as no more than 5.0% w/w. Residual solvent is measured by conventional methods known to the person skilled in the art, such as by using gas chromatography (GC). GC is a common type of chromatography used in analytical chemistry for separating and analyzing compounds that can be vaporized without decomposition. In the present invention, GC is used to determine one or more solvents or moisture from the room (aqueous vapour) in the collagen carrier.

Residual solvent and its passive uptake by a collagen carrier is described in further details in example 9.

By the term "sterilizing" is meant any well known method of sterilizing an object such as in the present invention a collagen carrier, such as a rolled and/or compressed collagen carrier. Any such appropriate sterilization method should result in the required probability of a single unit being non-sterile after it has been subjected to the sterilization process. Hence, preferably not more than one collagen carrier, such as a rolled and/or compressed collagen carrier in a million should be nonsterile after the sterilization process. An example of a sterilization process is gamma radiation. Sterilization can also be achieved by applying the proper combinations of heat, chemicals, irradiation, and high pressure, but these are less preferred methods. In a preferred embodiment the sterilization is performed using gamma irradiation.

By the term "packing" is meant any well known method of packaging an object such as in the present invention a collagen carrier, such as a rolled and/or compressed collagen carrier. Packaging and packing are words that are used interchangeably within this context. Packaging is meant to mean a coordinated system of preparing goods for transport, warehousing, logistics, sales, and end use. Packaging can for example contain, protect, preserve, transport, inform, and sell an object, preferably such an object as the collagen carrier, such as a rolled and/or compressed collagen carrier of the present invention. A suitable container is used for packing the collagen carrier, such as a rolled and/or compressed collagen carrier of the present invention.

By the term "suitable container" is meant in one embodiment any container that is suitable for transport, warehousing (storage), logistics, sales, and for the end use of a collagen carrier, such as a rolled and/or compressed collagen carrier of the present invention. Hence, said suitable container encloses and/or protects said collagen carrier. Thus preferably said collagen carrier, such as a rolled and/or compressed collagen carrier retains its properties substantially as they were at the time of packaging. An example of a suitable container is a tray made of PET (polyethylene terephthalate) or polystyrene shaped to fit the rolled collagen carrier of the present invention. A suitable container according to the present invention is further sealed with a lid, such as e.g. a Tyvec lid. In an embodiment of the invention, the closed tray with a lid is further placed inside a double aluminium foil, preferably with a dessicant. In an even further embodiment of the invention, the double aluminium foil is marked to indicate that the content has been sterilized (see further below). Other suitable containers are well known in the art.

In an embodiment package testing is conducted and documented to ensure that packages meet regulations and all end-use requirements. Manufacturing processes are controlled and validated to ensure consistent performance.

Preferably, a suitable container of the present invention is sterilized in the package. Medical device packaging is highly regulated and the sterility must be maintained throughout distribution to allow immediate use by physicians. A series of special packaging tests is well known in the art and used to measure the ability of the package to maintain sterility. Relevant standards include: ASTM D1585—Guide for Integrity Testing of Porous Medical Packages, ASTM F2097—Standard Guide for Design and Evaluation of Primary Flexible Packaging for Medical Products, EN 868 Packaging materials and systems for medical devices which are to be sterilized. General requirements and test methods, ISO 11607 Packaging for terminally sterilized medical devices, and others.

In an embodiment the container is a foil packaging material, such as a single or double aluminium foil or a plastic packaging material, such as a polystyrene or PET (polyethylene terephthalate) or a combination of a foil and plastic packaging material, such as a single or double aluminium foil and as a polystyrene or PET (polyethylene terephthalate).

Minimally invasive surgery (MIS) is a relatively new type of surgical procedure that induce less trauma to the body, thus usually resulting in quicker recovery of the patient and less pain for the patient. The MIS procedures are usually more technically demanding than open surgery, and the surgeon may need to proceed to open surgery if complications occur.

MIS procedures require specially designed surgical instruments such as laparoscopic devices and remote-control manipulation of instruments with indirect observation of the surgical field through an endoscope or similar device. These instruments are placed through small incisions or natural orifices (openings).

In for example abdominal surgery the access of the instruments is usually done through so-called trocars, which are a type of access tube. Trocars are tubes, such as rigid tubes, and preferably have a typical inner diameter of 5 to 12 mm, such as 5-10 mm.

In the present invention, trocars preferably have a diameter of no more than 12 mm, such as preferably no more than 10 mm, such as no more than 8 mm, such as no more than 6 mm, such as no more than 4 mm, such as no more than 2 mm. In the present context a trocar may also be a flexible tube. The trocar allows the insertion of instruments and material while creating room for vision (using video endoscopes) and surgical manipulation. MIS procedures also include robotic surgery. The small size of the orifices used in MIS restricts what can be inserted into the orifices. All surgical tools and materials used during MIS procedures must be of a size and condition that allow for their insertion through the access orifices. The tools and materials are for the most part especially designed for use in minimally invasive surgery.

Hence, by the term "minimal or minimally invasive surgery (MIS)" is meant any procedure (surgical or otherwise) that is less invasive than open surgery used for the same purpose. Many medical procedures are called minimally invasive, such as hypodermic injection, air-pressure injection, subdermal implants, endoscopy, percutaneous surgery, laparoscopic surgery, thoracoscopic surgery arthroscopic surgery, cryosurgery, microsurgery, keyhole surgery, endovascular surgery (such as angioplasty), coronary catheterization, permanent spinal and brain electrodes, stereotactic surgery, The Nuss Procedure, radioactivity-based medical imaging methods, such as gamma camera, Positron emission tomography and SPECT (single photon emission tomography). Related procedures are image-guided surgery, robotic surgery and interventional radiology.

Minimally invasive procedures are performed through one or more short incisions ('keyhole surgery') or through natural body openings. The terminology varies depending on the route of surgical access, the type of surgery, and the tools used, e.g. endoscopy, laparoscopy, or thoracoscopy.

Endoscopy means looking inside and typically refers to looking inside the body for medical reasons using an endoscope, an instrument used to examine the interior of a hollow organ or cavity of the body. Hence, the words "endoscopic surgery" is meant to mean any surgery performed by using endoscopy such as endoscopy involving the gastrointestinal tract (GI tract): esophagus, stomach and duodenum (esophagogastroduodenoscopy), small intestine (enteroscopy) large intestine/colon (colonoscopy, sigmoidoscopy), magnification endoscopybile duct endoscopic retrograde cholangiopancreatography (ERCP), duodenoscope-assisted cholangiopancreatoscopy, intraoperative cholangioscopy, an anoscope, a proctoscope, and a rectoscope with approximate lengths, rectum (rectoscopy) and anus (anoscopy), both also referred to as (proctoscopy). It further includes the respiratory tract: The nose (rhinoscopy), the lower respiratory tract (bronchoscopy), the ear (otoscope), the urinary tract (cystoscopy), the female reproductive system (gynoscopy), the cervix (colposcopy), the uterus (hysteroscopy), and the fallopian tubes (falloposcopy). Normally closed body cavities may be viewed through a small incision: The abdominal or pelvic cavity (laparoscopy), the interior of a joint (arthroscopy), organs of the chest (thoracoscopy and mediastinoscopy), during pregnancy: the amnion (amnioscopy), the fetus (fetoscopy). It further includes plastic surgery panendoscopy (or triple endoscopy) which combines laryngoscopy, esophagoscopy, and bronchoscopy. In addition, orthopedic surgery and hand surgery, such as endoscopic carpal tunnel release and epidural space (epiduroscopy) is also a form of endoscopy.

Laparoscopic surgery includes operations within the abdominal or pelvic cavities, whereas keyhole surgery performed on the thoracic or chest cavity is called thoracoscopic surgery. Laparoscopic and thoracoscopic surgery both belong to the broader field of endoscopy.

By an "access orifice" or "orifice" is meant the point of entry through which the coiled collagen carrier of the invention is passed prior to reaching the target location. For embodiments of the present invention relating to MIS procedures, the term "orifice" or "access orifice" means the point on entry of the surgical tools and materials used during MIS procedures. Hence, such surgical tools and materials must be of a size and condition that allow for their insertion through the access orifices. The access orifice can e.g. be a natural orifice in the body or can e.g. be in a trocar. However, the access orifice or orifice is not necessarily a narrow entry point, it may also be a wide area, such as an access orifice created during open surgery, such as open abdominal surgery or the access orifice/orifice created during open heart surgery.

By the words "hemostasis or haemostasis" is meant e.g. a complex process which causes a bleeding process to stop. It refers to the process of keeping blood within a damaged blood vessel (the opposite of hemostasis is hemorrhage). Most of the time this includes the changing of blood from a fluid to a solid state (coagulation) or for example by physically sealing open vessels.

By the expression "injury" is meant damage to a biological organism, such as injury associated with performing MIS. Tissue injury may include conditions where leakage of e.g. blood, lymph, bile, cerebrospinal fluid or air/gas is present, thus needing local treatment to control the bleeding (haemostasis) or stop the exhudate (tissue sealing).

By the terms "organ" or "tissue" is meant any organ or tissue in the human or animal body, either having been isolated from the human or animal body or alternatively in vivo, for example an organ or tissue that is operated on during a surgical procedure. For example, the term "organ" as used herein can refer to e.g. any of the organs on the following non-limiting list:—heart, blood vessels, salivary glands, esophagus, stomach, liver, gallbladder, pancreas, intestines, colon, rectum, anus, hypothalamus, pituitary, pituitary gland, pineal body, pineal gland, thyroid, parathyroids, adrenal glands, kidney, ureter, bladder, urethra, lymph node, lymph vessel, tonsils, adenoids, thymus, spleen, skin, hair, nails, muscles, brain, spinal cord, nerves, ovaries, fallopian tubes, uterus, vagina, mammary glands, testes, vas deferens, seminal vesicles, prostate, penis, spleen, pharynx, larynx, trachea, bronchi, lungs, diaphragm, bones, cartilage, ligaments and tendons. The term "tissue" as used herein can for example refer to e.g. any of the tissue types on the following non-limiting list:—epithelial tissue, connective tissue, muscle tissue and/or nerve tissue.

By the term "weight-weight percentage" or "% w/w" is meant grams substance per grams of another substance in percent (per 100 gram). Thus, if e.g. residual water is present in an amount of 2% w/w in a collagen carrier, it is meant to mean 2 grams of water is present with 98 grams of collagen carrier. The total weight will be 100 grams of the collagen carrier including the residual water but the volume of the 100 grams of residual may be different from 100 ml.

Note that by the "weight" of the collagen carriers is meant the weight of the collagen carrier excluding the weight of the coating layer.

It should be noted that embodiments and features described in the context of one of the aspects of the present invention also apply to the other aspects of the invention i.e. all aspects relating to a rolled compressed collagen carrier also apply to a compressed collagen carrier or a rolled collagen carrier or an unrolled rolled compressed collagen carrier or a coiled collagen carrier (as the terms "coiled" and "rolled" are used interchangeably herein), and similarly for the process aspects.

An aspect of the present invention relates to a process for coiling a collagen carrier, the collagen carrier comprising (i) a collagen layer and (ii) a coating layer comprising fibrinogen and thrombin, said process comprising the sequential steps of:
humidifying at least part of said collagen carrier,
coiling said collagen carrier by gripping the collagen carrier between a pair of elongated members, and rotating the pair of elongated members about an axis being parallel to a longitudinal extension of the elongate members in order to coil the collagen carrier on the members, while the collagen carrier is supported by a support device,
drying the coiled collagen carrier,
thereby providing a form-stable coiled collagen carrier.

Another aspect of the present invention relates to a process for coiling a collagen carrier, the collagen carrier comprising (i) a collagen layer and (ii) a coating layer preferably comprising fibrinogen and thrombin, said process comprising the sequential steps of:
humidifying at least part of said collagen carrier,
coiling said collagen carrier
drying the coiled collagen carrier,
thereby providing a form-stable coiled collagen carrier.

Any type of fibrinogen and/or thrombin can be used in the coating layer, preferably the fibrinogen and/or thrombin used in the coating layer is mostly solid and/or solid. It is preferred that the fibrinogen and/or thrombin are dry. Preferably, said sequential steps are consecutive steps. In an embodiment of the present invention, the process consists of the above-mentioned process steps. In another embodiment, the process comprises or consists of the above-mentioned process steps and a further packing step wherein the coiled product is sealed in a container, and sterilized. In an embodiment of the present invention, the coiling is performed by gripping the collagen carrier using at least one gripping device. In an embodiment of the present invention, the coiling is performed by gripping the collagen carrier using at least one pair of tweezers or pincers.

The drying of the coiled collagen carrier can be done using any suitable drying process, such as e.g. by blowing air with a humidity lower than the coiled collagen carrier and optionally applying heat to the air. Preferably, said drying is at least 5 minutes long, such as between 5 minutes and 1 hour, such as between 20 minutes and 40 minutes long, such as between 25 and 35 minutes long. A ventilation tunnel can for example be used for the drying step.

Any surface of the collagen carrier can be humidified. Preferably, at least the coating layer of said collagen carrier is humidified. In one embodiment of the present invention only the coating layer is humidified, in another embodiment of the invention both the top and bottom sides of the collagen carrier are humidified. In another embodiment of the present invention, the surface humidified is the collagen layer.

Preferably, the collagen carrier is humidified by a solvent. Any suitable solvent can be used, such as an organic solvent or water. In an embodiment of the present invention, the solvent comprises or consists of ethanol, such as dehydrated ethanol with a maximum content of 0.1% water. In another embodiment, the solvent comprises or consists of ethanol, such as dehydrated ethanol with a maximum content of 0.1% water, and water. The solvent can also comprise or consist of isopropanol. The solvent can alternatively be a mixture of at least 70% ethanol such as dehydrated ethanol with a maximum content of 0.1% water and another solvent (such as water), such as at least 80% ethanol, such as at least 90% ethanol, such as at least 95% ethanol. The solvent can in another embodiment be a mixture of at least 80% isopropanol and another solvent (such as water), such as at least 90% or 95% isopropanol. The solvent can also comprise fibrinogen and/or thrombin and/or other factors. In a preferred embodiment the ethanol may be dehydrated ethanol with a maximum content of 0.1% water.

In an embodiment of the present invention, the rolling/coiling up step is performed after the coating layer has been softened.

Preferably, the coating layer of the collagen carrier is humidified using a solvent. In an embodiment of the present invention, the collagen carrier is humidified on the coating layer by a solvent in an amount between 0.1 and 25 $cm^2$ surface of the coating layer, such as e.g. 1.2-10.75 $mg/cm^2$ surface of the coating layer. For rolled versions of the standard TachoSil® sizes available on the market (such as e.g. midi sized fleeces), the following solvent amounts are preferred on the coating layer: 30-160 mg solvent (such as ethanol) per collagen carrier, such as 30-100 mg solvent (such as ethanol) per collagen carrier, such as preferably 90-100 mg solvent (such as ethanol) per collagen carrier, such as for a collagen carrier with a 25 $cm^2$ coating surface such as for the small or midi sized Tachosil® collagen carrier. In an embodiment of the present invention, the solvent comprises or consists of ethanol or dehydrated ethanol with a maximum content of 0.1% water.

In an embodiment of the process for coiling a collagen carrier, the process further comprises the step of compressing the collagen carrier to reduce the thickness of the collagen carrier. For example, the collagen carrier can be compressed with a compression ratio between 2 and 18, such as e.g. 4-14, such as preferably between 6-12. The compression step can in one embodiment be performed by passing the humidified collagen carrier through a set of rollers having a gap size being smaller than the thickness of the collagen carrier before passing through the set of rollers. An example gap size is between 0.2 mm and 2 mm, such as e.g. 0.4-1.6 mm, such as between 0.5-1.0 mm, or no more than 0.75 mm, such as e.g. 0.5-0.75. One preferred gap size is 0.6 mm. The compression is preferably performed prior to the coiling of the collagen carrier.

During the drying step of the coiling process, the coiled collagen carrier can be supported by a support device, e.g. by contacting the support device. For example, at least an edge of the coiled collagen carrier is fixed by the support device relatively to the coiled collagen carrier during drying, i.e. the edge of the coiled collagen carrier is pushed against the support device. The support device can be any suitable shape, such as e.g. a "U" shape, a rounded shape, a tubular shape or any other shape capable of supporting and maintaining the coiled shape of the collagen carrier while it is drying, prior to the product becoming form-stable in the dry state. In one preferred embodiment, the support device is a cavity shaped as a segment of a cylinder having at least one open end, and wherein the curved part of the cylinder segment extends at least 180° (see e.g. FIG. 11). In one embodiment of the present invention, the edge of the coiled collagen carrier is arranged inside the segment of the cylinder and the edge abuts the inner surface of the cylinder.

Preferably, the process of the present invention further comprises the step of extracting the elongated members from the coiled collagen carrier. For example, the extraction of the elongated members is performed before drying of the coiled collagen carrier. The elongated members can be a pair of tweezers, so for example the extraction of the at least one pair of tweezers can be performed before drying of the coiled collagen carrier. Preferably the elongated members form a gripping device.

In an embodiment of the present invention, the process further comprises the step of arranging the form-stable coiled collagen carrier in a container and subsequently sealing the container. For example, the coiled carrier can be arranged in an inner container and the inner container can be arranged in an outer container, further optionally comprising the step of arranging a desiccator inside the outer container prior to sealing of the container.

The process of the present invention preferably comprises the step of sterilizing the coiled collagen carrier. This can for example be done using gamma radiation. One embodiment of the present invention comprises the step of sterilizing the coiled collagen carrier to a sterility assurance level (SAL) of $10^{-6}$ using gamma radiation.

The process of the present invention can comprise a step wherein a label with information relating to the product of the present invention, such as e.g. relating to the sterilization level, is placed on the outside of the outer container.

In one embodiment of the present invention, the process for coiling a collagen carrier has the feature that the atmosphere surrounding the collagen carrier and humidification device while being humidified, compressed and coiled, is maintained at a set temperature and/or humidity. The temperature and/or humidity can for example be in the range of 10-40° C. and 10-70% RH. Preferably, the temperature is 18-22° C. and the relative humidity is 30-50%.

In an embodiment the temperature is 5-30° C., such as 10-25° C., such as 10-30° C., such as 15-30° C. In another embodiment the relative humidity is 2-60% RH, such as 10-55% RH, such as 20-55% RH, such as 30-55% RH, such as 40-55% RH. Preferably the relative humidity is 30-50% RH.

Another aspect of the present invention relates to a coiled collagen carrier obtainable by any of the coiling or rolling process described herein (the terms "coiling" and "rolling" are used interchangeably herein). For example, the present invention relates in one embodiment to a coiled collagen carrier obtained by the process of the present invention.

Another aspect of the present invention relates to a coiled collagen carrier
comprising a collagen layer and a coating layer on top of the collagen layer, the coating layer comprising a (preferably mostly solid) thrombin and (preferably mostly solid) fibrinogen, and
having the shape of a elongate element with a number of windings of the collagen carrier about the longitudinal axis of the elongate element and at least the outer winding(s) being orientated so that the coating layer constitutes the outer surface of each of said outer windings,
wherein
the coiled collagen carrier is form-stable and defines a collagen carrier in a coiled configuration where said outer winding(s) proceed along a spiral in a cross section of the collagen carrier.

The windings being referred to as the outer windings are preferably each winding of the coiled collagen carrier except the inner most winding which typically is coiled to define an "S" when seen in a cross sectional view. In some embodiments the coiled collagen carrier may comprising only one outer winding and in such instances the winding being referred to as outer windings is preferably this single outer winding.

The coiled collagen carrier comprises a collagen layer. The collagen layer can be made from any suitable collagen, such as e.g. a collagen foam or sponge, such as e.g. the commercially available Nycomed "TachoTop" product. A preferred collagen type is human collagen, such as a solidified human collagen foam. The coiled collagen carrier also comprises a coating layer on top of the collagen layer, which comprises thrombin and fibrinogen. The thrombin is preferably mostly solid or solid. The fibrinogen is preferably mostly solid or solid. Preferably both the thrombin and fibrinogen are solid. Preferably the coating also comprises riboflavin, which provides a yellow colour and enables the medical practitioner to determine which side of the collagen carrier is the active side.

In preferred embodiments of the present invention, at least the outer windings or each winding of the coiled collagen carrier is orientated so that the coating layer constitutes the inner surface of each winding. In other embodiments of the present invention, each winding or at least the outer windings of the coiled collagen carrier is/are orientated so that the coating layer constitutes the outer surface of each of said windings.

In an embodiment of the present invention, the collagen carrier is preferably a layered construction, for example consisting of a layer of collagen and a coating layer on top of the collagen layer.

The coiled collagen carrier of the present invention is form-stable. This can for example mean that the coiled collagen carrier is form-stable in the sense that it does not un-coil "when at rest". In one embodiment of the present invention, the form-stability of the coiled collagen carrier diminishes when moisture is applied to it by which is meant that the product becomes more flexible (i.e. less form-stable). In a preferred embodiment of the present invention, the form-stability of the coiled collagen carrier is provided substantially only by the coating. At least some of the form-stability of the coiled collagen carrier can in one embodiment be provided by the outer most winding of the carrier. In one embodiment of the present invention, the form-stability of the coiled collagen carrier is provided by a region at the edge of the coiled collagen carrier adhering to the subjacent winding. In another embodiment, the form-stability of the coiled collagen carrier is provided by an adherence between the windings. In an embodiment of the present invention, the form-stability of the coiled collagen carrier is provided by the coiled collagen carrier having no mechanical tension. In an embodiment of the present invention, the form-stability of the coiled collagen carrier is provided by outbalancing mechanical tension acting to un-coil the coiled collagen carrier by an adherence between the windings. In an embodiment of the present invention, the form-stability of the coiled collagen carrier is provided by the coil having a elasticity module of 5-100 N/cm$^2$.

In one embodiment of the present invention, the form-stability is provided by the coiled collagen carrier forming a brittle coil which, when subjected to stress, breaks without significant deformation.

In a preferred embodiment of the present invention, the coiled collagen carrier in an unrolled configuration is a (preferably rectangular or square-shaped) sheet, preferably having a width, a length and a thickness. Preferably, said unrolled collagen carrier is a rectangular or square sheet. Preferably the sheet has a thickness of between 0.5 mm and 10 mm, such as e.g. 0.5-8 mm, for example 0.5-6 mm. In a preferred embodiment of the present invention, said thickness is preferably 1-4 mm. such as preferably 1-3 mm. The thickness can in one embodiment be at the most 4 mm, or at the most 5 mm, or at the most 6 mm, or at the most 7 mm. The unrolled collagen carrier preferably has a surface area on its top surface (which preferably is coated with the coated layer) of 4-100 $cm^2$, more preferably 5-75 $cm^2$, such as 10-50 $cm^2$, such as e.g. 20-30 $cm^2$, for example 25 $cm^2$ which can e.g. be given by a top surface of a 5 cm×5 cm square collagen sheet.

In an embodiment of the present invention, the coiled collagen carrier comprises or consists of three, four or five windings.

In an embodiment of the present invention, the coiled collagen carrier has a cylindrical shape with an outer diameter of less than 12 mm, such as less than 11 mm, such as less than 10 mm, such as less than 9 mm, such as less than 8 mm, such as less than 7 mm, such as less than 6 mm, such as less than 5 mm, such as less than 4 mm, such as less than 3 mm. For example, the coiled collagen carrier has an outer diameter of 1-12 mm, such as e.g. 3-11 mm, such as e.g. 5-10 mm, such as preferably 5-9 mm, such as e.g. 6-8 mm.

In an embodiment of the present invention, the coiled collagen carrier has an s-shaped inner most winding about the longitudinal axis of the coiled collagen carrier.

It is preferred that the coating of the coiled collagen carrier coating layer has no through-going cracks, such as through-going cracks visible by the naked eye.

The present invention further relates to a packed coiled collagen carrier, comprising the coiled collagen carrier according to the present invention arranged in a container. The container can for example be sealed to prevent contamination and/or degradation and/or to maintain form-stability of the coiled collagen carrier. Preferably the container is sealed to prevent contamination and/or absorption of liquid solvents such as e.g. water. The container can in one embodiment further comprise a desiccant, such as silica gel, arranged in the container.

The container can in an embodiment comprise an inner container and an outer container. Preferably, the inner container comprises a cavity shaped as a segment of a cylinder, and wherein the curved part of the cylinder segment extends at least 180°, the cavity being sealed by a tear-off or breakable foil. It is preferred that the outer container comprises a sealed pouch inside which the sealed inner container is arranged together with a dessicant.

The packed coiled collagen carrier according to the invention can also further comprise a label arranged to be visually inspected without opening the package and indicating whether the package with coiled collagen carrier has been exposed to radiation sterilization, such as to X-rays, such as to high-energy X-rays, or such as to gamma radiation, or such as to electron beams, or such as to ultraviolet light. The label can for example be arranged on the outside of the outer container.

Figure 10:
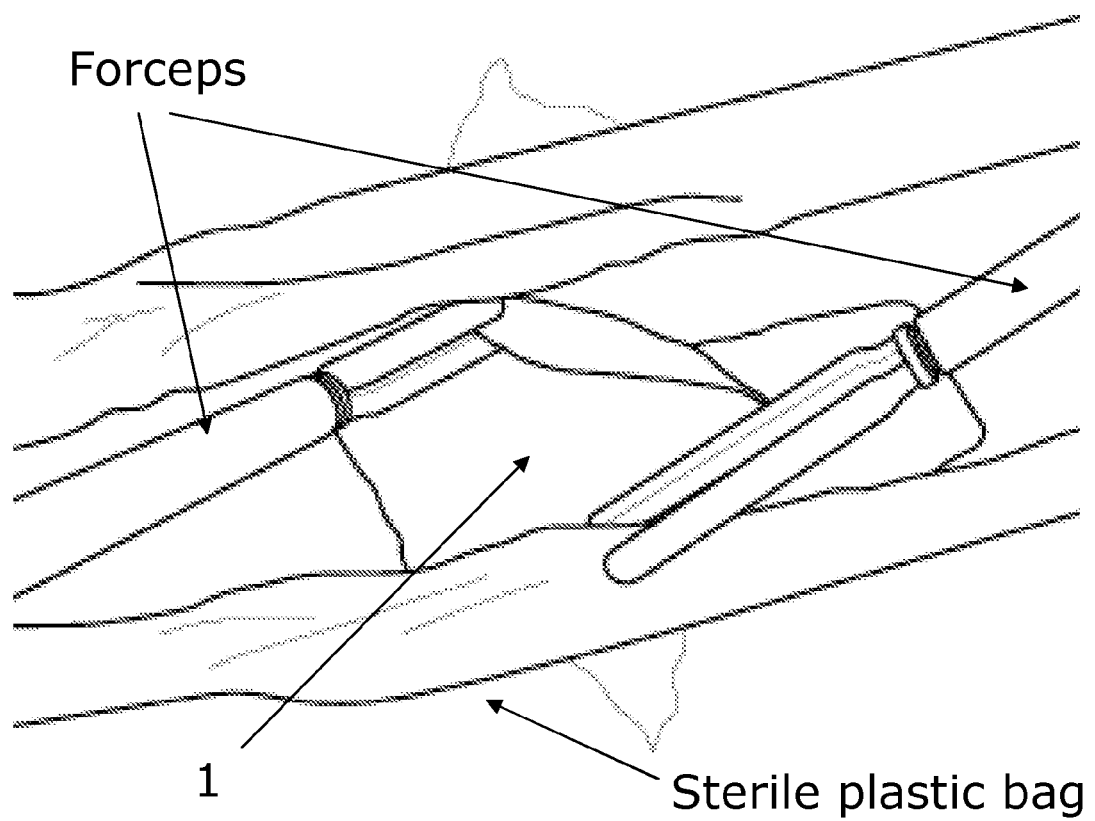
FIG. 10 shows a coiled collagen carrier (in an uncoiled state) applied inside e.g. a cavity or hole in an organ or tissue, such as in lung surgery being un-packed from a sterile plastic bag with a minimal amount of air inside using two sets of forceps.

The packed coiled collagen carrier according to the invention can also comprise a sterile plastic bag with a minimal amount of air inside, preferably with no air being in the bag, the bag being especially suited for protecting the coiled collagen carrier from being activated by bodily fluids when using it in e.g. surgery. This is illustrated in FIG. 10. This thin plastic bag may optionally be used after having un-packed the packed coiled collagen carrier according to the invention.

One aspect of the invention relates to a process for the preparation of a rolled compressed collagen carrier comprising the steps of
 a) providing a collagen carrier having a coating comprising solid fibrinogen and solid thrombin evenly distributed and fixed upon said collagen carrier
 b) optionally humidifying at least part of said collagen carrier providing an optionally humidified collagen carrier,
 c) compressing said optionally humidified collagen carrier providing a compressed collagen carrier,
 d) rolling said compressed collagen carrier,
 e) obtaining a rolled compressed collagen carrier,
 f) optionally drying the rolled compressed collagen carrier of step e),
 g) optionally sterilizing the rolled compressed collagen carrier of step e) or f),
 h) optionally packing the rolled compressed collagen carrier of step e), f) or g) into a suitable container,
 and thereby obtaining a rolled compressed collagen carrier having at least one of the following physical properties:
 I. a diameter of at the most 10 mm
 II. an adhesive strength of at least 40 mmHg as measured by a pressure test (PCT) after un-rolling of said rolled compressed collagen carrier, and
 III. a sterility assurance level (SAL) of $10^{-6}$.

An embodiment of the invention relates to a process according to the invention, wherein the steps of preparing said rolled compressed collagen carrier comprises the steps of
 a) humidifying at least part of said collagen carrier providing a humidified collagen carrier,
 b) compressing said humidified collagen carrier providing a compressed collagen carrier,
 c) rolling said compressed collagen carrier providing a rolled compressed collagen carrier,
 d) drying said rolled compressed collagen carrier,
 e) optionally sterilizing said rolled compressed collagen carrier of step c) or d),
 f) optionally packing said rolled compressed collagen carrier of step c), d) or e) into a suitable container.

An embodiment of the invention relates to a process according to the invention, wherein the steps of preparing said rolled compressed collagen carrier comprises the steps of
 a) humidifying at least part of said collagen carrier providing a humidified collagen carrier,
 b) compressing said humidified collagen carrier providing a compressed collagen carrier,
 c) rolling said compressed collagen carrier providing a rolled compressed collagen carrier,
 d) drying said rolled compressed collagen carrier,
 e) sterilizing said rolled compressed collagen carrier of step c) or d),
 f) optionally packing said rolled compressed collagen carrier of step d), d) or e) into a suitable container.

An embodiment of the invention relates to a process according to the invention, wherein the steps of preparing said rolled compressed collagen carrier comprises the steps of
 a) humidifying at least part of said collagen carrier providing a humidified collagen carrier, b) compressing said humidified collagen carrier providing a compressed collagen carrier,
c) rolling said compressed collagen carrier providing a rolled compressed collagen carrier,
d) drying said rolled compressed collagen carrier,
e) sterilizing said rolled compressed collagen carrier,
f) packing said rolled compressed collagen carrier into a suitable container.

An embodiment of the invention relates to a process according to the invention, wherein said rolled compressed collagen carrier has an adhesive strength of at least 50 mmHg as measured by a pressure test (PCT) after un-rolling said rolled compressed collagen carrier.

An embodiment of the invention relates to a process according to the invention, wherein said rolled compressed collagen carrier has an adhesive strength of at least 60 mmHg as measured by a pressure test (PCT) after un-rolling said rolled compressed collagen carrier.

An embodiment of the invention relates to a process according to the invention, wherein ethanol is used for humidifying at least part of said collagen carrier.

An embodiment of the invention relates to a process according to the invention, wherein said ethanol is applied in an amount of about 0.8-10.4 mg/cm$^2$ of collagen carrier.

An embodiment of the invention relates to a process according to the invention, wherein said ethanol is applied in an amount of about 0.8-6.1 mg/cm$^2$ of said collagen carrier.

An embodiment of the invention relates to a process according to the invention, wherein said ethanol is applied in an amount of about 1.2-4.7 mg/cm$^2$ of said collagen carrier.

An embodiment of the invention relates to a process according to the invention, wherein said ethanol is applied to at least one side of said collagen carrier that does comprise said coating, e.g said ethanol is applied to at least one side of said collagen carrier, wherein said at least one side comprises a coating.

An embodiment of the invention relates to a process according to the invention, wherein said ethanol is applied to at least one side of said collagen carrier that does not comprise said coating.

An embodiment of the invention relates to a process according to the invention, wherein said ethanol is applied to at least two opposing sides of said collagen carrier wherein at least one of said sides comprises said coating.

An embodiment of the invention relates to a process according to the invention, wherein said coating is externally oriented upon said rolled compressed collagen carrier.

An embodiment of the invention relates to a process according to the invention, wherein said coating is internally oriented upon said rolled compressed collagen carrier.

An embodiment of the invention relates to a process according to the invention, wherein said compression is performed using roller compaction with a gap size between the rollers of no more than 0.75 mm and wherein the diameter of the rollers are about 10-100 mm.

An embodiment of the invention relates to a process according to the invention, wherein said sterilization is performed using gamma radiation.

An embodiment of the invention relates to a process according to the invention, wherein said collagen carriers are processed at 3-35° C. and 5-80% RH (relative humidity).

An embodiment of the invention relates to a process according to the invention, wherein said collagen carriers are processed at 18-22° C. and 36-65% RH (relative humidity).

An embodiment of the invention relates to a process according to the invention, wherein said drying results in said rolled compressed collagen carrier comprising no more than 2.0% w/w (residual) ethanol.

An embodiment of the invention relates to a process according to the invention, wherein said drying results in said rolled compressed collagen carrier having no more than 1.6% w/w (residual) ethanol.

An embodiment of the invention relates to a process according to the invention, wherein said drying results in said rolled compressed collagen carrier comprising no more than 10.0% w/w (residual) water.

An embodiment of the invention relates to a process according to the invention, wherein said drying results in said rolled compressed collagen carrier comprising no more than 8.0% w/w (residual) water.

An embodiment of the invention relates to a process according to the invention, wherein said coating comprises solid human fibrinogen in an amount of about 5.5 mg/cm$^2$ and solid human thrombin in an amount of about 2.0 IU/cm$^2$.

An embodiment of the invention relates to a process according to the invention, wherein said rolled compressed collagen carrier has a loss of coating immediately after un-rolling of less than 0.6 mg/cm$^2$ as measured by weighing.

An embodiment of the invention relates to a process according to the invention, wherein said rolled compressed collagen carrier is at least partly mechanically processed, thereby providing an at least partly mechanically rolled compressed collagen carrier, such as a mechanically rolled compressed collagen carrier.

An embodiment of the invention relates to a process according to the invention, wherein said collagen carrier has a density in the range of 3.0-4.5 mg/cm$^3$. The density of a collagen carrier of the present invention is the density of the collagen carrier excluding the coating layer.

An aspect of the invention relates to a process for the preparation of a compressed collagen carrier, comprising the steps of
a. providing a collagen carrier having a coating comprising solid fibrinogen and solid thrombin evenly distributed and fixed upon said collagen carrier
b. optionally humidifying at least part of said collagen carrier providing an optionally humidified collagen carrier,
c. compressing said optionally humidified collagen carrier providing a compressed collagen carrier
d. optionally drying said compressed collagen carrier of step c),
e. optionally sterilizing said compressed collagen carrier of step c) or d),
f. packing said compressed collagen carrier of step c), d) or e) into a suitable container,
and thereby obtaining a compressed collagen carrier having at least one of the following physical properties:
I. a thickness of at the most 4 mm
II. an adhesive strength of at least 40 mmHg as measured by a pressure test (PCT)
III. a sterility assurance level (SAL) of $10^{-6}$.

An embodiment of the invention relates to a process according to the invention, wherein said compressed collagen carrier has an adhesive strength of at least 50 mmHg as measured by a pressure test (PCT).

An embodiment of the invention relates to a process according to the invention, wherein said compressed collagen carrier has an adhesive strength of at least 60 mmHg as measured by a pressure test (PCT).

An embodiment of the invention relates to a process according to the invention, wherein said collagen carrier has a density in the range of 3.0-4.5 mg/cm³. Please note that the density of a collagen carrier of the present invention is the density of the collagen carrier excluding the coating layer.

An aspect of the invention relates to a process for the preparation of a rolled collagen carrier comprising the steps of
a. providing a collagen carrier having a coating comprising solid fibrinogen and solid thrombin evenly distributed and fixed upon said collagen carrier
b. optionally humidifying at least part of said collagen carrier providing an optionally humidified collagen carrier,
c. rolling said collagen carrier providing a rolled collagen carrier,
d. optionally drying the rolled collagen carrier of step c),
e. optionally sterilizing the rolled collagen carrier of step c) or d),
f. optionally packing the rolled collagen carrier of step c), d) or e) into a suitable container,
and thereby obtaining a rolled collagen carrier having at least one of the following physical properties:
I. a diameter of at the most 10 mm
II. an adhesive strength of at least 40 mmHg as measured by a pressure test (PCT) after un-rolling of said rolled collagen carrier, and
III. a sterility assurance level (SAL) of $10^{-6}$.

An embodiment of the invention relates to a process according to the invention, wherein said rolled collagen carrier has an adhesive strength of at least 50 mmHg as measured by a pressure test (PCT) after un-rolling said collagen carrier.

An embodiment of the invention relates to a process according to the invention, wherein said rolled collagen carrier has an adhesive strength of at least 60 mmHg as measured by a pressure test (PCT) after un-rolling said collagen carrier.

An embodiment of the invention relates to a process according to the invention, wherein said rolled collagen carrier has a loss of coating immediately after un-rolling of less than 0.6 mg/cm² as measured by weighing.

An embodiment of the invention relates to a process according to the invention, wherein the collagen carrier has at least one of the following physical properties:
elasticity module in the range of 5-100 N/cm²,
density of 1-10 mg/cm³,
chamber diameter of more than 0.75 mm and less than 4 mm
and/or having a chamber diameter average below 3 mm
and evenly distributed and fixed upon said collagen carrier
a) solid fibrinogen
b) solid thrombin.

An embodiment of the invention relates to a process according to the invention, wherein said collagen carrier has a density in the range of 3.0-4.5 mg/cm³.

Please note that the density of a collagen carrier of the present invention is the density of the collagen carrier excluding the coating layer.

An aspect of the invention relates to a process of un-rolling a rolled compressed collagen carrier, comprising the steps of
a) providing a rolled compressed collagen carrier prepared according to the process of the invention,
b) un-packing said rolled compressed collagen carrier from said suitable container,
c) passing said rolled compressed collagen carrier through an access orifice, such as a trocar
d) un-rolling said rolled compressed collagen carrier upon exit from said access orifice,
e) obtaining an unrolled rolled compressed collagen carrier having an adhesive strength of at least 40 mmHg as measured by a pressure test (PCT), and a sterility assurance level (SAL) of $10^{-6}$.

An embodiment of the invention relates to a process according to the invention, wherein said rolled compressed collagen carrier has a loss of coating immediately after un-rolling of less than 0.6 mg/cm² as measured by weighing.

An embodiment of the invention relates to a process according to the invention, wherein the rolled compressed collagen carrier has an adhesive strength of at least 50 mmHg as measured by a pressure test (PCT) after un-rolling.

An embodiment of the invention relates to a process according to the invention, wherein the rolled compressed collagen carrier has an adhesive strength of at least 60 mmHg as measured by a pressure test (PCT) after un-rolling.

An aspect of the invention relates to a process of un-rolling a rolled collagen carrier, comprising the steps of:
a) providing a rolled collagen carrier prepared according to the process of the invention,
b) un-packing said rolled collagen carrier from said suitable container,
c) passing said rolled collagen carrier through an access orifice, such as a trocar
d) un-rolling said rolled collagen carrier upon exit from said access orifice,
e) obtaining an unrolled rolled collagen carrier having an adhesive strength of at least 40 mmHg as measured by a pressure test (PCT), and a sterility assurance level (SAL) of $10^{-6}$.

A process according to the invention, wherein said rolled collagen carrier has a loss of coating immediately after un-rolling of less than 0.6 mg/cm² as measured by weighing.

An embodiment of the invention relates to a process according to the invention, wherein said rolled collagen carrier has an adhesive strength of at least 50 mmHg as measured by a pressure test (PCT) after un-rolling.

An embodiment of the invention relates to a process according to the invention, wherein said rolled collagen carrier has an adhesive strength of at least 60 mmHg as measured by a pressure test (PCT) after un-rolling.

Another aspect of the invention relates to a rolled compressed collagen carrier prepared according to the process of the invention, said rolled compressed collagen carrier having a coating comprising solid fibrinogen and solid thrombin that is evenly distributed and fixed upon said collagen carrier, and having at least one of the following physical properties:
I. a diameter of at the most 10 mm
II. an adhesive strength of at least 40 mmHg as measured upon un-rolling by a pressure test (PCT)
III. a sterility assurance level (SAL) of $10^{-6}$.

An embodiment of the invention relates to a rolled compressed collagen carrier according to the invention, wherein said coating comprises solid human fibrinogen in an amount of about 5.5 mg/cm² and solid human thrombin in an amount of about 2.0 IU/cm².

An embodiment of the invention relates to a rolled compressed collagen carrier according to the invention, wherein said collagen carrier has a diameter of at the most 8 mm.

An embodiment of the invention relates to a rolled compressed collagen carrier according to the invention, wherein said coating is externally oriented.

An embodiment of the invention relates to a rolled compressed collagen carrier according to the invention, wherein said coating is internally oriented.

An embodiment of the invention relates to a rolled compressed collagen carrier according to the invention, wherein said drying results in said collagen carrier comprising no more than 2.0% w/w (residual) ethanol.

An embodiment of the invention relates to a rolled compressed collagen carrier according to the invention comprising no more than 1.6% w/w (residual) ethanol.

An embodiment of the invention relates to a rolled compressed collagen carrier according to the invention comprising no more than 8.0% w/w (residual) water.

An embodiment of the invention relates to a rolled compressed collagen carrier according to the invention comprising no more than 5.0% w/w (residual) water.

An embodiment of the invention relates to a rolled compressed collagen carrier according to the invention, wherein said collagen carrier has been irradiated by gamma radiation.

An embodiment of the invention relates to a rolled compressed collagen carrier according to the invention, wherein said collagen carrier has an adhesive strength of at least 50 mmHg as measured by a pressure test (PCT) after un-rolling said collagen carrier.

An embodiment of the invention relates to a rolled compressed collagen carrier according to the invention, wherein said collagen carrier has an adhesive strength of at least 60 mmHg as measured by a pressure test (PCT) after un-rolling said collagen carrier.

An embodiment of the invention relates to a product according to the invention, wherein said rolled compressed collagen carrier is at least partly mechanically processed, thereby providing an at least partly mechanically rolled compressed collagen carrier, such as a mechanically rolled compressed collagen carrier.

An aspect of the invention relates to a rolled compressed collagen carrier obtainable by a process comprising the steps of
  a. providing a collagen carrier having a coating comprising solid fibrinogen and solid thrombin that is evenly distributed and fixed upon said collagen carrier,
  b. optionally humidifying at least part of said collagen carrier providing an optionally humidified collagen carrier,
  c. compressing said optionally humidified collagen carrier providing a compressed collagen carrier,
  d. rolling said compressed collagen carrier,
  e. obtaining a rolled compressed collagen carrier
  f. optionally drying the rolled compressed collagen carrier of step e),
  g. optionally sterilizing said rolled compressed collagen carrier of step e) or f),
  h. optionally packing said rolled compressed collagen carrier of step e), f) or g) into a suitable container
and thereby obtaining a rolled compressed collagen having at least one of the following physical properties:
  I. a diameter of at the most 10 mm
  II. an adhesive strength of at least 40 mmHg as measured by a pressure test (PCT) after un-rolling of said collagen carrier
  III. a sterility assurance level (SAL) of $10^{-6}$.

An embodiment of the invention relates to a rolled compressed collagen carrier obtainable by a process according to the invention, wherein said rolled compressed collagen carrier is at least partly mechanically processed, thereby providing an at least partly mechanically rolled compressed collagen carrier, such as a mechanically rolled compressed collagen carrier.

An aspect of the invention relates to an unrolled rolled compressed collagen carrier according to the invention having at least one of the following physical properties:
  I. a thickness of at the most 4 mm
  II. an adhesive strength of at least 40 mmHg as measured by a pressure test (PCT)
  III. a sterility assurance level (SAL) of $10^{-6}$
  IV. said rolled compressed collagen carrier is capable of adhering to the tissue while being unrolled without recoiling.

An embodiment of the invention relates to an unrolled rolled compressed collagen carrier according to the invention, wherein said unrolled rolled compressed collagen carrier is at least partly mechanically processed, thereby providing an unrolled at least partly mechanically rolled compressed collagen carrier, such as an unrolled mechanically rolled compressed collagen carrier.

An aspect of the invention relates to an unrolled rolled compressed collagen carrier according to the invention having a coating comprising solid fibrinogen and solid thrombin evenly distributed and fixed upon said collagen carrier, and having at least one of the following physical properties:
  I. a thickness of at the most 4 mm
  II. an adhesive strength of at least 40 mmHg as measured by PCT chamber
  III. a sterility assurance level (SAL) of $10^{-6}$
  IV. said rolled compressed collagen carrier is capable of adhering to the tissue while being unrolled without recoiling An embodiment of the invention relates to an unrolled rolled compressed collagen carrier according to the invention, wherein said unrolled rolled compressed collagen carrier is or has been at least partly mechanically processed, thereby providing an unrolled at least partly mechanically rolled compressed collagen carrier, such as an unrolled mechanically rolled compressed collagen carrier.

An aspect of the invention relates to a compressed collagen carrier according to the invention having a coating comprising solid fibrinogen and solid thrombin that is evenly distributed and fixed upon said collagen carrier, and having at least one of the following physical properties:
  I. a thickness of at the most 4 mm
  II. an adhesive strength of at least 40 mmHg as measured by a pressure test (PCT)
  III. a sterility assurance level (SAL) of $10^{-6}$.

An embodiment of the invention relates to a compressed collagen carrier according to the invention, wherein said compressed collagen carrier is at least partly mechanically processed, thereby providing an at least partly mechanically compressed collagen carrier, such as a mechanically compressed collagen carrier.

An further aspect of the invention relates to a rolled collagen carrier according to the invention having a coating comprising solid fibrinogen and solid thrombin that is evenly distributed and fixed upon said collagen carrier, and having at least one of the following physical properties:
  I. a diameter of at the most 10 mm
  II. an adhesive strength of at least 40 mmHg as measured by a pressure test (PCT) after un-rolling of said collagen carrier
  III. a sterility assurance level (SAL) of $10^{-6}$.

An embodiment of the invention relates to a rolled collagen carrier according to the invention, wherein said rolled collagen carrier is at least partly mechanically processed, thereby providing an at least partly mechanically rolled collagen carrier, such as a mechanically rolled collagen carrier.

Delivery of the Rolled/Coiled Collagen Carrier According to the Present Invention to the Target Location One aspect of the present invention relates to a method for delivering the coiled collagen carrier according to the present invention to a target location. Said method comprises the step of passing said coiled collagen carrier through an orifice or access tube to the target location. Any suitable instrument or device, or even the medical practitioner's hand, may be used for passing the coiled collagen carrier through the orifice or access tube. Suitable instruments can e.g. be one or more of: surgical scissors, graspers, forceps, dissectors or retractors.

In one embodiment of the present invention, an access tube is used, and it is preferably dry (i.e. contains no moisture). Said access tube is preferably a surgical trocar, such as a disposable trocar. By "target location" is preferably meant any location to which it is desired to contact and/or adhere the coiled collagen carrier of the present invention. In one embodiment the target location is a synthetic surgical model for demonstration/educational purposes. The target location can in another embodiment be an organ or tissue. In one embodiment of the present invention the target location is an organ or tissue which has been isolated from a human or animal, such as a pig. In another embodiment of the present invention said target location is in vivo in a human or animal, such as e.g. an organ (for example selected from the group consisting of: lung, kidney, liver, blood vessel) or e.g. any of but not limited to the organs listed in earlier herein in the definitions section.

Figure 7:
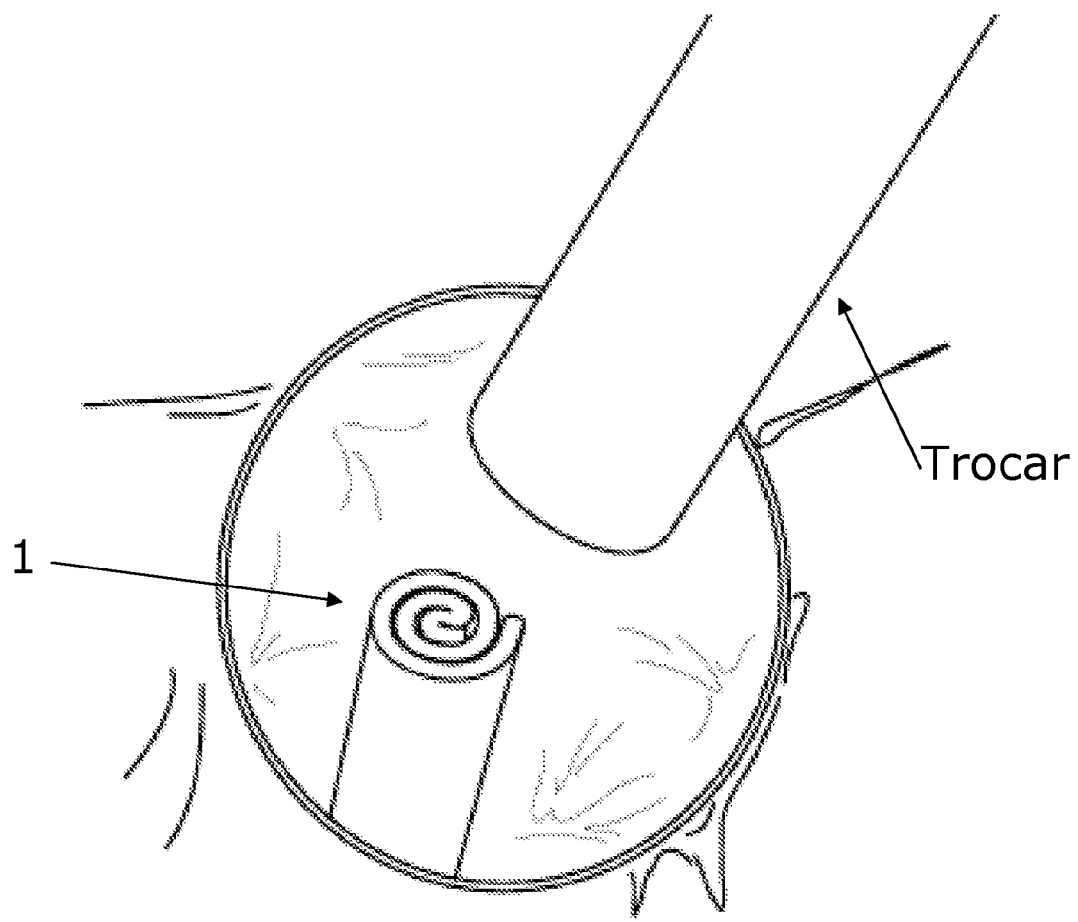
FIG. 7 shows an example of how a coiled collagen carrier is applied inside e.g. a cavity or hole in an organ or tissue, such as in lung surgery. An application member is shown in the upper right part of the figure.
Figure 8:
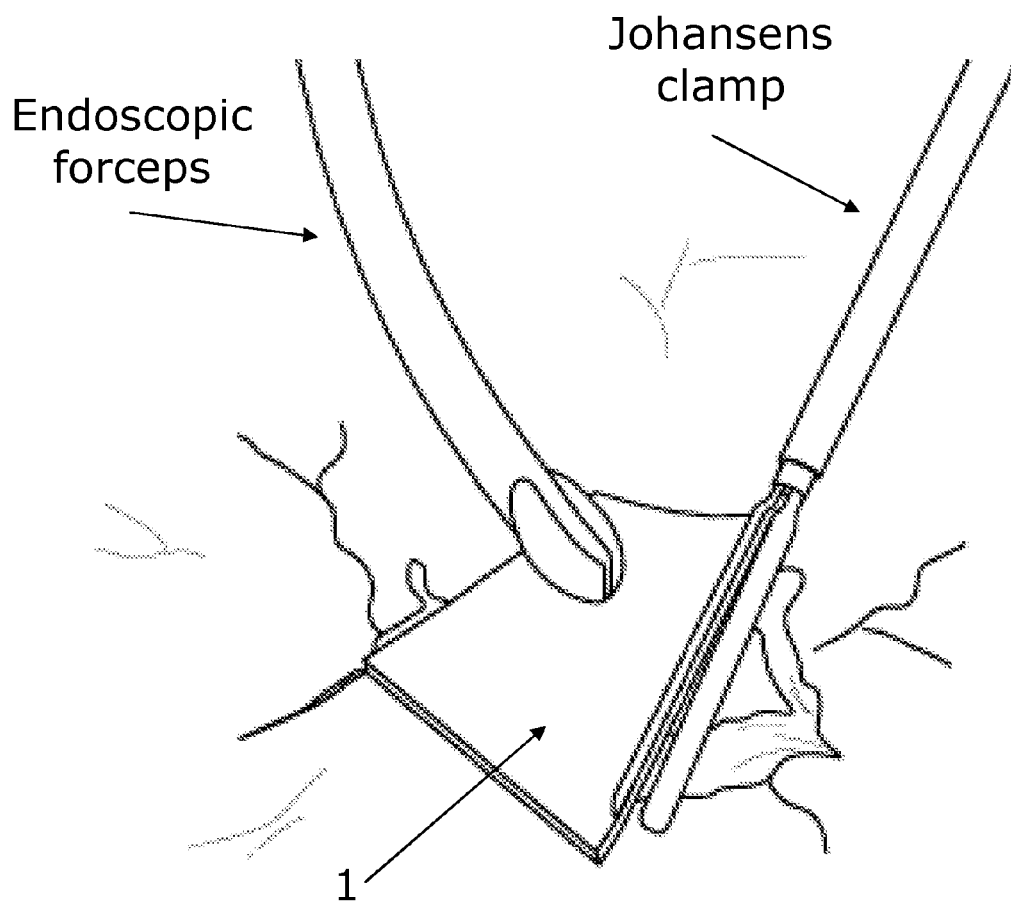
FIG. 8 shows an un-rolled coiled collagen carrier onto a target location in an organ or tissue, such as in lung surgery. The un-rolled collagen carrier is abutted and maintained to the target location using forceps. An application member is shown to the left in the picture.

After delivery to the target location the coiled collagen carrier can be maintained in the coiled state and not unrolled. This can be advantageous for example in the case of applying the coiled collagen carrier inside e.g. a cavity or hole in an organ or tissue, such as in lung surgery as e.g. illustrated in FIG. 7. In another embodiment of the present invention, the method for delivering the coiled collagen carrier further comprises the step of un-rolling the coiled collagen carrier before or during the application onto the target location. This unrolling step can for example be carried out by abutting and maintaining the edge of the coiled collagen carrier to the target location as e.g. illustrated in FIG. 8. In another embodiment of the present invention, the coiled collagen carrier is uncoiled prior to contacting the target location as e.g. illustrated in FIG. 10. In another embodiment of the present invention, the coiled collagen carrier is packed in a sterile plastic bag with a minimal amount of air inside especially suited for protecting the coiled collagen carrier from being activated by bodily fluids when using it in e.g. surgery. This is also illustrated in FIG. 10 although the plastic bag type shown is a large one compared to the ones preferably used. The preferred used sterile plastic bag with a minimal amount of air inside may optionally be used after having un-packed the packed coiled collagen carrier according to the invention but prior to passing the coiled collagen carrier through the orifice or access tube.

One or more guiding device(s) suitable for guiding the un-coiling of the coiled collagen carrier may be used to guide the uncoiling process, such as any suitable standard surgical instrument, such as any suitable endoscopic instrument. In another embodiment, a specific uncoiling device may be used, suitable for e.g. gripping the coiled collagen carrier at one end and unrolling it at the other end. In one preferred embodiment, the coiled collagen carrier is gripped at one end with a guiding device (such as a pair of grip tongs or graspers or forceps), and another guiding device (such as a pair of graspers) is used to carefully unroll the collagen carrier onto the target location.

In one embodiment of the present invention, the collagen carrier is positioned at the target site using at least one grasper. Optionally, a further guiding device is used to guide the unrolling process, such as by using a second instrument such as graspers.

In one embodiment of the present invention, the coiled collagen carrier is used in open surgery. For open surgery applications, the coiled carrier can for example be uncoiled using e.g. the medical practitioner's hands or any standard surgical instrument, such as one or more of: surgical scissors, graspers, forceps, dissectors or retractors.

Figure 9:
FIG. 9 shows the moistening of a coiled collagen carrier (in an uncoiled state) applied inside e.g. a cavity or hole in an organ or tissue, such as in lung surgery. The moistening is performed using e.g. saline solution, and/or the application of pressure on the collagen carrier using saline-moistened swabs or wipes.

During the unrolling/uncoiling process for a coated collagen carrier, the guiding device, surgical instrument or medical practitioner's hand(s) should preferably only contact the non-coated side of the collagen carrier to prevent damage to the coating side. During and after the unrolling process at the target location, the surgeon may choose to further moisten the collagen carrier using e.g. saline solution, and/or to apply pressure on the collagen carrier, for example using the medical practitioner's hand or a swab or wipe, such as a moistened swab or wipe, optionally applied using e.g. a grasper. Optional moistening of the collagen carrier using a rinsing/sucking/spraying system may also be applied. In one embodiment, multiple moistened swabs or wipes are applied (for example, applied using multiple graspers), such as using two moistened swabs or wipes applied using two sets of graspers as e.g. illustrated in FIG. 9. If pressure is applied to the collagen carrier after application to the target location, this can for example be for between 30 seconds and 6 minutes, such as e.g. for 1-5 minutes, such as for example for 3-5 minutes or for 2-3 minutes or for 2 minutes or for 3 minutes. Multiple cycles of moistening and compression can be applied to the collagen carrier. In case the bleeding is not fully stopped by application of one collagen carrier, further collagen carriers can be applied, for example 1 or 2 further collagen carriers.

Preferably, if a coated collagen carrier (such as Tacho-Sil®) is used in the unrolling process, the collagen carrier is unrolled with the coated side of the collagen carrier facing the target location.

After delivery to the target site the collagen carrier will preferably adhere to the target site and cause haemostasis to occur at and around the target site. Any swabs or wipes used are preferably removed carefully, optionally while holding the collagen carrier in place using a suitable surgical instrument, such as a pincet or graspers.

In one preferred embodiment of the unrolling method, all objects contacting the coiled collagen carrier before the collagen carrier contacts the target location (for example: surgical gloves, surgical instruments and the access tube or orifice) are dry and contain no moisture or fluids. It is also preferred that the collagen carrier remains dry until application to the target area. This can e.g. be achieved either by very precise and careful manipulation of the collagen carrier or by keeping the collagen carrier inside a plastic bag up until delivery to the target location. Thus in one embodiment of the present invention the coiled collagen carrier is delivered to the target location in a sterile plastic bag with a minimal amount of air inside. The coiled collagen carrier may have been pre-packed in a sterile plastic bag with a minimal amount of air inside in the product packaging, or alternatively the collagen carrier may be inserted into the sterile bag after removal from the product packaging. The plastic bag can be removed after the collagen carrier reaches the target location.

A sterile plastic bag with a minimal amount of air inside may be used to apply pressure to the collagen carrier after application to the target site. This plastic bag may optionally be a part of the original product packaging, i.e. in one embodiment of the present invention, the coiled collagen carrier is pre-packed in a sterile plastic bag with a minimal amount of air inside.

In one embodiment of the herein-described unrolling/delivery method, the collagen carrier roll has an outer diameter of not more than 12 mm and wherein the orifice or access tube (such as a trocar), has a diameter of not more than 12 mm. The un-rolling/delivery method may furthermore comprise the step of un-packing the coiled collagen carrier from the container. This can for example be done using an un-packing device and/or gloved hands.

In particular, the rolled/coiled collagen carrier of the present invention is for use in therapy and/or a method of surgery, such as e.g. practised on the human or animal body. The terms "surgery" and "method of surgery" are used interchangeably herein. Thus, one embodiment of the present invention relates to the coiled collagen carrier according to the present invention for use in therapy.

Another embodiment of the present invention relates to the coiled collagen carrier according to the present invention for use in surgery.

For this therapy and/or method of surgery it is preferred to use at least some (or all) of the features of one or more of the methods for delivering the coiled collagen carrier to a target location as described herein.

One embodiment of use of the coiled collagen carrier of the present invention for use in therapy and/or a method of surgery is a method of arresting haemorrhage associated with performing minimally invasive surgery using the coiled collagen carrier according to the present invention. Another embodiment is a method of treating injury associated with performing minimally invasive surgery using the coiled collagen carrier according to the present invention. Another embodiment is a method of treating injury associated with performing endoscopic treatment, laparoscopy treatment, or thoracoscopy treatment using the coiled collagen carrier according to the present invention. Another embodiment is a method of treating and/or preventing injury associated with performing endoscopic surgery using the coiled collagen carrier according to the present invention. Another embodiment is a method of treating or preventing hemorrhage in human or animal tissue or a tissue sample in need of haemostasis using the coiled collagen carrier according to the present invention. Another embodiment is a method of treating human or animal tissue or a tissue sample in need of sealing and/or glueing using the coiled collagen carrier according to the present invention. Another embodiment is use of the coiled collagen carrier according to the present invention in keyhole surgery. Another embodiment is use of the coiled collagen carrier according to the present invention in open surgery, wherein the coiled collagen carrier can either be administered and left uncoiled in vivo, or wherein the collagen carrier is uncoiled (for example. using e.g. two or more sets of ordinary surgical graspers). A further embodiment is a method of treating human or animal tissue or a tissue sample in need of coverage to prevent the development of post-surgical tissue adhesions. Another embodiment is use of the coiled collagen carrier according to the present invention in endoscopy, laparoscopy, or thoracoscopy.

Examples of suitable surgical procedures include but are not limited to: colon resection, cryotherapy of the kidney, partial nephrectomay, lung surgery, video-assisted thoracoscopic surgery, liver resection surgery, hypodermic injection, air-pressure injection, subdermal implants, endoscopy, percutaneous surgery, laparoscopic surgery, thoracoscopic surgery arthroscopic surgery, cryosurgery, microsurgery, keyhole surgery, endovascular surgery (such as angioplasty), coronary catheterization, permanent spinal and brain electrodes, stereotactic surgery, The Nuss Procedure, radioactivity-based medical imaging methods, such as gamma camera, Positron emission tomography and SPECT (single photon emission tomography), image-guided surgery, robotic surgery, interventional radiology, esophagogastroduodenoscopy, enteroscopy, colonoscopy, sigmoidoscopy, magnification endoscopybile duct endoscopic retrograde cholangiopancreatography (ERCP), duodenoscope-assisted cholangiopancreatoscopy, intraoperative cholangioscopy, rectoscopy, proctoscopy, rhinoscopy, bronchoscopy, otoscope, cystoscopy, gynoscopy, colposcopy, hysteroscopy, falloposcopy, laparoscopy, arthroscopy, thoracoscopy, mediastinoscopy, amnioscopy, fetoscopy, plastic surgery panendoscopy, laryngoscopy, esophagoscopy, bronchoscopy, orthopedic surgery, hand surgery (such as endoscopic carpal tunnel release and epidural space (epiduroscopy)).

Preferably, the rolled/coiled collagen carrier of the present invention is for use as supportive therapy in surgical procedures or as a prophylactis adjunct therapy in surgical procedures. The rolled/coiled collagen carrier of the present invention can also be used as an adjunct to haemostasis for use in surgery (such as e.g. cardiovascular surgery), such as when control of bleeding by standard surgical techniques (such as sututre, ligature or caurtery) are ineffective or impractical. For example, the coiled collagen carrier can be used for improvement of haemostasis and/or to promote tissue sealing, and/or for suture support (such as in vascular surgery).

A further aspect of the invention relates to a rolled compressed collagen carrier according to the invention for use in tissue sealing, tissue gluing and haemostasis.

An aspect of the invention relates to a rolled compressed collagen carrier according to the invention for use in minimally invasive surgery.

An aspect of the invention relates to a rolled compressed collagen carrier according to the invention for use in endoscopic surgery.

An embodiment of the invention is to provide an at least partly mechanically rolled compressed collagen carrier according to the invention for use in tissue sealing, tissue gluing and haemostasis.

An embodiment of the invention is to provide an at least partly mechanically rolled compressed collagen carrier according to the invention for use in minimally invasive surgery.

An embodiment of the invention is to provide an at least partly mechanically rolled compressed collagen carrier according to the invention for use in endoscopic surgery.

An aspect of the invention is to provide an unrolled rolled compressed collagen carrier according to the invention for use in tissue sealing, tissue gluing and haemostasis.

An aspect of the invention is to provide an unrolled rolled compressed collagen carrier according to the invention for use in minimally invasive surgery.

An aspect of the invention is to provide an unrolled rolled compressed collagen carrier according to the invention for use in endoscopic surgery.

An embodiment of the invention is to provide an unrolled at least partly mechanically rolled compressed collagen carrier according to the invention for use in tissue sealing, tissue gluing and haemostasis.

An embodiment of the invention is to provide an unrolled at least partly mechanically rolled compressed collagen carrier according to the invention for use in minimally invasive surgery.

An embodiment of the invention is to provide an unrolled at least partly mechanically rolled compressed collagen carrier according to the invention for use in endoscopic surgery.

An embodiment of the invention relates to a method for prevention or treatment of tissue in need of sealing and/or gluing, the method comprising applying a rolled compressed collagen carrier according to the invention to said tissue in need thereof.

An embodiment of the invention relates to a method for prevention or treatment of bleeding in tissue in need of haemostasis, the method comprising applying a rolled compressed collagen carrier according to the invention to said tissue in need thereof.

An embodiment of the invention relates to a method for prevention or treatment of injury associated with performing minimally invasive surgery, the method comprising applying a rolled compressed collagen carrier according to the invention to said injury in need thereof.

An embodiment of the invention relates to a method for prevention or treatment of injury associated with performing endoscopic treatment, laparoscopy treatment, or thoracoscopy treatment, the method comprising applying a rolled compressed collagen carrier according to the invention to said injury in need thereof.

An embodiment of the invention relates to the use of a rolled compressed collagen carrier according to the invention for the preparation of a medicament for the prevention or treatment of tissue in need of sealing and/or gluing.

An embodiment of the invention relates to the use of a rolled compressed collagen carrier according to the invention for the preparation of a medicament for the prevention or treatment of bleeding in tissue in need of haemostasis.

An embodiment of the invention relates to the use of a rolled compressed collagen carrier according to the invention for the preparation of a medicament for the prevention or treatment of injury associated with performing minimally invasive surgery.

An embodiment of the invention relates to the use of a rolled compressed collagen carrier according to the invention for the preparation of a medicament for the prevention or treatment of injury associated with performing endoscopic treatment, laparoscopy treatment, or thoracoscopy treatment.

Another aspect of the invention relates to a rolled compressed collagen carrier according to the invention for use in the prevention or treatment of tissue in need of sealing and/or gluing.

An aspect of the invention relates to a rolled compressed collagen carrier according to the invention for use in the prevention or treatment of bleeding in tissue in need of haemostasis.

A further aspect of the invention relates to a rolled compressed collagen carrier according to the invention for use in the prevention or treatment of injury associated with performing minimally invasive surgery.

Still another aspect of the invention relates to a rolled compressed collagen carrier according to the invention for use in the prevention or treatment of injury associated with performing endoscopic treatment, laparoscopy treatment, or thoracoscopy treatment.

A further embodiment of the invention relates to a coiled collagen carrier according to the invention for use in the prevention or treatment of hemorrhage in human or animal tissue or a tissue sample in need of haemostasis.

A further embodiment of the invention relates to a coiled collagen carrier according to the invention for use in the prevention or treatment of injury associated with performing minimally invasive surgery.

A further embodiment of the invention relates to a coiled collagen carrier according to the invention for use in the prevention or treatment of injury associated with performing endoscopic treatment, laparoscopy treatment, or thoracoscopy treatment.

A further embodiment of the invention relates to a coiled collagen carrier according to the invention for use in the prevention or treatment of injury associated with performing endoscopic surgery.

A further embodiment of the invention relates to a coiled collagen carrier according to the invention for use in the prevention or treatment of post-surgical tissue adhesions.

A further embodiment of the invention relates to a coiled collagen carrier according to the invention for use in the prevention or treatment of post-surgical tissue adhesions in human or animal tissue or a tissue sample in need of coverage.

A further embodiment of the invention relates to a coiled collagen carrier according to the invention for use in the prevention or treatment of tissue or a tissue sample in need of sealing/glueing.

It should be noted that embodiments and features described in the context of one of the aspects of the present invention also apply to the other aspects of the invention i.e. all aspects relating to a rolled compressed collagen carrier also apply to a compressed collagen carrier, or a rolled collagen carrier, or an unrolled rolled compressed collagen carrier.

All patent and non-patent references cited in the present application, are hereby incorporated by reference in their entirety.

The invention will now be described in further details in the following non-limiting examples.

Apparatus

Figure 11:
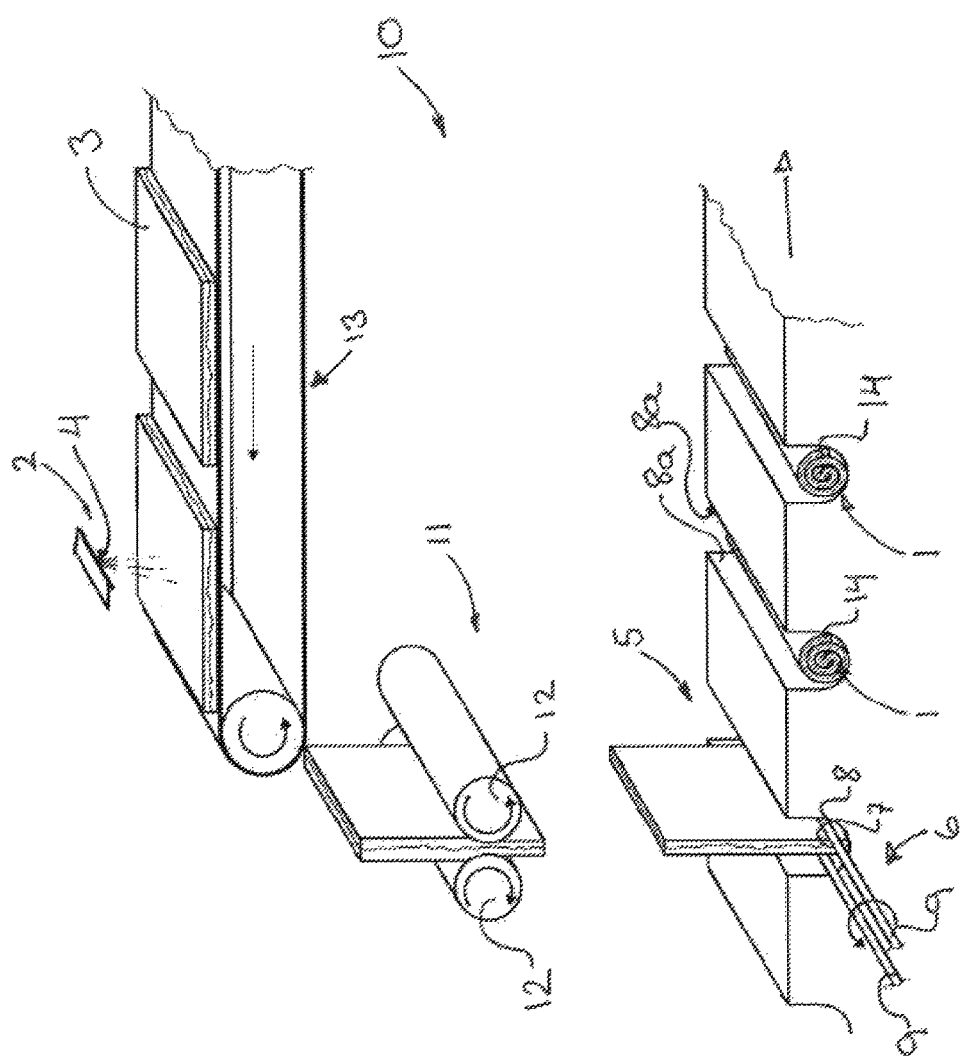
FIG. 11 discloses schematically a preferred embodiment of an apparatus for providing coiled collagen carrier according to the present invention.

Reference is made to FIG. 11, which shows schematically a preferred embodiment of an apparatus 10 for providing a coiled collagen carrier. The apparatus comprising a number of elements as shown in the figure and comprises in particular a device for applying moisture 2 to a collagen carrier 3 prior to coiling of a collagen carrier as disclosed herein.

The device for applying moisture 2 comprising a spray nozzle 4 directed towards the surface of the coating layer of the collagen carrier, the spray nozzle 4 provides droplets as a mist or a spray of solvent. Thus, the collagen carrier is orientated with its coating surface facing upwardly towards the spray nozzle 4. The solvent penetrates into the collagen carrier 3 and softens the collagen carrier 3. It has been found that, it may be sufficient to humidify only the coating layer or a upper part thereof of the collagen carrier, although it may be preferred to soak the whole collagen carrier 3, that is soaking both the coating layer and the collagen layer.

The apparatus 10 further comprises a coiling device 5, which is adapted to grip the moisturised collagen carrier 3 along an edge and coil it into a coiled collagen carrier 1. The coiling device 5 comprises rotatable gripping means 6 for gripping the collagen carrier along an edge 7 of the collagen carrier 3 and coil the collagen carrier 3 by rotation of the gripping means 6 around an axis being parallel to the longitudinal extension of the gripping means 6.

Gripping along the edge 7 and rotating the gripping means 6 may not provide a coiling or a coiled collagen carrier 1 having a desired shape if the collagen carrier is not supported during coiling. To assure coiling and assist in defining the shape of the coiled collagen carrier 1, the coiling device 5 further comprises a support device 8 supporting the collagen carrier while being coiled. The support device 8 is typically a cavity arranged relatively to the gripping means 6 so that the surface of the support device 8 acts as counter pressure means by at least a part of the collagen carrier 3 abuts at least a part of the inner surface of the cavity during coiling. As mentioned, the shape of the surface of the support device at least assists in defining the shape of the coiled collagen carrier 1.

The gripping device 6 comprises a pair of elongated members 9, such as a pair of tweezers or pincers. The elongated members 9 has a longitudinal extension matching the width of the collagen carrier 1—the width of the collagen carrier is considered to be the dimension parallel to the extension of the elongated members 9—whereby the collagen carrier is gripped at the edge along the whole width by the elongated members 9.

Gripping of the collagen carrier 3 is accomplished by decreasing the distance between the two elongated members 9 once the collagen carrier 3 is located in between the elongated members 9 to an extent providing a gripping being sufficient to provide coiling once the elongated members 9 are rotated.

As shown in FIG. 11, the support device 8 is a cavity comprising a bottom part shaped as a segment of a cylinder having at least one open end through which the elongated members extend, and wherein the curved part of the cylinder segment extends at least 180°. The upper part of the cavity is constituted by two parallel straight wall segments 8a so that the cavity has the shape of an open channel.

The elongated members 9 of the gripping device 6 extend into the cavity of the support device 8 through the open end. The elongated members 9 are furthermore extractable so that once the collagen carrier 3 has been coiled and is located in the cavity of the support device 8, the elongated members 9 are extracted from the coiled collagen carrier 1. The elongated members 9 are extracted in a direction being parallel to the longitudinal extension of members. When another collagen carrier 3 is to be coiled, the elongated members 9 are introduced back into the cavity of the support device 8 by moving the elongated members 9 in the opposite direction than during the extraction.

As indicated in FIG. 11, the result of the coiling is an coiled collagen carrier in the form of elongated member with an S-shaped core. The two curves of the "S" is defined by the elongated members 9. Furthermore, the rotation of the gripping device 6 is adapted to arrange the edge 14 so that it abuts the wall of the cavity which fixate the edge 14 relatively to the remainder of the coiled collagen carrier 1.

The apparatus 10 further comprises a compressing device 11. The compressing device 11 being arranged to compress the moisturised collagen carrier 3 prior to coiling of the moisturised collagen carrier, that is as indicated in FIG. 11, the compressing device being arranged after the device for applying moisture 2 and before the coiling device 5.

The compressing device comprises a pair of rollers 12 arranged to compress the moisturised collagen carrier 3 prior to coiling of the moisturised collagen carrier. The compression being provided because the gap in between the rollers is smaller than the thickness of the moisturised collagen carrier. As indicated in FIG. 11, the rollers 12 rotate in opposite directions so as to transport the collagen carrier through the pair of rollers 12 towards the coiling device 5.

After the collagen carrier 3 has been coiled into a coiled collagen carrier it is still moisturised (contains solvent) and is still softened. To provide a form-stable coiled collagen carrier 1, the collagen carrier is de-moisturised which is provided by drying the coiled collagen carrier 1. The apparatus accordingly further comprising at least a drying means (not shown in the figure) for drying one or more coiled collagen carriers subsequently to the coiling.

The drying means may typically be embodied as a drying tunnel through which the coiled collagen carrier 1 passes and inside which drying tunnel the temperature is elevated relatively to the temperature of the coiled collagen carrier 1 and the relative solvent content in the air is kept low. These two measures (elevated temperature and low relative solvent content) promote transport of solvent from the coiled collagen carrier 1 to the air inside the drying tunnel. Forced circulation of the air may advantageously be applied to enhance removal of solvent from the coiled collagen carrier 1.

The apparatus is advantageously embodied so as to provide an automated production of coiled collagen carriers 1. As indicated in FIG. 11, the apparatus is embodied as an assembly line which conveys the collagen carriers 3 through the various production stages.

Thus, apparatus 10 comprises a first conveyer device 13 which conveys collagen carriers 3 prior to coiling past the moisturiser device 2 and to the coiling device 5.

On its way from the moisture device 2 and to the coiling device 5, the moisturised collagen carriers 3 pass through the pair of rollers 12 arranged to compress the moisturised collagen carrier prior to coiling of the moisturised collagen carrier, and the first conveyer device 13 conveys the moisturised collagen carriers 3 to the pair of rollers 12. It is noted that conveying of the moisturised collagen carrier 3 from the end of the first conveyer device 13 and to the gap between the pair of rollers 12 can be assisted by guides (not shown) which guides the moisturised collagen carriers 3 to the pair of rollers 12. As a compression is performed by the pair of rollers 12, the rotation of the rollers 12 conveys the moisturised collagen carrier 3 through the compression device 11 and to the coiling device 5. Again, suitable guiding means (not shown) may be applied to guide the collagen carriers 3 to the position in the cavity of the coiling device 5 in which the gripping means 6 may grip the collagen carrier along an edge and coil the collagen carrier 3. The guides and guiding means are made from an inert material that does not contaminate the collagen carriers by e.g. rubbing off of material.

Furthermore, to assist the automated production of coiled collagen carriers 1, the cavity of the coiling device 5 is formed in a second conveyer device. While the first conveyer device 13 conveys the collagen carrier 3 at a constant speed, the second conveyer device typically conveys coiled collagen carriers 1 step wise; that is as long as the coiling takes place, the second conveyer device is at rest and once coiling is finished (the edge 14 is arranged so as to abut the surface of cavity and the elongated members 9 extracted) the second conveyer device moves to arrange an empty cavity below the pair of rollers and in front of the extracted elongated members 9.

The conveying speed of the first conveyer device is set in accordance with the amount of solvent being applied from the nozzles 14 to obtain a predefined amount solvent applied per surface area of the collagen carrier 3.

The orientations and mutual arrangements of the various parts presented in FIG. 11 are implemented in the apparatus as implemented in the figure. That is, the first conveyer device 13 is arranged above the coiling device 5 with the pair of rollers 12 arranged in between.

Contamination of the collagen carriers is often an issue that must be taken care of during humidification, compression, coiling and drying. To avoid contamination, the various parts used for producing the coiled collagen carrier are shielded from the environment by a cabinet. Thus, the apparatus may typically comprise a cabinet sealing the moisturiser device 2, and/or the pair of rollers 12, and/or the coiling device 5, and/or the support device 8, and/or the first 13 and/or the second conveyer device.

Processes

The apparatuses disclosed herein are adapted to perform a process for coiling a collagen carrier comprising a collagen layer and a coating layer comprising mostly solid fibrinogen and mostly solid thrombin. In the following, preferred embodiments of processes according to the present invention will be disclosed. Reference is made to FIG. 11 and the elements and parts presented therein are referenced by reference numbers—this is not intended to limit the processes to the apparatus disclosed in FIG. 11.

Processes according to the invention typically comprise the sequential steps of humidifying at least part of a collagen carrier 3, and coiling the collagen carrier 3 by gripping the collagen carrier 3 between a pair of elongated members 9, and rotating the pair of elongated members 9 about an axis being parallel to a longitudinal extension of the elongated members 9 in order to coil the collagen carrier 3 on the members, while the collagen carrier 3 is supported by a support device 8.

The humidifying and coiling steps are preferably executed as two separate steps as disclosed above in relation to the embodiment of the apparatus 10, which steps are executed consecutively to each other. The time between humidifying and coiling is selected so that the softening effect obtained by the humidification on the collagen carrier 3 is present while the collagen carrier 3 is coiled.

After the collagen carrier 3 has been coiled, the process involves a step of drying the coiled collagen carrier 1. The drying steps removes solvent from the coiled collagen carrier and the drying step is typically and preferably performed while the coiled collagen carrier is supported so as to maintain its coiled shape during drying. The result of the process is a form-stable coiled collagen carrier 1.

The coiling is performed by gripping the collagen carrier using at least one gripping device and the collagen carrier is gripped along an edge of the collagen carrier 3. The coiling is performed by gripping the collagen carrier using at least one pair of tweezers or pincers 9.

Drying of the coiled collagen carrier 1 is typically performed by blowing air with humidity lower than the coiled collagen carrier and optionally applying heat to the air to enhance e.g. evaporation of the liquid used to humidify the collagen carrier 3. It is noted that the term humidity is to be understood broadly and not limited only to water. For instance, humidity is also used to cover the concentration in the air of the solvent used to humidify the collagen carrier 3.

As noted above, the process involves humidifying at least a part of the collagen carrier and in some embodiments of the invention the part being humidified is the coating layer. Typically, the humidification step is performed by spraying droplet of liquid onto the surface of the coating layer, and the humidification is obtained by the liquid penetrating into the coating layer of the collagen carrier 3 e.g. by a capillary action. Thus, the amount of liquid present in e.g. the coating layer may vary with the depth; however, as one aim of humidifying is to soften the collagen carrier 3 such variations in liquid amounts are acceptable. In many preferred embodiment, the coating layer has been humidified using a solvent applied onto the surface of the coating layer in an amount 1.2-10.75 mg/cm$^2$ surface of collagen carrier 3. The solvent used typically comprises or consists of ethanol.

A process according to the present invention may further comprise a step of compressing the collagen carrier 3 which compression reduces the thickness of the collagen carrier. While different compression ratio, i.e. ratio between the thickness of the collagen carrier 3 before and after compression, may vary, the collagen carrier is preferably compressed with a compression ratio between 6 and 12. The compression is performed after the humidifying step and before the coiling step, that is the compression is performed prior to coiling of the collagen carrier.

An efficient compression has proven to be performed by passing the humidified collagen carrier through a set of rollers 12 having a gap size being smaller than the thickness of the collagen carrier 3 before passing through the set of rollers 12. The gap size is selected so as to provide the desired compression ratio. Typically and preferred numbers for the gap size is no more than 0.5, preferably no more than 0.6 or between 0.5-1.0 mm, or no more than 0.75 mm. However, the gap size should be selected in accordance with the thickness of the collagen carrier 3 so as to obtain the desired compression ratio.

After the collagen carrier 3 has been humidified, optionally compressed and coiled, the coiled collagen carrier 1 is still softened and may have a tendency to un-coil during drying e.g. due to gravity effects and/or some mechanical tension in coiled collagen carrier 1. To assure that the coiled collagen carrier 1 hardens in the coiled shape, the edge (see number 14 in FIG. 11) of the coiled collagen carrier 1 arranged on the outside of the coil after coiling is abutting the surface of the cavity and thereby being fixated by the support device 8 relatively to the coiled collagen carrier 1 during drying.

Once the coiled collagen carrier 1 has dried the softened parts of the collagen carrier has hardened and the coiled collagen carrier 1 is form-stable.

The support device 8 is as disclosed above with reference to FIG. 11 a cavity having a bottom part shaped as a segment of a cylinder having at least one open end through which the elongated members extend into the cavity, and wherein the curved part of the cylinder segment extends at least 180°. During the coiling process, the outer edge 14 of the collagen carrier is arranged inside the part of the cavity formed as a segment of cylinder and the edge 14 abuts the inner surface of the cavity. Once the edge 14 abuts the inner surface, the coiling process is terminated and the gripping means in the form of a pair of elongated members 9 is extracted from the coiled collagen carrier through the open end of the cavity.

Extraction of the elongated members 9 from the coiled collagen carrier 1 may involve securing of the coiled collagen carrier 1 inside the cavity if the elongated members 9 do not slide easily out from the coiled collagen carrier 1. Such securing may be provided by mechanically pressing the coiled collagen carrier toward the bottom of the cavity while extracting the elongated members, or a lattice structure may be arranged to prevent the coiled collagen member from sliding out of the cavity through the open end of the cavity while allowing extraction of the elongated members; thereby the dragging action from the elongated members on the coiled collagen carrier 1 may be outbalanced by the lattice structure, or the pressing action.

Once the elongated members 9 are extracted, any securing may be released. The extraction of the elongated members 9 is typically performed before drying of the coiled collagen carrier. The pair of elongated members may be constituted by a pair of tweezers and the process disclosed above is the same.

The atmosphere surrounding the collagen carrier 3 and humidification device 2 while the collagen carrier 3 being humidified, compressed and coiled is typically maintained at a temperature of 18-22° C. and a relative humidity of 30-50%.

After the coiled collagen carrier 1 has been dried to form a form-stable collagen carrier, the process may include the step of arranging the form-stable coiled collagen carrier 1 in a container and subsequently sealing the container. The step of arranging the coiled collagen carrier in a sealed container prevents the coiled collagen carrier 1 from being humidified and/or contaminated. Furthermore, the step of arranging the coiled collagen carrier 1 in a sealed container may also comprise the steps of arranging the coiled collagen carrier 1 in an inner container and arranging the inner container in an outer container. In addition, a desiccator may be arranged inside the outer container prior to sealing of the container.

While an aim of the process is to provide a sterile coiled collagen carrier packed in one or more containers, the process may also include a sterilizing step during which the container(s) with coiled collagen carrier is exposed to a sterilizing process. The sterilizing may typically be radiation sterilization. To make it easy detectable whether a given coiled collagen carrier 1 has been sterilized, a label indicating whether sterilization has been carried out or not may be arranged on the outside of the outer container—or container in general.

An often preferred sterilization step comprises sterilizing the coiled collagen carrier 1 using gamma radiation. The sterilization of the coiled collagen carrier 1 is often performed to a sterility assurance level (SAL) of $10^{-6}$ using gamma radiation.

Coiled Collagen Carrier

As outlined above, the processes and apparatuses are used to produce form-stable coiled collagen carrier 1. The processes and apparatuses disclosed above have proven to be efficient to produce the coiled collagen carrier 1; however coiled collagen carriers 1 as such are considered within the scope of the present invention.

Thus, the present invention comprising a coiled collagen carrier 1 having a collagen layer and a coating layer on top of the collagen layer. The coating layer comprising mostly solid thrombin and mostly solid fibrinogen although all the thrombin and/or all the fibrinogen may be solid.

The coiled collagen carrier has typically the shape of a elongate element with a number of windings of the collagen carrier 3 about the longitudinal axis of the elongate element and at least the outer windings and preferable each winding being orientated so that the coating layer constitutes the outer surface of each the windings. A further characteristic of the coiled collagen carrier 1 is that it is form-stable and defines a collagen carrier in a coiled configuration where at least the outer windings proceed along a spiral in a cross section of the collagen carrier.

The form-stability is often provided by the collagen layer and/or the coating layer has hardened in the coiled shape whereby no additional elements such as constraints are needed to keep the coiled collagen carrier in its coiled shape.

The coiled collagen carrier 1 is in an unrolled configuration a rectangular sheet, preferably having a width, a length and a thickness of the most 4 mm, such as at the most 5 mm, preferably at the most 6 mm, such as at the most 7 mm. The coiled collagen carrier is typically coiled around the width so that the width of the coiled collagen carrier 1 is the width of the unrolled configuration. However coiled collagen carriers being coiled around the length are also an option. A coiled collagen carrier will often comprise three, four or five windings.

A preferred coiled collagen carrier 1 has a cylindrical shape with an outer diameter of less than 12 mm, such as less than 11 mm, such as less than 10 mm, such as less than 9 mm, such as less than 8 mm, such as less than 7 mm, such as less than 6 mm, such as less than 5 mm, such as less than 4 mm, such as less than 3 mm. Furthermore, the coiled collagen carrier has an s-shaped inner most winding about the longitudinal direction of the coiled collagen carrier as disclosed e.g. in FIG. 11.

The coating layer of coiled collagen carriers 1 has no through-going cracks. Often this is obtained by producing the coiled collagen carrier in a manner where the coating layer and/or the collagen layer is(are) softened by humidification prior to coiling which softening allows stretching of the coating layer and/or collagen layer without producing crack or chips (frissures) during coiling. A subsequent drying hardens the softened layer which fixes the coil shape in a form-stable shape. Preferably the coating layer is humidified.

The coiled collagen carrier 1 is often arranged in a container. The container is typically sealed to prevent contamination and/or degradation and/or to maintain form-stability of the coiled collagen carrier. A desiccant, such as silica gel, may be arranged in the container. Such containers with coiled collagen carrier 1 is considered within the scope of the invention In a particular preferred embodiment, the packed coiled collagen carrier 1 comprises an inner container and an outer container. The inner container comprises a cavity having a bottom shaped as a segment of a cylinder, and wherein the curved part of the cylinder segment extends at least 180° as disclosed in FIG. 11 numeral 8. The cavity is sealed by a tear-off or breakable foil and the outer container comprising a sealed pouch inside which the sealed inner container is arranged together with a desiccant.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

EXAMPLES

Example 1—Loss of Coating

Example 1.1—Loss of Coating Immediately after Un-Rolling

Loss of coating is determined immediately after un-rolling of a collagen carrier according to the present invention. The collagen carrier may not loose more than 0.6 mg/cm$^2$ as measured by weighing immediately after unrolling.

The un-rolling is performed by fixating one end of a pre-rolled TachoSil®, such as a coiled collagen carrier according to the present invention between the fingers of one gloved hand while the rest of the pre-rolled TachoSil®, such as a coiled collagen carrier according to the present invention is unrolled with the aid of the fingers of the often gloved hand assuring that the coating layer faces downwards upon un-rolling. The un-rolling is performed in a standard laboratory setting well known to the person skilled in the art.

Example 1.2—Loss of Coating without Unrolling

This analytical procedure describes determination of adhesion of the coating of a pre-rolled TachoSil®, such as a coiled collagen carrier according to the invention by gravimetry. In other words, the procedure describes the loss of coating of coiled collagen carrier when exposed to a controlled physical action as described below. The measurements is performed in a standard laboratory setting well known to the person skilled in the art. As standard, gloved hands are always used.

1.1 Analytical System
  Analytical balance
  Vortex mixer
  Ruler with millimetre graduations
  Reagent tube of about 2 cm internal diameter
1.2 Samples
  Unpack the pre-rolled TachoSil®, such as a coiled collagen carrier according to the invention from its package using gloved hands. Measure length and width of the sample. The sample needs to fit into the reagent tube without folding.
1.3 Performance
  Place the sample in a balanced reagent tube and shake on the vortex mixer (frequency: about 1000 rpm) for 2 minutes. Remove the sample and reweigh the residual quantity of coating material (mass of residual).

1.4 Calculation

Surface area (cm$^2$) = length [cm] × width [cm])

Abrasion (mg/cm$^2$) =

$$\frac{(\text{mass of residual [g]} - \text{tare reagent tube [g]}) \times 1000}{\text{surface area [cm}^2\text{]}}$$

Reported value: abrasion in mg/cm$^2$; values 0.1 mg/cm$^2$ are reported as 0.1 mg/cm$^2$.

The pre-rolled TachoSil®, such as a coiled collagen carrier may not lose more than 0.6 mg/cm$^2$ as measured by weighing immediately after unpacking and testing according to the analytical procedure described in this example.

Example 2—Measurement of Adherence

By the term "adherence" is meant the in vitro capability of a collagen carrier to adhere to living tissue according to the present invention. Adherence is investigated qualitatively by visual inspection of adherence of an unrolled rolled collagen carrier to a mammal tissue i.e. the capability of a collagen carrier to adhere to a tissue.

A piece of freshly slaughtered porcine liver tissue is placed in a Petri dish and a rolled collagen carrier of the present invention is placed by using gloved hands on the liver tissue while being unrolled by using gloved hands and is then subjected to light pressure by gloved hand. FIG. 1 illustrates the adherence of the unrolled collagen carrier to the living tissue.

Example 3—Measurement of Density

Determination of the density was performed by weighing the collagen fleece combined with knowledge of the size i.e. volume of the fleece making it possible to calculate the density of the collagen fleece. Standard laboratory equipment was used for measuring the weight of the collagen fleeces (note that by the "weight" of the collagen carriers is meant the weight of the collagen carrier excluding the weight of the coating layer). The average density of compressed collagen carrier are shown below in example 4. Please note that the density of a collagen carrier of the present invention is the density of the collagen carrier excluding the coating layer.

Example 4—Adhesive Strength (PCT Test)

In the following (example 4.1) an in vitro pressure test for measuring adhesive strength to a simulated tissue sample (latex membrane) of a coiled collagen carrier of the present invention is described. The test may also be used when assessing the adhesive strength of a pre-rolled TachoSil®.

Examples 4.2-4.3 demonstrate the obtained PCT-values when measuring un-rolled coiled collagen carriers of the present invention wherein the coiled collagen carriers have different average densities 3.62 mg/cm$^3$-4.05 mg/cm$^3$. Example 4.4 demonstrates the adhesive strength of a collagen carrier that has not been subjected to the humidification, compression and rolling process.

Example 4.1

Product to be tested: A pre-rolled TachoSil® or a coiled collagen carrier of the present invention. The product to be tested has a midi size i.e. 46-49 mm*46-50 mm*4-7 mm.

4.1.1 Introduction
  The protocol applies to the execution of a Pressure Chamber Test (PCT) to determine the adhesiveness of a coiled collagen carrier of the present invention or a pre-rolled TachoSil®, to a latex membrane.
4.1.2 Analysis and Conditions
  When the coating layer of an un-rolled coiled collage carrier of the present invention or an un-rolled pre-rolled TachoSil® is wetted, the maximal pressure the carriers can withstand, their adhesive strengths and their air permeability's can be measured by a Pressure Chamber.
4.1.3 Equipment
  The pressure chamber (PCT chamber) is made from Plexiglas 20×20×20 cm, from MHM Morawitz, Nuremberg.
  PCT-Test Membrane (Red THM with a standard hole Ø 1 cm; from MHM Morawitz, Nuremberg) PCT-Test Membrane (Red THM without hole; from MHM Morawitz, Nuremberg).

Blood Pressure Apparatus, GMP qualified equipment. Other suitable GMP qualified
Blood Pressure Apparatus may be used.
Teflon weight (150.0 g Ø 3 cm).
An air tight plastic box with desiccant.
Template for cutting out a piece of collagen carrier (3×3 cm).
Forceps, scalpel and scissors.
Stopwatch.

Figure 4:
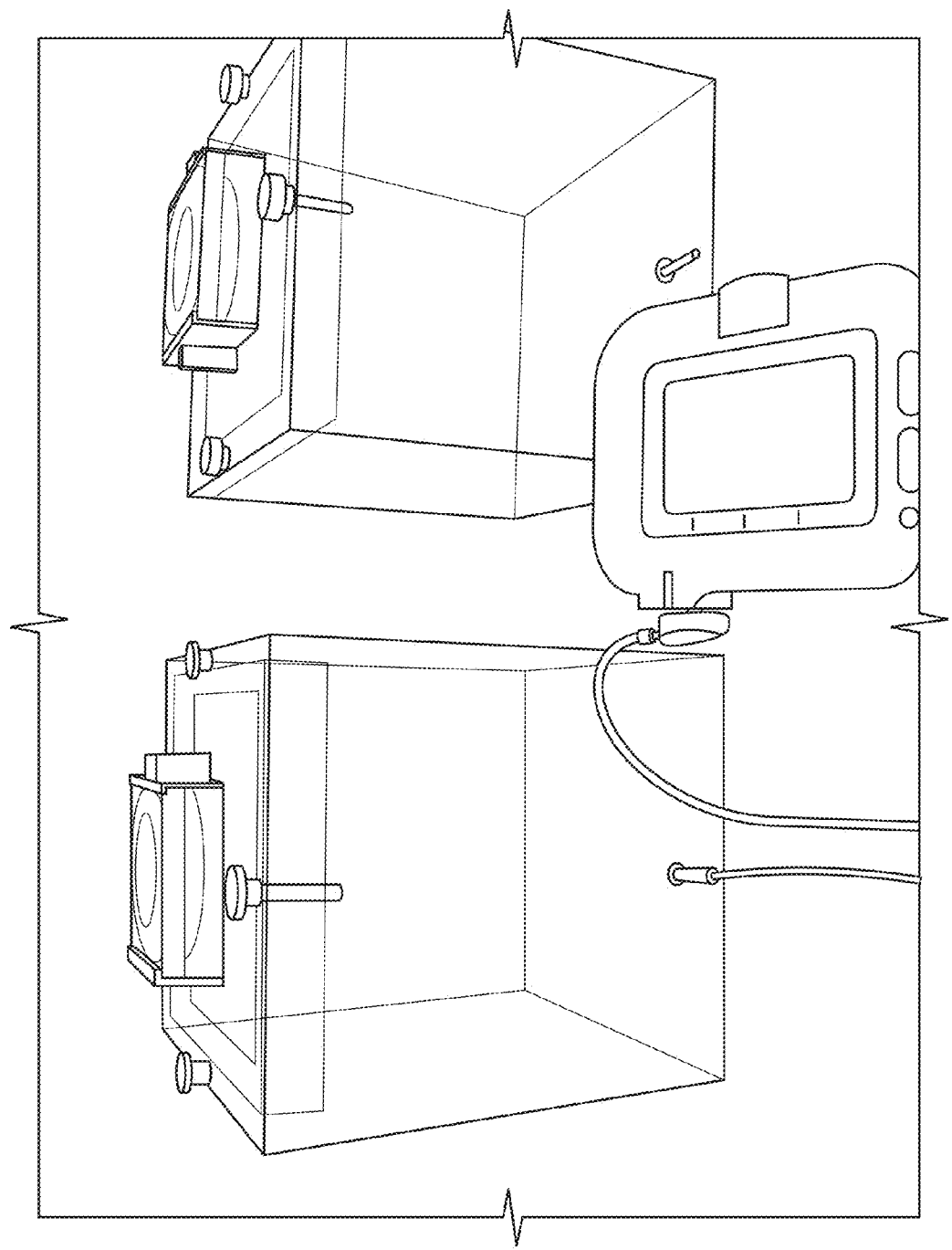
FIG. 4 shows PCT testing chambers and a blood pressure apparatus.

FIG. 4 shows PCT testing chambers and blood pressure apparatus.

4.1.4 Reagents 0.9% NaCl solution (isotonic saline).

4.1.5 Samples

As a minimum it is recommended to perform 5-duplicate per batch/conditioning. NB: It is very important to focus on minimizing the exposure to moisture from the air of the coiled collage carrier of the present invention or the TachoSil®. Hence, it is necessary to store the unpacked fleeces in an airtight box with desiccant. Before performing a PCT test a System Suitablility test must be performed on all the PCT chambers that are to be used.

4.1.6 Performance of the PCT Test

A membrane (with hole) is placed onto the PCT test chamber

The coiled collagen carrier of the present invention or the pre-rolled TachoSil® is gently un-rolled and placed with the yellow side (i.e. the coating layer) facing downwards. By using the template for cutting, a piece of 3×3 cm square collagen carrier is cut out of the un-rolled collagen carrier.

The collagen carrier cut-out is immediately placed inside the dry box if it is not possible to place it on the membrane straight away.

The coating layer is thoroughly wetted by immersing the coated (yellow) side in 0.9% NaCl solution (for approximately 5 s). The collagen layer cut-out must not get wet. Immediately thereafter, the collagen carrier cut-out is placed on the membrane of the PCT chamber with the yellow side facing down against the membrane. It is gently pressed with a finger on the edges where after the teflon weight is carefully placed on top of it. The timer is set to 5 minutes.

After 5 minutes the weight is carefully removed and by using the pressure device pressure is added to the PCT chamber.

Maximum pressure is noted from the blood pressure apparatus and recorded in a table (see below).

To assess the adhesiveness, each corner of the cut-out is pulled with forceps. The results are recorded in table 2 (see below).

Air leakage through the collagen carrier cut-out (see table 1 below) is recorded as well.

The membrane used is discarded and a new one is put on.

4.1.7 Acceptance Level

The average PCT value for the collagen carrier cut-outs must be above 50 mmHg. No collagen carrier cut-out must be below at least 30 mm Hg, such as at least 35 mmHg, such as preferably 40 mmHg.

4.1.8 System Suitability Test

A System Suitability Test is carried out for all chambers that are used for measuring the PCT. Each time a new membrane (without hole) is used, pressure must be put on it one time (activation of the membrane) before the actual pressure leak test is performed, as a new membrane provides a higher PCT value the first time it is used.

The activated membrane can be used approx. 4-6 times or until it bursts. It can only be used within the same day. If the membrane bursts, the measurement is discarded. Another membrane is activated and used instead.

The test is carried out both before and after the PCT measurement of the samples.

Activation of Membranes:

1. A membrane is placed on a PCT chamber.
2. Pressure is applied to the chamber and the membrane is inflated.

Performing the Test:

1. The membrane is placed on the first PCT chamber.
2. Pressure is put on the chamber and the value is registered.
3. The test is repeated with all the chambers to be used.

Table for number of tests
Number of tests to be performed by use of one, two or three PCT chamber(s) respectively (after activation of the membrane)

| | Number of chambers | | |
|---|---|---|---|
| Number of tests | One PCT chamber | Two PCT chambers | Three PCT chambers |
| Number of tests taken before samples per chamber | 2 | 1 | 1 |
| Number of tests taken after samples per chamber. | 1 | 1 | 1 |

Requirements for the test: The value (after activation of the membrane) must be >75 mmHg.

The difference in the values between the different chambers may not be higher than 10 mmHg and not greater than 5 mmHg for the same chamber.

Example 4.2

In the following experiment collagen carriers with an average density of 3.62 mg/cm$^3$ were compressed between two rollers (roller diameter 50 mm) after application of ethanol to the fibrinogen and thrombin coated side of the collagen carrier. The compressed collagen carriers were rolled by use of a gripping device. The rolled collagen carriers were then unrolled to be tested in an adhesive strength test (PCT test). As can be seen from the table below the average PCT value of the unrolled collagen carriers was 78 mmHg and all individual PCT values were above 50 mm Hg. The results indicate that the collagen carriers according to the invention can undergo the process of humidification, compression and rolling according to the invention while maintaining the adhesive strength. The value of the adhesive strength is an indirect measurement of the haemostatic/sealing properties of the rolled carrier.

The collagen carriers used for the experiment had initially at least one of the following physical properties: elasticity module in the range of 5-100 N/cm$^2$, density of 1-10 mg/cm$^3$, chamber diameter of more than 0.75 mm and less than 4 mm and/or having a chamber diameter average below 3 mm and evenly distributed and fixed upon said collagen carrier solid fibrinogen and solid thrombin.

TABLE 1 average density of collagen carriers was 3.62 mg/cm³

| Average density of collagen carrier mg/cm³ | Ethanol applied mg/cm² | Gap size between rollers | PCT value mm Hg |
|---|---|---|---|
| 3.62 | 4.3 | 0.6 | 92 |
| 3.62 | 4.3 | 0.6 | 79 |
| 3.62 | 4.3 | 0.6 | 77 |
| 3.62 | 4.3 | 0.6 | 81 |
| 3.62 | 4.3 | 0.6 | 52 |
| 3.62 | 4.3 | 0.6 | 101 |
| 3.62 | 4.3 | 0.6 | 81 |
| 3.62 | 4.3 | 0.6 | 70 |
| 3.62 | 4.3 | 0.6 | 72 |
| 3.62 | 4.3 | 0.6 | 71 |
| | | | Average: 78 |

The average density of the collagen carriers mentioned above is calculated as the average density of the collagen carrier excluding the coating layer.

Example 4.3

In the following experiment collagen carriers with an average density of 4.05 mg/cm³ were compressed between two rollers (roller diameter 50 mm) after application of ethanol to the fibrinogen and thrombin coated side of the collagen carrier. The compressed collagen carriers were rolled by use of a gripping device. The rolled collagen carriers were then unrolled to be tested in an adhesive strength test (PCT test). As can be seen from the table below the average PCT value of the unrolled collagen carriers was 94 mmHg and all individual PCT values were above 50 mm Hg. The results indicate that the collagen carriers according to the invention can undergo the process of humidification, compression and rolling according to the invention while maintaining the adhesive strength. The value of the adhesive strength is an indirect measurement of the haemostatic/sealing properties of the rolled carrier.

The collagen carriers used for the experiment had initially at least one of the following physical properties: elasticity module in the range of 5-100 N/cm², density of 1-10 mg/cm³, chamber diameter of more than 0.75 mm and less than 4 mm and/or having a chamber diameter average below 3 mm and evenly distributed and fixed upon said collagen carrier solid fibrinogen and solid thrombin.

TABLE 2 average density of collagen carriers was 4.05 mg/cm³. The average density of the collagen carriers is calculated as the average density of the collagen carrier excluding the coating layer.

| Average density of collagen carrier mg/cm³ | Ethanol applied mg/cm² | Gap size between rollers | PCT value mm Hg |
|---|---|---|---|
| 4.05 | 4.2 | 0.6 | 107 |
| 4.05 | 4.2 | 0.6 | 67 |
| 4.05 | 4.2 | 0.6 | 95 |
| 4.05 | 4.2 | 0.6 | 103 |
| 4.05 | 4.2 | 0.6 | 89 |
| 4.05 | 4.2 | 0.6 | 98 |
| 4.05 | 4.2 | 0.6 | 86 |
| 4.05 | 4.2 | 0.6 | 114 |
| 4.05 | 4.2 | 0.6 | 103 |
| 4.05 | 4.2 | 0.6 | 75 |
| | | | Average: 94 |

Example 4.4

The table 3 shows the results of the adhesive strength of a collagen carrier as measured by a PCT test. Please note that the carrier has not been subjected to the humidification, compression and rolling process as in the examples above, i.e. example 4.1 and 4.2.

The collagen carriers used for the experiment initially had at least one of the following physical properties: elasticity module in the range of 5-100 N/cm², density of 1-10 mg/cm³, chamber diameter of more than 0.75 mm and less than 4 mm and/or having a chamber diameter average below 3 mm and evenly distributed and fixed upon said collagen carrier solid fibrinogen and solid thrombin.

TABLE 3 average density of collagen carriers was 4.08 mg/cm³. The average density of the collagen carriers is calculated as the average density of the collagen carrier excluding the coating layer.

| Average density of collagen carrier mg/cm³ | PCT value mm Hg |
|---|---|
| 4.08 | 96 |
| 4.08 | 83 |
| 4.08 | 81 |
| 4.08 | 59 |
| 4.08 | 82 |
| 4.08 | 76 |
| 4.08 | 102 |
| 4.08 | 82 |
| 4.08 | 83 |
| 4.08 | 90 |
| | Average: 83 |

Example 5—Amounts of Ethanol

The present example was made to test the influence on PCT values of the factors; amount of ethanol applied and strip weight for a fixed gap size and fixed RH in the room. By the "weight" of the collagen carriers is meant the weight of the collagen carrier excluding the weight of the coating layer.

Successful pre-rolled TachoSil®'s or successful coiled collagen carriers of the present invention were the ones that had PCT mean value of ≥50 mm Hg and PCT single values of ≥40 mm Hg.

5.1 Material Used

The test has been based on use of the following three batches of midi sized fleeces (none of the fleeces have been gamma irradiated:
  10622250 (strip weight: approx.: 920 mg based on measurement of 10 strips).
  10634435 (strip weight: approx. 1180 mg).
  10657586 (strip weight: approx.: 1261-1500 designated as: 1380 mg Please note that the "weight" of the collagen carriers mentioned above means the weight of the collagen carrier excluding the weight of the coating layer.

5.2 Factors Used

The design used was a full 3² factorial desing with three replication of the centre point.

Fixed factors: Fixed Gap size: 0.6 mm. RH in room: 50% (excursion to 55% is allowed). Temperature in the room (18) 20-22° C.

Variable factors: Ethanol levels: 30-40 mg/fleece; 90-100 mg/fleece; 150-160 mg/fleece. Strip weight.

5.3 Responses

PCT (mm Hg)

Fleece dimensions after rolling (diameter (cm) and length (cm))

5.4 Results

Table demonstrating temperature and RH when processing the fleeces.

By "strip weight" is meant the weight of the collagen carrier excluding the weight of the coating layer.

| Experiment | Ethanol {mg/fleece} | Strip weight (mg) | Temp (° C.) RH % During rolling | Temp (° C.) RH % Prior to drying | Temp (54.0% ° C.) RH % After drying |
|---|---|---|---|---|---|
| N10 | 95 | 1180 | 21.8-22.1° C. 45.2-53% | 22.1° C. 55.2% | 21.6° C. 54.3% |
| N4 | 39 | 1180 | 20.5-20.9° C. 46.8-47.7% | 21.0° C. 48.1% | 22.2° 53.8% |
| N1 | 39 | 920 | 21-1-21.4° C. 48.6-48.8% | 21.4 49.0% | 22.2° C. 54.3 |
| N5 | 98 | 1180 | 20.5-20.7° C. 50.6-51.0 | 20.8° C. 51.4% | 21° 55% |
| N7 | 39 | 1380 | 20.8-20.9° C. 53.0-53.2% | 21.0° C. 53.5% | 21.0° C. 59.2% |
| N6 | 153 | 1180 | 21.2-21.3° C. 54.5-54.6% | 21.4° C. 55.0% | 20.9° C. 56.6% |
| N11 | 94 | 1180 | 19.0-19.1° C. 51.7-51.9% | 19.2° C. 51.8% | 19.9° C. 55.0% |
| N12 | 94 | 1180 | 19.3-19.4° C. 51.8-51.9% | 19.4° C. 52.0% | 20.1° C. 55.2% |
| N8 | 94 | 1380 | 19.4-19.6° C. 52.2-52.4% | 19.6° C. 52.3% | 20.2° C. 55.9% |
| N3 | 158 | 920 | 19.6-19.8° C. 53.5-53.4% | 19.9° C. 53.5% | 19.8° C. 56.7% |
| N2 | 104 | 920 | 18.9-19.2° C. 53.0% | 19.3° C. 53.0% | 20.0° C. 52.9% |
| N9 | 154 | 1380 | 19.8-19.9° C. 53.9-54.0% | 20.0° C. 54.0% | 20.8° C. 55.8% |

Table demonstrating fleece dimensions after rolling (diameter (cm) and length (cm)) and the obtained PCT average value in mmHg.

By "strip weight" is meant the weight of the collagen carrier excluding the weight of the coating layer.

| Experiment | Ethanol {mg/fleece} | Strip weight {mg strip} | Length of rolled fleece - average {cm} | Diameter of rolled fleece - average {cm} | PCT average value {mmHg} |
|---|---|---|---|---|---|
| N1 | 39 | 920 | 4.72 | 0.88 | 90 |
| N2 | 104 | 920 | 4.76 | 0.86 | 77 |
| N3 | 158 | 920 | 4.68 | 0.81 | 72 |
| N4 | 39 | 1180 | 4.85 | 0.91 | 95 |
| N5 | 98 | 1180 | 4.76 | 0.88 | 79 |
| N6 | 153 | 1180 | 4.62 | 0.86 | 85 |
| N7 | 39 | 1380 | 4.64 | 0.90 | 92 |
| N8 | 94 | 1380 | 4.69 | 0.87 | 86 |
| N9 | 154 | 1380 | 4.63 | 0.84 | 80 |
| N10 | 95 | 1180 | 4.75 | 0.86 | 84 |
| N11 | 94 | 1180 | 4.72 | 0.86 | 98 |
| N12 | 94 | 1180 | 4.80 | 0.87 | 90 |

From the above results table it is clear that all tested fleeces are successful i.e. they all have PCT mean value of ≥50 mm Hg and PCT single values of ≥40 mm Hg (data not shown).

Further, as apparent from the above results, the diameter of coiled fleece-averages is well below 10 mm and the length of the coiled fleeces well below 5 cm. Also, it was apparent from the above results that when using the process according to the invention, maintaining the atmosphere surrounding the collagen carrier and humidification device while being humidified compressed and coiled at a temperature of about 18-22° C. and a relative humidity of about 30-50% produces successful fleeces using ethanol levels of 30-40 mg/fleece; 90-100 mg/fleece; 150-160 mg/fleece.

Example 6—Direct Coiling of TachoSil®

The present example investigates the steps of humidification and compression of a collagen carrier of the present invention, i.e. a TachoSil®.

A TachoSil® was subjected to direct coiling without previous humidification and compression. The coiling was performed within an apparatus according to the invention excluding the steps of humidification and compression.

Figure 6:
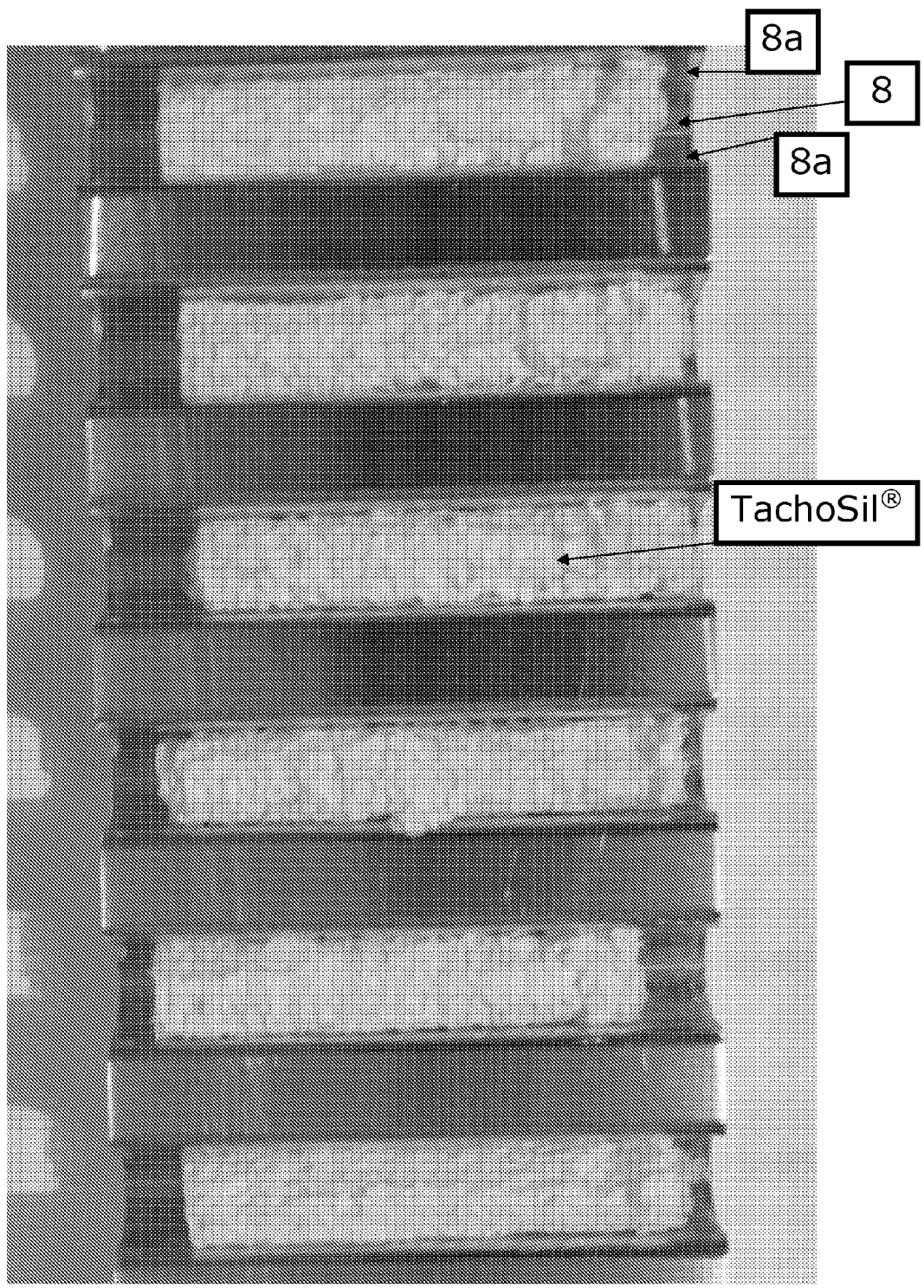
FIG. 6 shows TachoSil® (collagen carriers with a weight of about 1000 mg) that have been coiled directly i.e. without being previously humidified and compressed. Note the cracked surface of the coating. By the "weight" of the collagen carriers is meant the weight of the collagen carrier excluding the weight of the coating layer.

The resulting directly coiled TachoSil®'s had a "flossy" appearance and their coating layer had through-going cracks that were visible to the naked eye (see FIG. 6).

When comparing the directly coiled TachoSil®'s with the coiled collagen carriers of the present invention (see FIG. 3), it was easy to see the differences i.e. the coiled collagen carriers of the present invention are form-stable in the sense that they do not un-coil "when at rest", such as when laying un-supported on a flat surface. Further, their coating layers had no through-going cracks and they did not look "flossy" but rather had a smooth, substantially even surface.

Example 7: Use of Pre-Rolled TachoSil® in Minimally Invasive Surgery in a Pig Model In order to examine the haemostatic properties of the pre-rolled TachoSil® product, a female pig model was operated by laparoscopy and haemostasis was carried out using the pre-rolled ready-to-use TachoSil® product.

Protocol:

After orotracheal intubation the pneumoperitoneum was established in traditional Hasson technique. We used a 12 mm trocar. CO2 gas was insufflated slowly till 12 mmHg maximum. After insertion of the optic, an open 12 mm trocar was placed in the left upper quadrant, and one 5 mm trocar was placed in the right upper quadrant under direct vision.

A 3×3 cm defect was surgically inflicted on the right liver lobe with a depth of 2 mm. Diffuse bleeding started. A pre-rolled TachoSil® was inserted at the bleeding site by the use of a dissector via the 12 mm trocar. The insertion was easily done without breaking the roll. Opening the roll with a dissector and a grasper was successful without any problems. The specimen of pre-rolled Tachosil® was placed on the inflicted wounds and pressed onto the liver by use of a wet sponge for 2 minutes. A similar procedure was carried out on a left liver site. Control of bleeding at the wound sites showed that haemostasis was successful. Following surgery the pig was observed for 7 days to check for any complications (none were observed).

Figure 2:
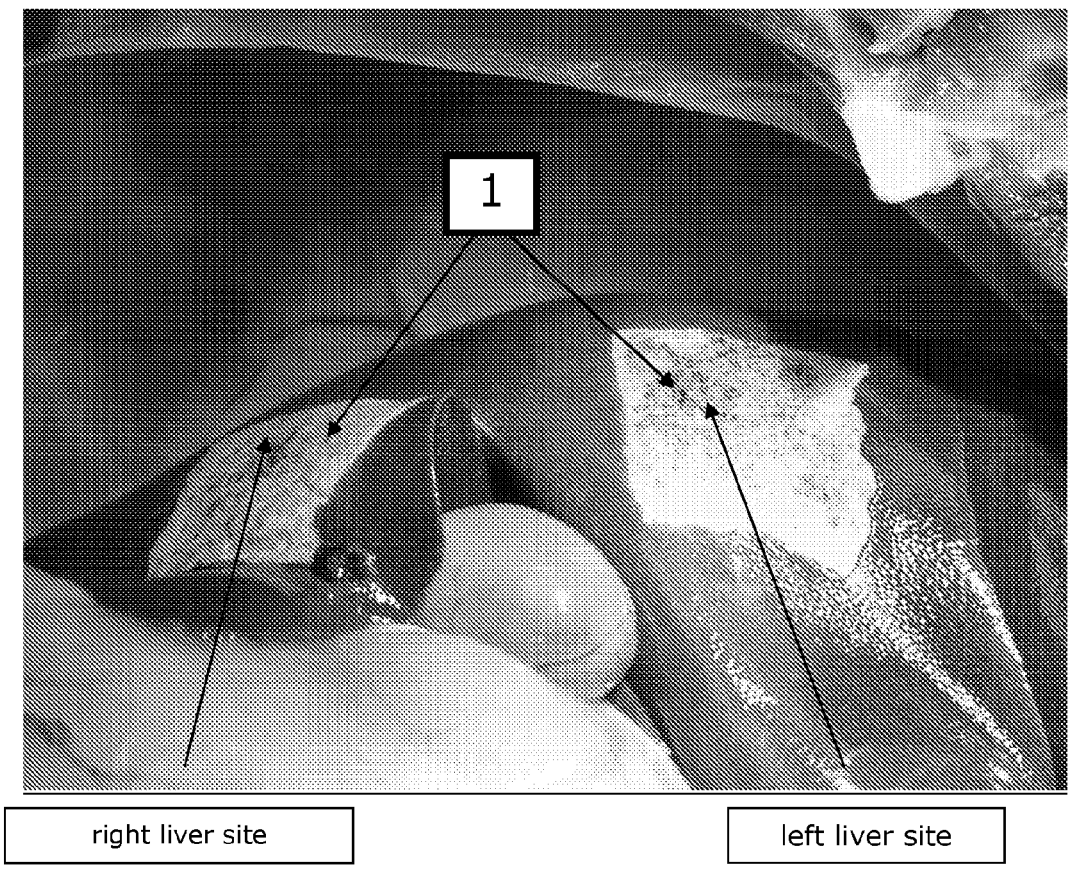
FIG. 2 shows the appearance of prerolled collagen carriers (in uncoiled state) applied in vivo in a pig liver, 7 days after surgery (see description in Example 7).

7 days after surgery the pig was sacrificed and the pre-rolled Tachosil® patches on the liver surface were checked for any irregularities (see the photo in FIG. 2). No irregularities appeared to be present compared to what would be expected with a commercially-available (flat-packed, non-rolled) Tachosil® product. Bleeding had been successfully controlled on both sites.

Example 8—Uptake of Water into Ethanol and Impact on PCT-Value

In order to examine the amount of water absorbed in absolute ethanol as a function of time when exposed the conditions of approx 50% RH and 20° C., the following experiment was made:

The absolute ethanol had been exposed to moisture when kept in a open beaker 8.1 Results—Uptake of Water into Ethanol Interval from ½ to 1½ hour: Approx. 0.5% (concentration of ethanol: approx 99.5%).

Interval up to approx. 20 hours: Maximum 2.4% (concentration of ethanol: ≥97.6%).

8.2—Impact on PCT-Value

Based on the findings of uptake of water into ethanol it was investigated whether the use of ethanol containing 2.4% of water would have any impact on the coiling process or on the PCT value when tested after coiling and drying.

8.3 Test Set Up—PCT-Value and Coiling Process

Batch No. 10657586 (strip weight: approx.: 1261-1500 designated as: 1380 mg. These fleeces have not been gamma irradiated.

By "strip weight" is meant the weight of the collagen carrier excluding the weight of the coating layer.

Factors:

Fixed: Gap size=0.6 mm, RH in room=≤50%, excursion to 55% is allowed),

Ethanol levels=80 mg/fleece±10 mg/fleece

Variable: Ethanol concentration=99.9% and 97.6%.

Responses: PCT (Mm Hg)

Design: 10 fleeces were coiled based on moisturizing with 97.6% ethanol and fleeces were coiled based on moisturizing with absolute ethanol (99.9%) 8.4 Results—PCT-Value and Coiling Process Batch 10657586 (≈1380 mg stripweight):

99.9% Ethanol used for moisturizing: Mean PCT-values: 107 mm Hg and Single PCT-values: 107, 111, 108, 122, 112, 113, 119, 76, 98, 105 mm Hg 97.6% Ethanol used for moisturizing: Mean PCT-values: 101 mm Hg and Single PCT-values: 95, 110, 85, 113, 119, 100, 109, 90, 114, 71 mm Hg.

By "strip weight" is meant the weight of the collagen carrier excluding the weight of the coating layer.

A t-test on possible difference between using 99.9% and 97.6% Ethanol: P (T≤t)=0.32 indicated that a significant difference could not be found.

Thus, the addition of up to 2.4% of water in the ethanol used for moisturizing in the coiling process, that is approx 20 hours of exposure to RH up to 50% at 20° C., did not have any significant impact on the PCT values or on the fleece behaviour during rolling.

Example 9—Impact on Collagen Carrier of RH of Surrounding Air During Processing 9.1 Objective The present example demonstrates the impact on PCT values of room conditions (20-22° C./40-60% RH) during the manufacture of PreRolled TachoSil® fleeces. The water content (KF values) were measured as support using a standard Karl Fischer titration method.

Factors: Gap size: 0.6 mm and ethanol levels: 94 mg/fleece 9.2 Results—PCT (TachoSil® Batch 10634435—not Gamma Irradiated):

| Room conditions | PCT values (mm Hg) |
| --- | --- |
| I (20-21° C./45-49% RH) | Single values: 90, 112, 115, 41, 57, 104, 44, 71, 112, 68, 65<br>Mean value: 80 (std.: 28) |
| II (20-21° C./51-52% RH) | Single values: 66, 104, 77, 97, 75, 110, 95, 67, 87, 51, 74, 53, 89<br>Mean values: 80 (std.: 18) |

-continued

| Room conditions | PCT values (mm Hg) |
| --- | --- |
| III (20-21° C./57-58% RH) | Single values: 69, 61, 40, 59, 112, 60, 75, 64, 97, 39, 67, 73, 73<br>Mean value: 68 (std.: 20) |
| IV (20-21° C./61-63% RH) | Single values: 61, 67, 54, 51, 66, 89, 61, 74, 81, 60, 54, 66, 59<br>Mean value: 65 (std.: 11)<br>Comments: Rolls sticky when unrolling at PCT measurements |

As can be seen from the table above, 57-58% RH produces a single PCT-value of less than 40 mm Hg i.e. room condition III.

| Room conditions | KF, % water content; n = 2-4.<br>Measured immediately after 30 min of Ethanol dry off |
| --- | --- |
| I (20-21° C./45-49% RH) | Average: 11.21% (% RSD: 1.28) |
| II (20-21° C./51-52% RH) | Average: 12.48% (% RSD: 0.83) |
| III (20-21° C./57-58% RH) | Average: 13.42% (% RSD: 4.02) |
| IV (20-21° C./61-63% RH) | Average: 16.12% (% RSD: 0.61) |

As can be seen from the table above the % water content in the collagen carriers increases as the RH increases, but the PCT-values were still successful.

The invention claimed is:

1. A method of treating a patient comprising administering to a patient in need thereof a form-stable coiled hemostatic collagen carrier
   comprising a collagen sponge with a coating layer on the top surface of the collagen sponge, the coating layer comprising thrombin and fibrinogen, and
   having the shape of an elongate element with a number of windings of the collagen carrier about the longitudinal axis of the elongate element and at least one outer winding(s),
   wherein
   the at least one outer winding(s) are orientated so that the coating layer constitutes the outer surface of each outer winding,
   and wherein
   the coiled collagen carrier is form-stable and defines a collagen carrier in a coiled configuration where said at least one outer winding(s) proceed along a spiral in a cross section of the collagen carrier.

2. The method of treating a patient according to claim 1, wherein the method of treatment further comprises a method of surgery.

3. The method of treating a patient according to claim 1, wherein the method of treatment further comprises a method of treating an injury associated with performing minimally invasive surgery in a patient.

4. The method of claim 3, wherein leakage of cerebrospinal fluid or air/gas is present at the injury.

5. The method of treating a patient according to claim 1, wherein the method of treatment further comprises a method of preventing or treating an injury associated with performing endoscopic surgery in a patient.

6. The method of treating a patient according to claim 1, wherein the method of treatment further comprises a method of preventing injury to or treating a tissue in need of sealing and/or glueing.

7. The method of claim 6, wherein the tissue is selected from brain, spinal cord, nerves, and nerve tissue.

8. The method of treating a patient according to claim 1, wherein the method of treatment further comprises a method of improving or providing hemostasis in a patient.

9. The method of treating a patient according to claim 1, wherein the method of treatment further comprises a method of promoting tissue sealing in a patient.

10. The method of treating a patient according to claim 1, wherein the method of treatment further comprises a method of providing suture support in a patient.

11. The method of treating a patient according to claim 1, wherein the method of treatment further comprises a method of preventing or treating an injury associated with performing laparoscopic surgery in a patient.

12. The method of treating a patient according to claim 1, wherein the method of treatment further comprises a method of preventing or treating an injury associated with performing thoracoscopic surgery in a patient.

13. The method of treating a patient according to claim 1, wherein the method of treatment further comprises a method of preventing or treating post-surgical tissue adhesions in a patient.

14. The method of treating a patient according to claim 1, wherein the method of treatment further comprises a method of preventing or treating bleeding in a patient's tissue in need of hemostasis.

\* \* \* \* \*